US007576092B2

(12) United States Patent
Chavez et al.

(10) Patent No.: US 7,576,092 B2
(45) Date of Patent: Aug. 18, 2009

(54) BENZOFURO- AND BENZOTHIENOPYRIMIDINE MODULATORS OF THE HISTAMINE $H_4$ RECEPTOR

(75) Inventors: Frank Chavez, San Diego, CA (US); Michael P. Curtis, Bozrah, CT (US); James P. Edwards, San Diego, CA (US); Anne E. Fitzgerald, San Diego, CA (US); Laurent Gomez, San Diego, CA (US); Cheryl A. Grice, Carlsbad, CA (US); Aaron M. Kearney, Lakeside, CA (US); Jing Liu, San Diego, CA (US); Neelakandha S. Mani, San Diego, CA (US); Brad M. Savall, San Diego, CA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/827,354

(22) Filed: Jul. 10, 2007

(65) Prior Publication Data

US 2008/0015200 A1    Jan. 17, 2008

Related U.S. Application Data

(60) Provisional application No. 60/830,192, filed on Jul. 11, 2006.

(51) Int. Cl.
*A01N 43/54*  (2006.01)
*A61K 31/505*  (2006.01)
*C07D 239/00*  (2006.01)
*C07D 471/00*  (2006.01)
*C07D 487/00*  (2006.01)
*C07D 491/00*  (2006.01)

(52) U.S. Cl. ...................... 514/267; 544/250
(58) Field of Classification Search ........... 544/250; 514/267
See application file for complete search history.

(56) References Cited

U.S. PATENT DOCUMENTS

| 3,706,747 | A | 12/1972 | De Angelis et al. |
|---|---|---|---|
| 3,755,583 | A | 8/1973 | De Angelis et al. |
| 4,703,053 | A | 10/1987 | Connor et al. |
| 6,080,745 | A | 6/2000 | Davey et al. |
| 6,482,948 | B1 | 11/2002 | Yamada et al. |
| 6,875,781 | B2 | 4/2005 | Hong et al. |
| 7,291,733 | B2 * | 11/2007 | Cywin et al. ............ 546/83 |
| 2004/0058940 | A1 | 3/2004 | Eggenweiler et al. |
| 2005/0153989 | A1 | 7/2005 | Grotzfeld et al. |
| 2005/0197354 | A1 | 9/2005 | Andries et al. |
| 2006/0111416 | A1 | 5/2006 | Lane et al. |

FOREIGN PATENT DOCUMENTS

| EP | 1767537 A1 | 3/2007 |
|---|---|---|
| JP | 6-220059 * | 1/1993 |
| JP | 06220059 A | 8/1994 |
| WO | WO 2005/042500 A1 | 5/2005 |
| WO | WO 2005/069865 A2 | 8/2005 |
| WO | WO 2006/050965 A1 | 5/2006 |
| WO | WO 2007/090852 * | 8/2007 |
| WO | WO 2007/090852 A1 | 8/2007 |
| WO | WO 2007/090853 A1 | 8/2007 |
| WO | WO 2007/090854 A1 | 8/2007 |
| WO | WO2008/074445 | 6/2008 |

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modern Pharmaceutics, Marcel Dekker, New York, 1996.*
Lim, et al., The Emerging Role of the Histamine H4 Receptor in Anti-inflammatory Therapy, Current Topics in Medicinal Chemistry, 6, 1365-1373 (2006).*
Amin, K. et al. Inflammation and Structural Changes in the Airways of Patients with Atopic and Nonatopic Asthma. Am. J. Resp. Crit. Care Med. 2000, 162(6), 2295-2301.
Banker, G.S. et al. Modern Pharmaceutics, Marcel Dekker: New York, 1996, pp. 451, 596.
Bell, J.K. et al. Involvement of histamine $H_4$ and $H_1$ receptors in scratching induced by histamine receptor agonists in BalbC mice. Br. J. Pharmacol. 2004, 142(2), 374-380.
Benoist, C. et al. Mast cells in autoimmune disease. Nature 2002, 420(6917), 875-878.
Buckland, K.F. et al. Histamine induces cytoskeletal changes in human eosinophils via the $H_4$ receptor. Br. J. Pharmacol. 2003, 140(6), 1117-1127.
Coge, F. et al. Structure and Expression of the Human Histamine $H_4$-Receptor Gene. Biochem. Biophys. Res. Commun. 2001, 284(2), 301-309.
Cohen, J. The immunopathogenesis of sepsis. Nature 2002, 420(6917), 885-891.
Coussens, L.M. et al. Inflammation and cancer. Nature 2002, 420(6917), 860-867.
Crimi, E. et al. Increased numbers of mast cells in bronchial mucosa after the late-phase asthmatic response to allergen. Am. Rev. Respir. Dis. 1991, 144(6), 1282-1286.
de Esch, I.J.P. et al. The histamine $H_4$ receptor as a new therapeutic target for inflammation. Trends Pharmacol. Sci. 2005, 26(9), 462-469.
Fokkens, W.J. et al. Dynamics of mast cells in the nasal mucosa of patients with allergic rhinitis and non-allergic controls: a biopsy study. Clin. Exp. Allergy 1992, 22(7), 701-710.

(Continued)

*Primary Examiner*—James O Wilson
*Assistant Examiner*—Erich A Leeser

(57) ABSTRACT

Benzofuro- and benzothienopyrimidine compounds are described, which are useful as $H_4$ receptor modulators. Such compounds may be used in pharmaceutical compositions and methods for the treatment of disease states, disorders, and conditions mediated by $H_4$ receptor activity, such as allergy, asthma, autoimmune diseases, and pruritis.

30 Claims, No Drawings

OTHER PUBLICATIONS

Fung-Leung, W.-P. et al. Histamine H4 receptor antagonists: The new antihistamines? Curr. Opin. Invest. Drugs 2004, 5(11), 1174-1183.

Gantner, F. et al. Histamine $H_4$ and $H_2$ Receptors Control Histamine-Induced Interleukin-16 Release from Human $CD8^+$ T Cells. J. Pharmacol. Exp. Ther. 2002, 303(1), 300-307.

Gauvreau, G.M. et al. Increased Numbers of Both Airway Basophils and Mast Cells in Sputum after Allergen Inhalation Challenge of Atopic Asthmatics. Am. J. Resp. Crit. Care Med. 2000, 161(5), 1473-1478.

Gutzmer, R. et al. Histamine $H_4$ Receptor Stimulation Suppresses IL-12p70 Production and Mediates Chemotaxis in Human Monocyte-Derived Dendritic Cells. J. Immunol. 2005, 174(9), 5224-5232.

Hofstra, C.L. et al. Histamine $H_4$ Receptor Mediates Chemotaxis and Calcium Mobilization of Mast Cells. J. Pharmacol. Exp. Ther. 2003, 305(3), 1212-1221.

Ikawa, Y. et al. Histamine $H_4$ Receptor Expression in Human Synovial Cells Obtained from Patients Suffering from Rheumatoid Arthritis. Biol. Pharm. Bull. 2005, 28(10), 2016-2018

Kassel, O. et al. Local increase in the number of mast cells and expression of nerve growth factor in the bronchus of asthmatic patients after repeated inhalation of allergen at low-dose. Clin. Exp. Allergy 2001, 31(9), 1432-1440.

Kirby, J.G. et al. Bronchoalveolar cell profiles of asthmatic and nonasthmatic subjects. Am. Rev. Respir. Dis. 1987, 136(2), 379-383.

Krug, N. et al. Interleukin 16 and T-cell Chemoattractant Activity in Bronchoalveolar Lavage 24 Hours after Allergen Challenge in Asthma. Am. J. Resp. Crit. Care Med. 2000, 162(1), 105-111.

Libby, P. Inflammation in atherosclerosis. Nature 2002, 420, 868-874.

Lim et al. The Emerging Role of the Histamine H4 Receptor in Anti-Inflammatory Therapy. Curr. Topics Med. Chem. 2006, 6, 1365-1373.

Ling, P. et al. Histamine $H_4$ receptor mediates eosinophil chemotaxis with cell shape change and adhesion molecule upregulation. Br. J. Pharmacol. 2004, 142(1), 161-171.

Lippert, U. et al. Human Skin Mast Cells Express H2 and H4, but not H3 Receptors. J. Invest. Dermatol. 2004, 123(1), 116-123.

Liu, C. et al. Cloning and Pharmacological Characterization of a Fourth Histamine Receptor ($H_4$) Expressed in Bone Marrow. Mol. Pharmacol. 2001, 59(3), 420-426.

Mashikian, V.M. et al. Identification of IL-16 as the lymphocyte chemotactic activity in the bronchoalveolar lavage fluid of histamine-challenged asthmatic patients. J. Allergy Clin. Immunol. 1998, 101 (6, Part 1), 786-792.

Morse, K.L. et al. Cloning and Characterization of a Novel Human Histamine Receptor. J. Pharmacol. Exp. Ther. 2001, 296(3), 1058-1066.

Nathan, C. Points of control in inflammation. Nature 2002, 420(6917), 846-852.

O'Reilly, M. et al. Identification of a $H_4$ Receptor on Human Eosinophils—Role in Eosinophil Chemotaxis. J. Recept. Signal Transduction 2002, 22(1-4), 431-448.

Slater, A. et al. Increase in epithelial mast cell numbers in the nasal mucosa of patients with perennial allergic rhinitis. J. Laryngol. Otol. 1996, 110, 929-933.

Steinberg, D. Atherogenesis in perspective: Hypercholesterolemia and inflammation as partners in crime. Nature Med. 2002, 8(11), 1211-1217.

Takeshita, K. et al. Critical Role of Histamine $H_4$ Receptor in Leukotriene $B_4$ Production and Mast Cell-Dependent Neutrophil Recruitment Induced by Zymosan in Vivo. J. Pharmacol. Exp. Ther. 2003, 307(3), 1072-1078.

Thurmond, R.L. et al. A Potent and Selective Histamine H4 Receptor Antagonist with Anti-Inflammatory Properties. J. Pharmacol. Exp. Ther. 2004, 309(1), 404-413.

Tracey, K.J. The inflammatory reflex. Nature 2002, 420(6917), 853-859.

Varga, C. et al. Inhibitory effects of histamine $H_4$ receptor antagonists on experimental colitis in the rat. Eur. J. Pharmacol. 2005, 522(1-3), 130-138.

Voehringer, D. et al. Type 2 Immunity Reflects Orchestrated Recruitment of Cells Committed to IL-4 Production. Immunity 2004, 20(3), 267-277.

Weiner, H.L. et al. Inflammation and therapeutic vaccination in CNS diseases. Nature 2002, 420(6917), 879-884.

Wolff, M.E. Burger's Medicinal Chemistry and Drug Discovery, $5^{th}$ Ed., vol. 1: Principles and Practice, John Wily & Sons, 1995, p. 975.

Chen et al. Synthesis of Benxo[b]furans via CuI-Catalyzed Ring Closure. Jour. Organic Chemistry, 2005, vol. 70, No. 17, pp. 6964-6967.

International Search Report dated Oct. 7, 2008.

\* cited by examiner

BENZOFURO- AND BENZOTHIENOPYRIMIDINE MODULATORS OF THE HISTAMINE $H_4$ RECEPTOR

This application claims the benefit of U.S. Provisional Application Ser. No. 60/830,192, filed on Jul. 11, 2006, which is hereby incorporated by reference in its entirety.

FIELD OF THE INVENTION

The present invention relates to certain benzofuro- and benzothienopyrimidine compounds, pharmaceutical compositions containing them, and methods of using them for the treatment of disease states, disorders, and conditions mediated by histamine $H_4$ receptor activity.

BACKGROUND OF THE INVENTION

The histamine $H_4$ receptor ($H_4R$) is the most recently identified receptor for histamine (for reviews, see: Fung-Leung, W.-P., et al., Curr. Opin. Invest. Drugs 2004, 5(11), 1174-1183; de Esch, I. J. P., et al., Trends Pharmacol. Sci. 2005, 26(9), 462-469). The receptor is found in the bone marrow and spleen and is expressed on eosinophils, basophils, mast cells (Liu, C., et al., Mol. Pharmacol. 2001, 59(3), 420-426; Morse, K. L., et al., J. Pharmacol. Exp. Ther. 2001, 296(3), 1058-1066; Hofstra, C. L., et al., J. Pharmacol. Exp. Ther. 2003, 305(3), 1212-1221; Lippert, U., et al., J. Invest. Dermatol. 2004, 123(1), 116-123; Voehringer, D., et al., Immunity 2004, 20(3), 267-277), CD8$^+$T cells (Gantner, F., et al., J. Pharmacol. Exp. Ther. 2002, 303(1), 300-307), dendritic cells, and human synovial cells from rheumatoid arthritis patients (Ikawa, Y., et al., Biol. Pharm. Bull. 2005, 28(10), 2016-2018). However, expression in neutrophils and monocytes is less well defined (Ling, P., et al., Br. J. Pharmacol. 2004, 142(1), 161-171). Receptor expression is at least in part controlled by various inflammatory stimuli (Coge, F., et al., Biochem. Biophys. Res. Commun. 2001, 284(2), 301-309; Morse, et al., 2001), thus supporting that $H_4$ receptor activation influences inflammatory responses. Because of its preferential expression on immunocompetent cells, the $H_4$ receptor is closely related with the regulatory functions of histamine during the immune response.

A biological activity of histamine in the context of immunology and autoimmune diseases is closely related with the allergic response and its deleterious effects, such as inflammation. Events that elicit the inflammatory response include physical stimulation (including trauma), chemical stimulation, infection, and invasion by a foreign body. The inflammatory response is characterized by pain, increased temperature, redness, swelling, reduced function, or a combination of these.

Mast cell degranulation (exocytosis) releases histamine and leads to an inflammatory response that may be initially characterized by a histamine-modulated wheal and flare reaction. A wide variety of immunological stimuli (e.g., allergens or antibodies) and non-immunological (e.g., chemical) stimuli may cause the activation, recruitment, and de-granulation of mast cells. Mast cell activation initiates allergic inflammatory responses, which in turn cause the recruitment of other effector cells that further contribute to the inflammatory response. It has been shown that histamine induces chemotaxis of mouse mast cells (Hofstra, et al., 2003). Chemotaxis does not occur using mast cells derived from $H_4$ receptor knockout mice. Furthermore, the response is blocked by an $H_4$-specific antagonist, but not by $H_1$, $H_2$ or $H_3$ receptor antagonists (Hofstra, et al., 2003; Thurmond, R. L., et al., J. Pharmacol. Exp. Ther. 2004, 309(1), 404-413). The in vivo migration of mast cells to histamine has also been investigated and shown to be $H_4$ receptor dependent (Thurmond, et al., 2004). The migration of mast cells may play a role in allergic rhinitis and allergy where increases in mast cell number are found (Kirby, J. G., et al., Am. Rev. Respir. Dis. 1987, 136(2), 379-383; Crimi, E., et al., Am. Rev. Respir. Dis. 1991, 144(6), 1282-1286; Amin, K., et al., Am. J. Resp. Crit. Care Med. 2000, 162(6), 2295-2301; Gauvreau, G. M., et al., Am. J. Resp. Crit. Care Med. 2000, 161(5), 1473-1478; Kassel, O., et al., Clin. Exp. Allergy 2001, 31(9), 1432-1440). In addition, it is known that in response to allergens there is a redistribution of mast cells to the epithelial lining of the nasal mucosa (Fokkens, W. J., et al., Clin. Exp. Allergy 1992, 22(7), 701-710; Slater, A., et al., J. Laryngol. Otol. 1996, 110, 929-933). These results show that the chemotactic response of mast cells is mediated by histamine $H_4$ receptors.

It has been shown that eosinophils can chemotax towards histamine (O'Reilly, M., et al., J. Recept. Signal Transduction 2002, 22(1-4), 431-448; Buckland, K. F., et al., Br. J. Pharmacol. 2003, 140(6), 1117-1127; Ling et al., 2004). Using $H_4$ selective ligands, it has been shown that histamine-induced chemotaxis of eosinophils is mediated through the $H_4$ receptor (Buckland, et al., 2003; Ling et al., 2004). Cell surface expression of adhesion molecules CD11b/CD18 (LFA-1) and CD54 (ICAM-1) on eosinophils increases after histamine treatment (Ling, et al., 2004). This increase is blocked by $H_4$ receptor antagonists but not by $H_1$, $H_2$, or $H_3$ receptor antagonists.

The $H_4R$ also plays a role in dendritic cells and T cells. In human monocyte-derived dendritic cells, $H_4R$ stimulation suppresses IL-12p70 production and drives histamine-mediated chemotaxis (Gutzmer, R., et al., J. Immunol. 2005, 174 (9), 5224-5232). A role for the $H_4$ receptor in CD8$^+$T cells has also been reported. Gantner, et al., (2002) showed that both $H_4$ and $H_2$ receptors control histamine-induced IL-16 release from human CD8$^+$T cells. IL-16 is found in the bronchoalveolar fluid of allergen- or histamine-challenged asthmatics (Mashikian, V. M., et al., J. Allergy Clin. Immunol. 1998, 101 (6, Part 1), 786-792; Krug, N., et al., Am. J. Resp. Crit. Care Med. 2000, 162(1), 105-111) and is considered important in CD4$^+$ cell migration. The activity of the receptor in these cell types indicates an important role in adaptive immune responses such as those active in autoimmune diseases.

In vivo $H_4$ receptor antagonists were able to block neutrophillia in zymosan-induced peritonitis or pleurisy models (Takeshita, K., et al., J. Pharmacol. Exp. Ther. 2003, 307(3), 1072-1078; Thurmond, et al., 2004). In addition, $H_4$ receptor antagonists have activity in a widely used and well-characterized model of colitis (Varga, C., et al., Eur. J. Pharmacol. 2005, 522(1-3), 130-138). These results support the conclusion that $H_4$ receptor antagonists have the capacity to be anti-inflammatory in vivo.

Another physiological role of histamine is as a mediator of itch and $H_1$ receptor antagonists are not completely effective in the clinic. Recently, the $H_4$ receptor has also been implicated in histamine-induced scratching in mice (Bell, J. K., et al., Br. J. Pharmacol. 2004, 142(2), 374-380). The effects of histamine could be blocked by $H_4$ antagonists. These results support the hypothesis that the $H_4$ receptor is involved in histamine-induced itch and that $H_4$ receptor antagonists will therefore have positive effects in treating pruritis.

Modulation of $H_4$ receptors controls the release of inflammatory mediators and inhibits leukocyte recruitment, thus providing the ability to prevent and/or treat $H_4$-mediated diseases and conditions, including the deleterious effects of allergic responses such as inflammation. Compounds according to the present invention have H$_4$ receptor modulating properties. Compounds according to the present invention have leukocyte recruitment inhibiting properties. Compounds according to the present invention have anti-inflammatory properties.

Examples of textbooks on the subject of inflammation include: 1) Gallin, J. I.; Snyderman, R., *Inflammation: Basic Principles and Clinical Correlates,* 3rd ed.; Lippincott Williams & Wilkins: Philadelphia, 1999; 2) Stvrtinova, V., et al., *Inflammation and Fever. Pathophysiology Principles of Diseases* (Textbook for Medical Students); Academic Press: New York, 1995; 3) Cecil; et al. *Textbook Of Medicine,* 18th ed.; W.B. Saunders Co., 1988; and 4) Stedman's Medical Dictionary.

Background and review material on inflammation and conditions related with inflammation can be found in articles such as the following: Nathan, C., Nature 2002, 420(6917), 846-852; Tracey, K. J., Nature 2002, 420(6917), 853-859; Coussens, L. M., et al., Nature 2002, 420(6917), 860-867; Libby, P., Nature 2002, 420, 868-874; Benoist, C., et al., Nature 2002, 420(6917), 875-878; Weiner, H. L., et al., Nature 2002, 420(6917), 879-884; Cohen, J., Nature 2002, 420(6917), 885-891; Steinberg, D., Nature Med. 2002, 8(11), 1211-1217.

Thus, small-molecule histamine H$_4$ receptor modulators according to this invention control the release of inflammatory mediators and inhibit leukocyte recruitment, and may be useful in treating inflammation of various etiologies, including the following conditions and diseases: inflammatory disorders, allergic disorders, dermatological disorders, autoimmune disease, lymphatic disorders, pruritis, and immunodeficiency disorders. Diseases, disorders and medical conditions that are mediated by histamine H$_4$ receptor activity include those referred to herein.

Fused pyrimidine compounds have been described in: U.S. Pat. No. 3,706,747 and U.S. Pat. No. 3,755,583, U.S. Pat. Appl. Publ. Nos. US2005/0153989 and US2006/0111416, Intl. Pat. Appl. Publ. WO2005/042500, Intl. Pat. Appl. Publ. WO 2006/050965, and JP06220059. However, there remains a need for potent histamine H$_4$ receptor modulators with desirable pharmaceutical properties. Certain benzofuro- and benzothienopyrimidine derivatives have been found in the context of this invention to have histamine H$_4$ receptor-modulating activity.

SUMMARY OF THE INVENTION

In one aspect the invention relates to chemical entity selected from compounds of the following Formula (I):

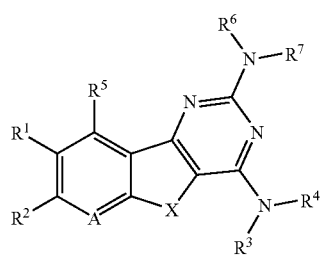

(I)

wherein
$R^1$ and $R^2$ are each independently H, Cl, F, Br, methyl, ethyl, methoxy, $NO_2$, or $CF_3$;
$R^5$ is H, methoxy, Cl, F, Br, or $CF_3$;

A is N or $CR^a$;
  where $R^a$ is H or Cl;
  with the proviso that at least two of $R^1$, $R^2$, $R^5$, and $R^a$ are H;
X is O or S;
—N($R^3$)$R^4$ is one of the moieties:

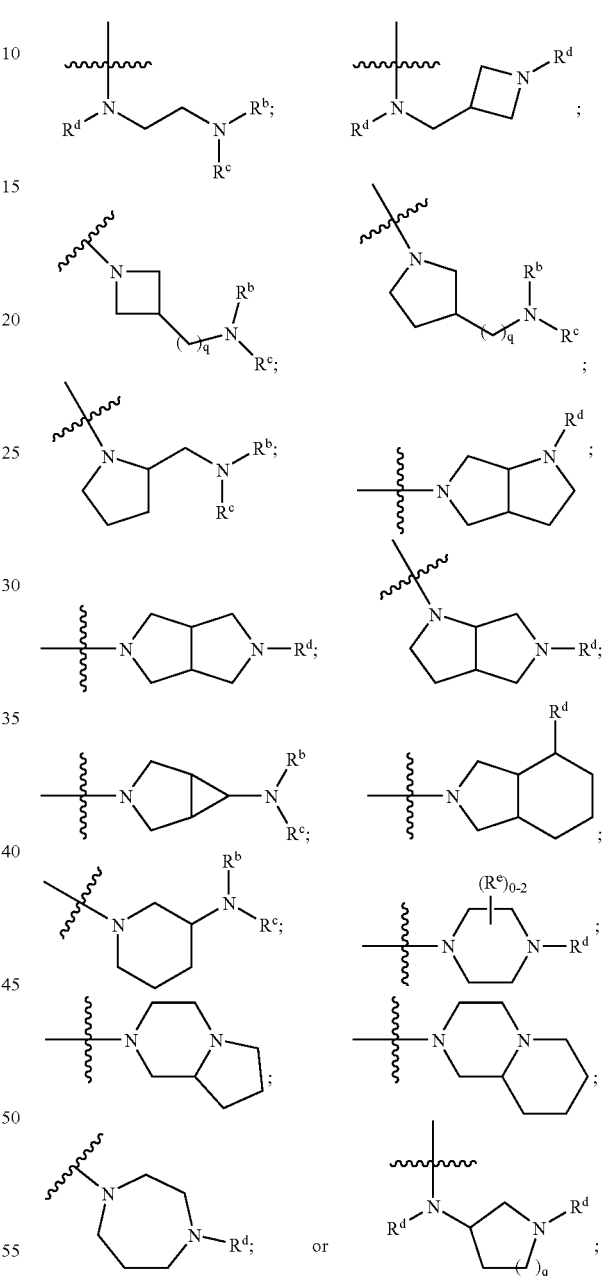

where q is 0 or 1;
$R^3$ and $R^4$ are taken together or separately as defined by the structure of each one of said moieties;
$R^b$, $R^c$, and $R^d$ are each independently H or $C_{1-3}$alkyl; and
  each $R^e$ substitutent is methyl or two $R^e$ substituents taken together form a methylene or ethylene bridge;
$R^6$ is H or methyl;
$R^7$ is H; $C_{1-4}$alkyl unsubstituted or substituted with —OH, —SCH$_3$, or —NH$_2$; allyl; or cyclopropyl;

and pharmaceutically acceptable salts of compounds of Formula (I), pharmaceutically acceptable prodrugs of compounds of Formula (I), and pharmaceutically active metabolites of Formula (I).

In certain embodiments, the compound of Formula (I) is a compound selected from those species described or exemplified in the detailed description below.

In a further aspect, the invention relates to pharmaceutical compositions each comprising an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of Formula (I). Pharmaceutical compositions according to the invention may further comprise a pharmaceutically acceptable excipient.

In another aspect, the invention is directed to a method of treating a subject suffering from or diagnosed with a disease, disorder, or medical condition mediated by histamine $H_4$ receptor activity, comprising administering to the subject in need of such treatment an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I).

In certain preferred embodiments of the inventive method, the disease, disorder, or medical condition is inflammation. Inflammation herein refers to the response that develops as a consequence of histamine release, which in turn is caused by at least one stimulus. Examples of such stimuli are immunological stimuli and non-immunological stimuli.

In another aspect, the invention is directed to a method for modulating histamine $H_4$ receptor activity, comprising exposing histamine $H_4$ receptor to an effective amount of at least one chemical entity selected from compounds of Formula (I) and pharmaceutically acceptable salts of compounds of Formula (I).

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION OF INVENTION AND ITS PREFERRED EMBODIMENTS

For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by a / symbol), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having from 3 to 12 ring atoms per carbocycle.

Illustrative examples of cycloalkyl groups include the following entities, in the form of properly bonded moieties:

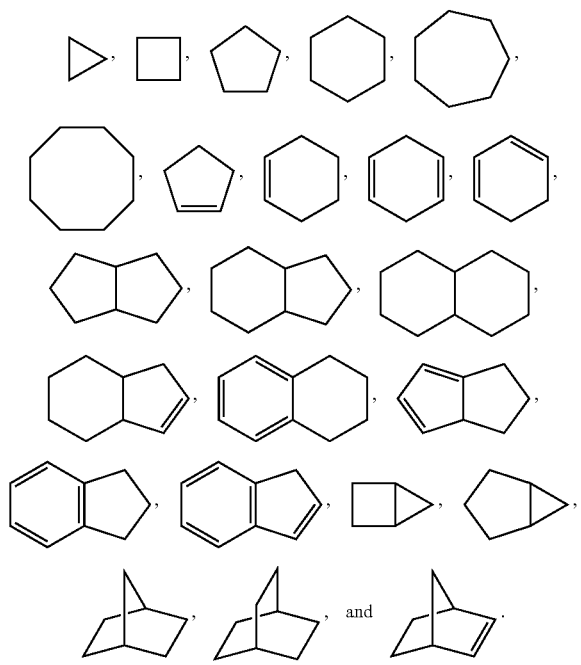

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

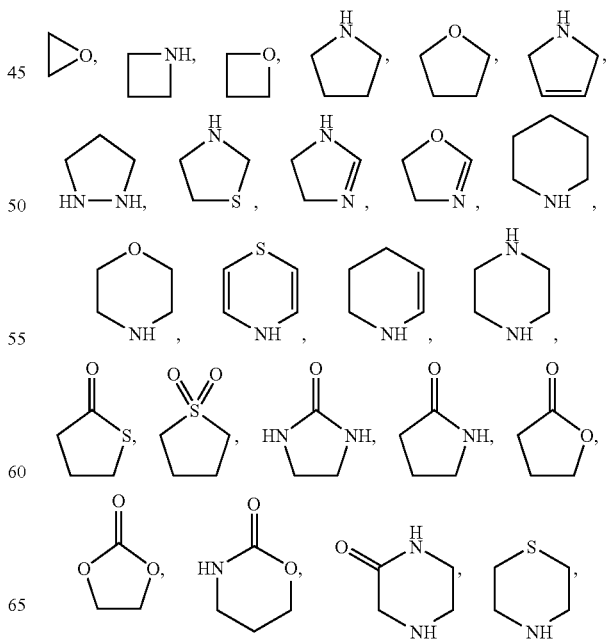

-continued

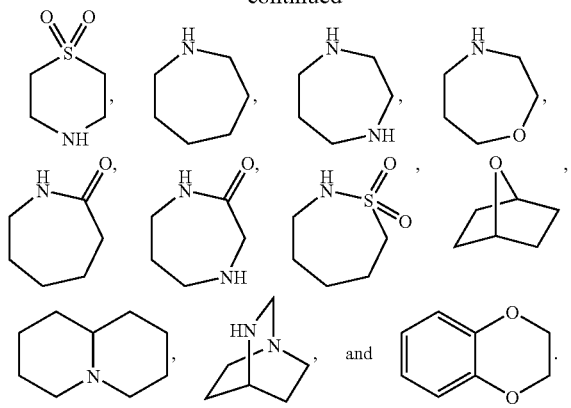

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

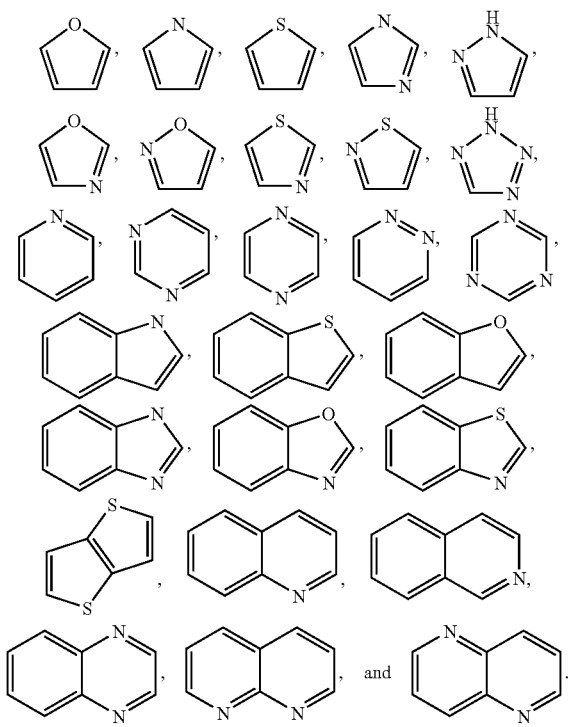

Those skilled in the art will recognize that the species of heteroaryl, cycloalkyl, and heterocycloalkyl groups listed or illustrated above are not exhaustive, and that additional species within the scope of these defined terms may also be selected.

The term "halogen" represents chlorine, fluorine, bromine, or iodine. The term "halo" represents chloro, fluoro, bromo, or iodo.

The term "substituted" means that the specified group or moiety bears one or more substituents. The term "unsubstituted" means that the specified group bears no substituents.

The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to represent hydrates, solvates, and polymorphs of such compounds, and mixtures thereof.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Reference to a chemical entity herein stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively. Such isotopically labelled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$," is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^{1-7}$, A, X, $R^{a-3}$, and q, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^{1-7}$, A, X, $R^{a-e}$, and q, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≦N≦m, with m>n.

Any disubstituent referred to herein is meant to encompass the various attachment possibilities when more than one of such possibilities are allowed. For example, reference to disubstituent —A—B—, where A≠B, refers herein to such disubstituent with A attached to a first substituted member and B attached to a second substituted member, and it also refers to such disubstituent with A attached to the second substituted member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

In some embodiments of Formula (I), $R^1$ is H, methoxy, Cl, Br, F, or $CF_3$.

In some embodiments, $R^2$ is H.

In some embodiments, R is H or $CF_3$.

In some embodiments, A is N. In further embodiments, A is $CR^a$.

In some embodiments, $R^a$ is H.

In some embodiments, X is O. In further embodiments, X is S.

In some embodiments, —N($R^3$)$R^4$ is:

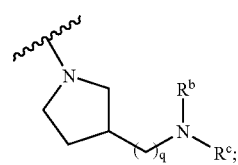

where q is 0 and $R^b$ and $R^c$ are as previously defined. In further embodiments, —N($R^3$)$R^4$ is:

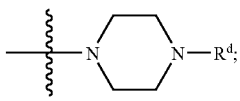

where $R^d$ is as previously defined. In still further embodiments, $—N(R^3)R^4$ is:

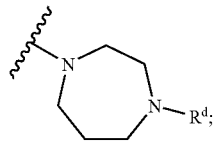

where $R^d$ is as previously defined. In still further embodiments, $—N(R^3)R^4$ is:

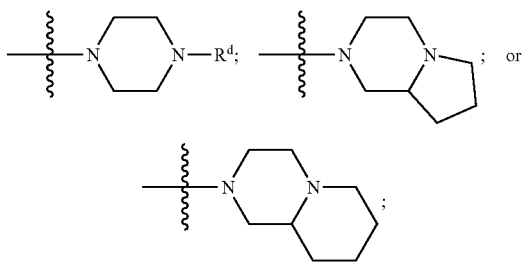

where $R^d$ is as previously defined. In still further embodiments, $—N(R^3)R^4$ is:

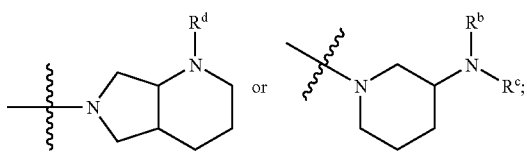

where $R^b$, $R^c$, and $R^d$ are as previously defined. In still further embodiments, $—N(R^3)R^4$ is:

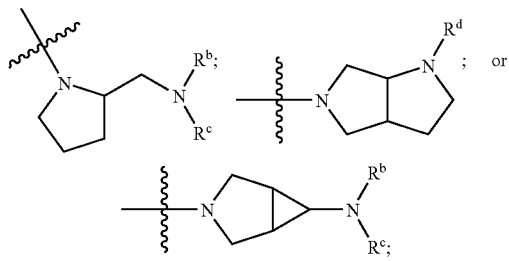

where $R^b$, $R^c$, and $R^d$ are as previously defined. In still further embodiments, $—N(R^3)R^4$ is:

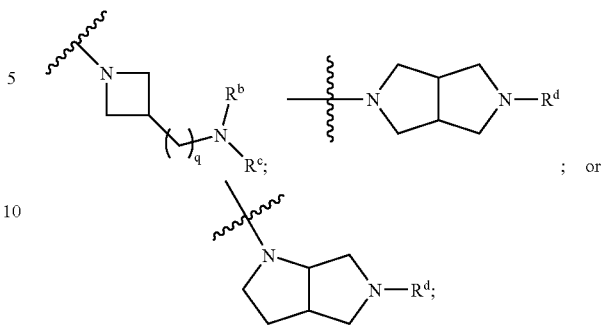

where q, $R^b$, $R^c$, and $R^d$ are as previously defined. In still further embodiments, $—N(R^3)R^4$ is:

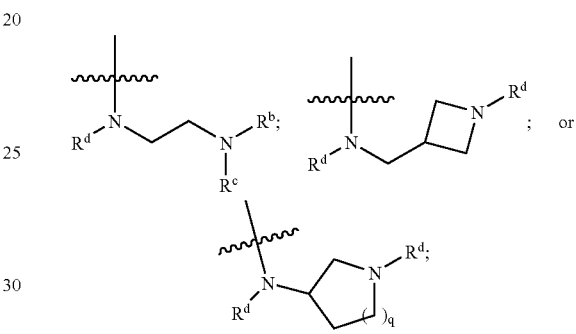

where q and $R^d$ are as previously defined.

In some embodiments, $R^b$, $R^c$, and $R^d$ are each independently H or methyl.

In some embodiments, $R^7$ is H. In other embodiments, $R^7$ is methyl, 2-hydroxyethyl, 2-methanesulfanylethyl, or 2-aminoethyl.

The invention includes also pharmaceutically acceptable salts of the compounds represented by Formula (I), preferably of those described above and of the specific compounds exemplified herein, and methods of treatment using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$ alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

The present invention also relates to pharmaceutically active metabolites of compounds of Formula (I), and uses of such metabolites in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J. Med. Chem.* 1997, 40, 2011-2016; Shan, et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites (collectively, "active agents") of the present invention are useful as histamine $H_4$ receptor modulators in the methods of the invention. The active agents may be used in the inventive methods for the treatment or prevention of medical conditions, diseases, or disorders mediated through modulation of the histamine $H_4$ receptor, such as those described herein. Symptoms or disease states are intended to be included within the scope of "medical conditions, disorders, or diseases."

Accordingly, the invention relates to methods of using the active agents described herein to treat subjects diagnosed with or suffering from a disease, disorder, or condition mediated through histamine $H_4$ receptor activity, such as inflammation. Active agents according to the invention may therefore be used as an anti-inflammatory agents.

In some embodiments, an active agent of the present invention is administered to treat inflammation. Inflammation may be associated with various diseases, disorders, or conditions, such as inflammatory disorders, allergic disorders, dermatological disorders, autoimmune disease, lymphatic disorders, and immunodeficiency disorders, including the more specific conditions and diseases given below. Regarding the onset and evolution of inflammation, inflammatory diseases or inflammation-mediated diseases or conditions include, but are not limited to, acute inflammation, allergic inflammation, and chronic inflammation.

Illustrative types of inflammation treatable with a histamine $H_4$ receptor-modulating agent according to the invention include inflammation due to any one of a plurality of conditions such as allergy, asthma, chronic obstructed pulmonary disease (COPD), atherosclerosis, rheumatoid arthritis, multiple sclerosis, inflammatory bowel diseases (including colitis, Crohn's disease, and ulcerative colitis), psoriasis, pruritis, itchy skin, atopic dermatitis, urticaria (hives), ocular inflammation (e.g., post-surgical ocular inflammation), conjunctivitis, dry eye, nasal polyps, allergic rhinitis, nasal itch, scleroderma, autoimmune thyroid diseases, immune-mediated (also known as type 1) diabetes mellitus and lupus, which are characterized by excessive or prolonged inflammation at some stage of the disease. Other autoimmune diseases that lead to inflammation include Myasthenia gravis, autoimmune neuropathies, such as Guillain-Barré, autoimmune uveitis, autoimmune hemolytic anemia, pernicious anemia, autoimmune thrombocytopenia, temporal arteritis, anti-phospholipid syndrome, vasculitides, such as Wegener's granulomatosis, Behcet's disease, dermatitis herpetiformis, pemphigus vulgaris, vitiligio, primary biliary cirrhosis, autoimmune hepatitis, autoimmune oophoritis and orchitis, autoimmune disease of the adrenal gland, polymyositis, dermatomyositis, spondyloarthropathies, such as ankylosing spondylitis, and Sjogren's syndrome.

Pruritis treatable with a histamine $H_4$ receptor-modulating agent according to the invention includes that which is a symptom of allergic cutaneous diseases (such as atopic dermatitis and hives) and other metabolic disorders (such as chronic renal failure, hepatic cholestasis, and diabetes mellitus).

In other embodiments, an active agent of the present invention is administered to treat allergy, asthma, autoimmune diseases, or pruritis.

Thus, the active agents may be used to treat subjects diagnosed with or suffering from a disease, disorder, or condition mediated through histamine $H_4$ receptor activity. The term "treat" or "treating" as used herein is intended to refer to administration of an active agent or composition of the invention to a subject for the purpose of effecting a therapeutic or prophylactic benefit through modulation of histamine $H_4$ receptor activity. Treating includes reversing, ameliorating, alleviating, inhibiting the progress of, lessening the severity of, or preventing a disease, disorder, or condition, or one or more symptoms of such disease, disorder or condition mediated through modulation of histamine $H_4$ receptor activity. The term "subject" refers to a mammalian patient in need of such treatment, such as a human. "Modulators" include both inhibitors and activators, where "inhibitors" refer to compounds that decrease, prevent, inactivate, desensitize or down-regulate histamine $H_4$ receptor expression or activity, and "activators" are compounds that increase, activate, facilitate, sensitize, or up-regulate histamine $H_4$ receptor expression or activity.

In treatment methods according to the invention, an effective amount of at least one active agent according to the invention is administered to a subject suffering from or diagnosed as having such a disease, disorder, or condition. "Therapeutically effective amount" or "effective amount" and grammatically related terms mean that amount of active compound or pharmaceutical agent that elicits the biological or medicinal response in an in vitro system, a tissue system, an animal or human being, that is being sought by a researcher, veterinarian, medical doctor, or other clinician, where the medicinal response includes, but is not limited to, alleviation of the symptoms of the disease or disorder being treated. Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.001 to about 200 mg of active agent per kg of subject's body weight per day, preferably about 0.05 to 100 mg/kg/day, or about 1 to 35 mg/kg/day, or about 0.1 to 10 mg/kg daily in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of Formula (I) or included with such an agent in a pharmaceutical composition according to the invention. In an exemplary embodiment, additional active ingredients are those that are known or discovered to be effective in the treatment of conditions, disorders, or diseases mediated by histamine $H_4$ receptor activity, such as another histamine $H_4$ receptor modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the active agent according to the invention.

When referring to modulating the target receptor, an "effective amount" means an amount sufficient to affect the activity of such receptor. Measuring the activity of the target receptor may be performed by routine analytical methods. Target receptor modulation is useful in a variety of settings, including assays.

The active agents of the invention are used, alone or in combination with one or more additional active ingredients, to formulate pharmaceutical compositions of the invention. A pharmaceutical composition of the invention comprises an effective amount of at least one active agent in accordance with the invention. In some embodiments, pharmaceutical compositions according to the invention further comprise a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the active agents of the invention can be provided in the form of tablets or capsules, or as a solution, emulsion, or suspension. To prepare the oral compositions, the active agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I).

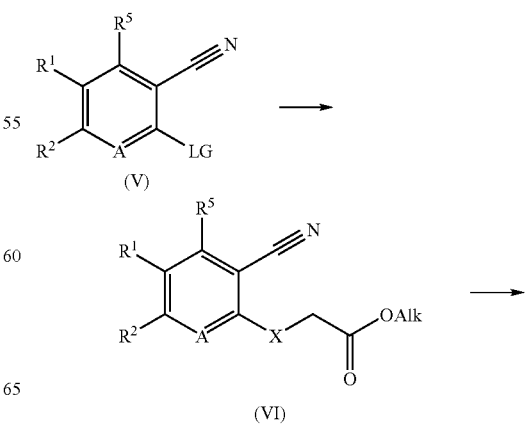

-continued

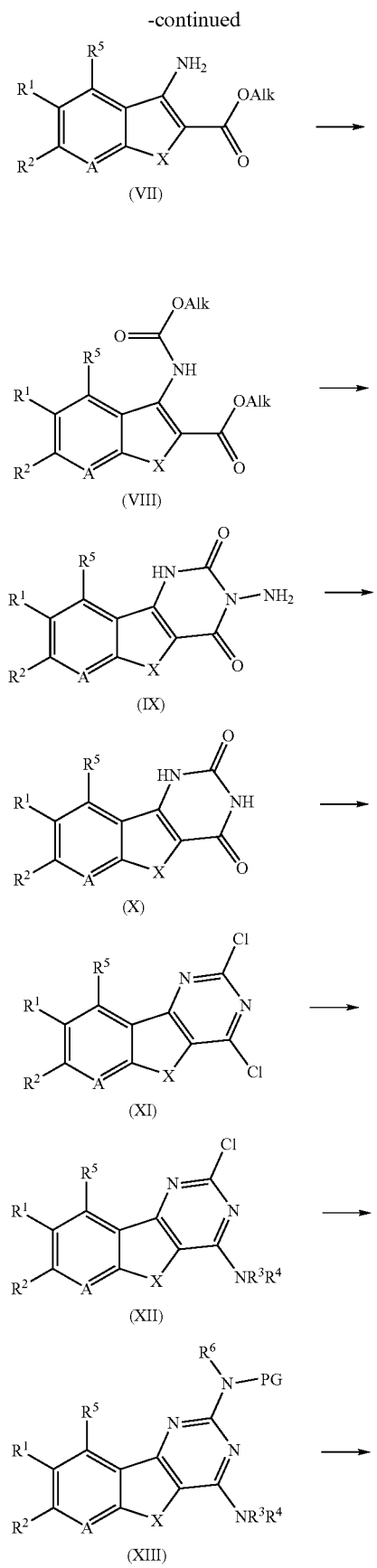

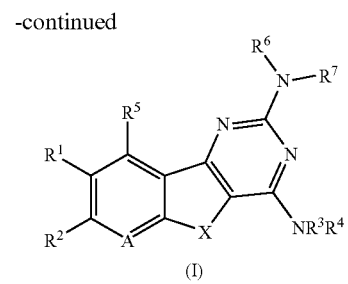

Compounds of Formula (I) may be prepared according to Scheme A. Substituted nitriles (V), where LG is OH (Va) or F (Vb), are commercially available or are generated using methods known in the art. For nitriles (Va), reaction with haloacetic acid esters (Alk is $C_{1-3}$alkyl), such as ethyl bromoacetate, in a solvent such as acetone, in the presence of a suitable base, such as $K_2CO_3$, $Na_2CO_3$, or NaH, provides ethers (VI). Heating ethers (VI) in a solvent such as DMF or DME, or a mixture thereof, in the presence of a suitable base, such as $K_2CO_3$, with heating, provides esters (VII). Fluoronitriles (Vb) as converted directly into esters (VII) by reaction with hydroxy- or mercapto-acetic acid esters (Alk is $C_{1-3}$alkyl), in a solvent such as DMF or DME, or a mixture thereof, in the presence of a suitable base, such as $K_2CO_3$, with heating. Reaction of compounds (VII) with (Alk)chloroformates (Alk is $C_{1-3}$alkyl), such as ethyl chloroformate, in a solvent such as benzene or toluene, or a mixture thereof, with heating, gives carbamates (VIII). Carbamates (VIII) are reacted with hydrazine, in a solvent such as ethanol or isopropanol, or a mixture thereof, to give amino-pyrimidine-diones (IX), which are de-aminated with $NaNO_2$ in a solvent such as acetic acid or water, or a mixture thereof, to give pyrimidine-diones (X). Chlorination using standard methods, such as $POCl_3$ in a solvent such as diethylaniline or dimethylaniline, with heating, gives dichloropyrimidines (XI). Displacement of the 4-chloro substituent with amines, $HN(R^3)R^4$, is accomplished in a solvent such as ethanol, isopropanol, or t-butanol, or a mixture thereof, in the presence of a suitable base, such as $K_2CO_3$ or $Na_2CO_3$ to give amines (XII). One skilled in the art will recognize that diamines $HN(R^3)R^4$ may be suitably protected, and the protecting group removed later in the sequence. Displacement of the 2-chlorosubstituent is performed with protected amine, $HN(R^6)PG$, where PG is $R^7$ or an alkyl protecting group (preferably, benzyl or p-methoxybenzyl), in a solvent such as pyridine, with heating and optionally using microwave irradiation, gives diamines (XIII). Subsequent deprotection of PG (as well as any protecting group on diamines $—N(R^3)R^4$, such as a Boc group) using methods known in the art, provides compounds of Formula (I).

SCHEME B

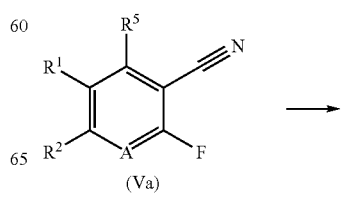

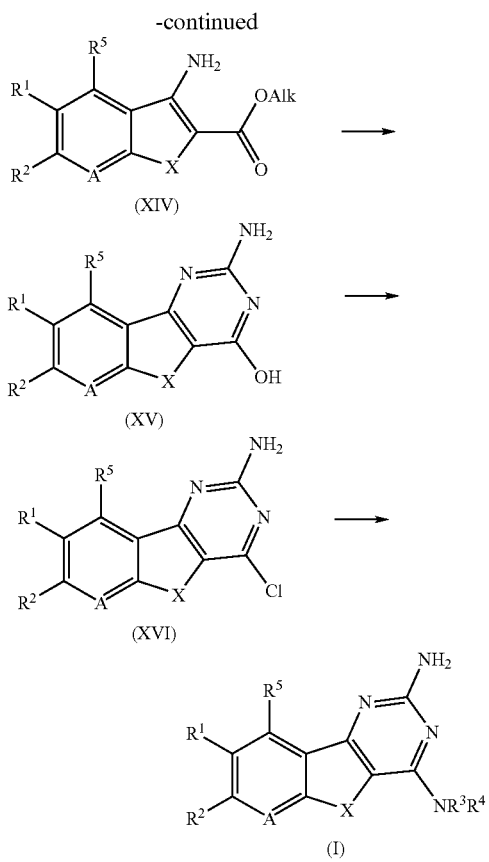

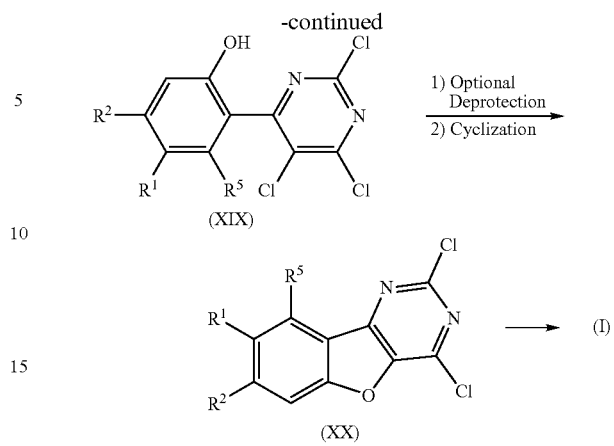

Certain compounds of Formula (I) where X is O and A is CH are also prepared according to Scheme C. Commercially available 2,4,5,6-tetrachloro-pyrimidine (XVII) is reacted with a boronic acid of formula (XVIII), or a suitably protected derivative thereof, in the presence of a palladium catalyst to provide a compound of formula (XIX). Suitable protecting groups include those known in the art, and preferred protecting groups include methyl, methoxymethyl, trialkylsilyl, benzyl, p-methoxybenzyl, or the like. In a preferred embodiment, reaction conditions include treatment with a palladium catalyst such as $Pd(OAc)_2$, a ligand such as $PPh_3$, and a base such as $K_3PO_4$, in a polar solvent such as a $CH_3CN/H_2O$ mixture. Where a suitably protected compound of formula (XIX) is formed, deprotection under conditions known in the art provides compounds of phenols (XIX). By way of example, where the compound is protected with a methyl group, deprotection may be effected with $BBr_3$ in $CH_2Cl_2$. Ullman-type intramolecular cyclization reaction effects a conversion of a compound of formula (XIX) to a dichloro-pyrimidine compound of formula (XX). Preferably, the reaction is performed in the presence to a copper(I) catalyst (such as copper(I) thiophene-2-carboxylate (CuTC)), with or without added base, in a solvent such as N-methylpyrrolidine. Compounds (XX) are converted into compounds of Formula (I) as described in Scheme A. One skilled in the art will recognize that compounds of formula (XX) are also compounds of formula (XI). In a particular embodiment, the compound of formula (XX) is 2,4,8-trichloro-benzo[4,5]furo[3,2-d]pyrimidine.

Compounds of Formula (I) are also prepared according to Scheme B. Fluoronitriles (Va) are reacted with (Alk)thioglycolates (Alk is $C_{1-3}$alkyl), such as methylthioglycolate, in a solvent such as DMF or DME, or a mixture thereof, in the presence of a suitable base such as KOtBu, NaOtBu, or NaH, to give benzothiophenes or benzofurans (XIV) in one step. Condensation with chloroformamidine hydrochloride in a high-boiling solvent such as diglyme, with heating, gives hydroxy-pyrimidines (XV) as the hydrochloride salts. Chlorination with a reagent such as $POCl_3$ in a solvent such as dimethylaniline or diethylaniline, with heating, gives aminopyrimidines (XVI). Displacement of the 4-chloro substituent with amines, $HN(R^3)R^4$, is accomplished in a solvent such as EtOH or pyridine, to provide compounds of Formula (I). Alkylation or reductive amination methods provide compounds of Formula (I) where $R^7$ is not H.

Compounds of Formula (I) may be converted to their corresponding salts using methods described in the art. For example, amines of Formula (I) may be treated with trifluoroacetic acid, HCl, or citric acid in a solvent such as $Et_2O$, $CH_2Cl_2$, THF, and MeOH to provide the corresponding salt forms.

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereo-

SCHEME C

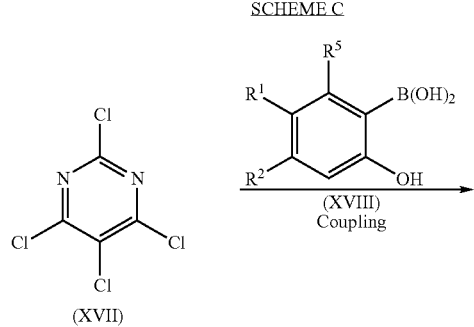

meric mixtures are obtained, single isomers may be separated using conventional methods such as chromatography or crystallization.

The following specific examples are provided to further illustrate the invention and various preferred embodiments.

EXAMPLES

Chemistry

In obtaining the compounds described in the examples below and the corresponding analytical data, the following experimental and analytical protocols were followed unless otherwise indicated.

Unless otherwise stated, reaction mixtures were magnetically stirred at room temperature (rt). Where solutions are "dried," they are generally dried over a drying agent such as $Na_2SO_4$ or $MgSO_4$. Where mixtures, solutions, and extracts were "concentrated", they were typically concentrated on a rotary evaporator under reduced pressure.

Normal-phase flash column chromatography (FCC) was performed on silica gel ($SiO_2$) eluting with 2 M $NH_3$ in MeOH/DCM, unless otherwise noted.

Trifluoroacetic acid salts were obtained by purification of the crude products by reversed-phase HPLC under acidic conditions. Reversed-phase HPLC (acidic conditions) was performed by: 1) a Hewlett Packard HPLC Series 1100 with a Phenomenex Luna C18 (5 μm, 4.6×150 mm) column, detection at λ=230, 254 and 280 nm, and a gradient of 10 to 99% acetonitrile/water (0.05% trifluoroacetic acid) over 5.0 min with a flow rate of 1 mL/min; or 2) a Shimadzu LC-8A equipped with a YMC Pack ODS 250×30 mm column with a gradient of 10 to 50% TFA in acetonitrile and 0.05% in water over 15 min at a rate of 70 mL/min.

Alternatively, purification by reversed-phase HPLC (basic conditions) provided free bases. Reversed-phase HPLC (basic conditions) was performed on a Dionex APS2000 LC/MS with a Phenomenex Gemini C18 (5 μm, 30×100 mm) column, and a gradient of 5 to 100% acetonitrile/water (20 mM $NH_4OH$) over 16.3 min, and a flow rate of 30 mL/min.

Citric acid salts were obtained from the corresponding free bases by the following procedure: A solution of the free base (1 equiv.) in MeOH (0.035 M) was treated with citric acid (0.1 M in MeOH; 1.0 equiv.). The resulting solution was stirred at rt for 2 h and concentrated to provide the desired salt.

Hydrochloride salts were prepared by treating a solution of the free base in $CHCl_3$ with a HCl (1 M in $Et_2O$). Concentration of the reaction mixture provided the hydrochloride salts.

Mass spectra (MS) were obtained on an Agilent series 1100 MSD using electrospray ionization (ESI) in positive mode unless otherwise indicated. The MS data presented is the m/z found (typically [M+H]$^+$) for the molecular ion.

Nuclear magnetic resonance (NMR) spectra were obtained on Bruker model DRX spectrometers. The format of the $^1$H NMR data below is: chemical shift in ppm downfield of the tetramethylsilane reference (multiplicity, coupling constant J in Hz, integration).

Chemical names were generated using ChemDraw Version 6.0.2 (CambridgeSoft, Cambridge, Mass.) or ACD/Name Version 9 (Advanced Chemistry Development, Toronto, Ontario, Canada).

Example 1

8-Chloro-4-(4-methyl-piperazin-1-yl)-benzo[4,5] furo[3,2-d]pyrimidin-2-ylamine

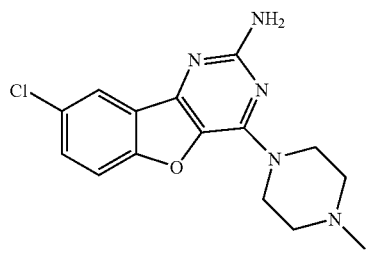

Step A: (4-Chloro-2-cyano-phenoxy)-acetic acid ethyl ester. To a solution of 5-chloro-2-hydroxy-benzonitrile (10 g, 65.0 mmol) in acetone (100 mL) was added ethylbromoacetate (11 g, 71.4 mmol) followed by $K_2CO_3$ (19.7 g, 143 mmol). After heating at reflux for 10 h, the mixture was filtered and the filtrate was concentrated to afford the desired product (15.3 g), which was used in the next step without further purification. $^1$H NMR ($CDCl_3$): 7.57 (d, J=2.5 Hz, 1H), 7.48 (dd, J=9.0, 2.5 Hz, 1H), 6.81 (d, J=9.0 Hz 1H), 4.78 (s, 2H), 4.28 (q, J=7.1 Hz, 2H), 1.32 (t, J=7.1 Hz, 3H).

Step B: 3-Amino-5-chloro-benzofuran-2-carboxylic acid ethyl ester. To a solution of (4-chloro-2-cyano-phenoxy)-acetic acid ethyl ester (15.3 g, 64.0 mmol) in DMF (150 mL) was added $K_2CO_3$ (14.1 g, 102 mmol). After heating at reflux for 10 h, the reaction mixture was poured into ice water. The crude product was collected by filtration as a brown solid (14.37 g, 92%). $^1$H NMR ($CDCl_3$): 7.54 (s, 1H), 7.41-7.27 (m, 2H), 4.94 (s, 2H), 4.44 (q, J=7.1 Hz, 2H), 1.44 (t, J=7.1 Hz, 3H).

Step C: 5-Chloro-3-ethoxycarbonylamino-benzofuran-2-carboxylic acid ethyl ester. To a solution of 3-amino-5-chloro-benzofuran-2-carboxylic acid ethyl ester (2.8 g, 11.7 mmol) in benzene (35 mL) was added ethyl chloroformate (1.3 mL, 14.0 mmol) followed by $K_2CO_3$ (4.5 g, 35.1 mmol). After heating at reflux for 14 h, the mixture was filtered, washing with benzene. The filtrate was concentrated to afford the desired product (100%), which was used in the next step without further purification. $^1$H NMR ($CDCl_3$): 8.69 (s, 1H), 8.45 (s, 1H), 7.47-7.39 (m, 2H), 4.48 (q, J=7.1 Hz, 2H), 4.30 (q, J=7.1 Hz, 2H), 1.55 (t, J=7.1 Hz, 3H), 1.35 (t, J=7.1 Hz, 3H).

Step D: 3-Amino-8-chloro-1H-benzo[4,5]furo[3,2-d]pyrimidine-2,4-dione. To a solution of 5-chloro-3-ethoxycarbonylamino-benzofuran-2-carboxylic acid ethyl ester (3.6 g, 11.6 mmol) in ethanol (50 mL) was added hydrazine hydrate (6.2 mL, 127 mmol). After heating at reflux for 4 h, the title compound was collected by filtration (2.9 g) and was used in the next step without further purification.

Step E: 8-Chloro-1H-benzo[4,5]furo[3,2-d]pyrimidine-2,4-dione. To a suspension of 3-amino-8-chloro-1H-benzo[4,5]furo[3,2-d]pyrimidine-2,4-dione (2.9 g, 11.6 mmol) in 1:1 mixture of acetic acid/$H_2O$ (200 mL) was added $NaNO_2$ (2.5 g, 36.0 mmol). The reaction mixture was heated at 45-50° C. until the evolution of brown fumes ceased (2 h). The product was collected by filtration to afford 2.45 g (89%) of the desired product.

Step F: 2,4,8-Trichloro-benzo[4,5]furo[3,2-d]pyrimidine. To a solution of 8-chloro-1H-benzo[4,5]furo[3,2-d]pyrimidine-2,4-dione (1.0 g, 4.2 mmol) in $PCl_3$ (2.5 mL was added diethylaniline (0.25 mL). After 12 h at 100° C., the reaction mixture was poured into ice water. The crude product was collected by filtration as a brown solid (1 g, 87%) and was used in the next step without further purification.

Step G: 2,8-Dichloro-4-(4-methyl-piperazin-1-yl)-benzo[4,5]furo[3,2-d]pyrimidine. To a solution of 2,4,8-trichloro-benzo[4,5]furo[3,2-d]pyrimidine (1.0 g, 4.8 mmol) in ethanol (15 mL) was added $K_2CO_3$ (1.3 g, 9.6 mmol) followed by N-methylpiperazine (0.532 mL, 4.8 mmol). After 2 h, the reaction mixture was diluted with 1 N NaOH (30 mL) and extracted with $CH_2Cl_2$ (3×20 mL). The combined organic layers were washed with 1 N NaOH (20 mL), dried, and concentrated to afford the desired product (1.03 g, 77%). $^1H$ NMR (CDCl$_3$): 8.10 (s, 1H), 7.55-7.49 (m, 2H), 4.13-4.11 (m, 4H), 2.59-2.56 (m, 4H), 2.36 (s, 3H).

Step H. To a solution of 2,8-dichloro-4-(4-methyl-piperazin-1-yl)-benzo[4,5]furo[3,2-d]pyrimidine (1.3 g, 3.0 mmol) in pyridine (4 mL) was added 4-methoxybenzylamine (4 mL, 30 mmol). After heating at 200° C. for 1 h in the microwave, the resulting mixture was concentrated and the residue was purified by FCC (CH$_2$Cl$_2$/MeOH) to give [8-chloro-4-(4-methyl-piperazin-1-yl)-benzo[4,5]furo[3,2-d]pyrimidin-2-yl]-(4-methoxy-benzyl)-amine. The intermediate was then dissolved in TFA (7 mL) and heated at 65° C. for 3 h. The mixture was diluted with CH$_2$Cl$_2$ (20 mL) and H$_2$O (20 mL). The product was extracted with CH$_2$Cl$_2$ (2×20 mL). The combined organic layers were washed with 1 N NaOH (20 mL), dried, and concentrated. The residue was purified by reverse-phase chromatography to afford the desired product (523 mg, 55%). MS: 318.1. $^1H$ NMR (CDCl$_3$): 7.99 (d, J=1.99 Hz, 1H), 7.48-7.47 (m, 2H), 4.76 (s, 2H), 4.08-4.06 (m, 4H), 2.57-2.55 (m, 4H), 2.37 (s, 3H).

Intermediate 1:
2,4,8-Trichloro-benzo[4,5]furo[3,2-d]pyrimidine (Alternative Preparation)

Step A: 2,4,5-Trichloro-6-(5-chloro-2-methoxy-phenyl)-pyrimidine. In a 250 mL three-neck flask fitted with a degassing tube and temperature probe, acetonitrile (100 mL) and water (25 mL) were degassed with N$_2$ for 30 min while stirring. 2,4,5,6-Tetrachloropyrimidine (8.77 g, 0.0402 mol, 1.5 equiv) and triphenylphosphine (0.70 g, 2.6 mmol, 0.1 equiv) were added and the resulting mixture was degassed for 15 min. 5-Chloro-2-methoxy-phenylboronic acid (5.00 g, 0.0268 mol, 1.0 equiv), K$_3$PO$_4$ (11.39 g, 0.0536 mol, 2.0 equiv) and palladium acetate (301 mg, 1.3 mmol, 0.05 equiv) were added and the resulting mixture was degassed for 5 min. After 2 h at rt, the reaction mixture was poured into CH$_2$Cl$_2$ (250 mL) and washed twice with water (125 mL). The organic layer was dried and concentrated. The crude product was purified by FCC to give a white solid (5.97 g, 69%). MS (ESI$^+$): mass calcd. for C$_{11}$H$_7$Cl$_4$N$_2$O, 322.9; m/z found, 323.0 [M+H]$^+$. $^1H$ NMR (CDCl$_3$): 7.45 (dd, J=8.9, 2.6 Hz, 1H), 7.31 (d, J=2.6 Hz, 1H), 6.94 (d, J=8.9 Hz, 1H), 3.82 (s, 3H).

Step B: 4-Chloro-2-(2,5,6-trichloro-pyrimidin-4-yl)-phenol. A 250 mL 2-neck flask fitted with a rubber septum, temperature probe, and addition funnel was charged with 2,4,5-trichloro-6-(5-chloro-2-methoxy-phenyl)-pyrimidine (5.97 g, 18.54 mmol) and CH$_2$Cl$_2$ (90 mL) and kept under a N$_2$ atmosphere. BBr$_3$ (1 M in CH$_2$Cl$_2$; 37.1 mL, 37.1 mmol, 2 equiv.) was added slowly via addition funnel so that the temperature never exceeded 25° C. After 1 h, water (90 mL) was added and the mixture stirred for approximately 30 min. The organic layer was washed with satd. aq. NaHCO$_3$, dried, and concentrated to give a yellow powder (5.6 g, 98%). MS (ESI$^+$): mass calcd. for C$_{10}$H$_5$Cl$_4$N$_2$O, 308.9; m/z found, 308.9 [M+H]$^+$. $^1H$ NMR (CDCl$_3$): 9.76 (s, 1H), 8.00 (d, J=2.6 Hz, 1H), 7.39 (dd, J=8.9, 2.6 Hz, 1H), 7.03 (d, J=8.9 Hz, 1H).

Step C: 2,4,8-Trichloro-benzo[4,5]furo[3,2-d]pyrimidine. A 10 mL flask was charged with 4-chloro-2-(2,5,6-trichloro-pyrimidin-4-yl)-phenol (75 mg, 0.24 mmol) and N-methylpyrrolidinone (3.0 mL) under a N$_2$ atmosphere. The solution was purged with N$_2$ for, 10 min. Copper (I) thiophene-2-carboxylate (60 mg, 0.32 mmol, 1.3 equiv.) was added and the mixture was heated to 100° C. for 2 h. The reaction mixture was cooled to rt and added to aq. HCl (0.1 M, 6.0 mL) slowly and stirred for 15 min. Additional aq. HCl (0.1 M, 3.0 mL) was added and the mixture was stirred for 20 min. The resulting solid was collected by filtration, rinsed with water, and dried to give a tan solid (55 mg, 83%). GC-MS (CI): mass calcd. for C$_{10}$H$_3$Cl$_3$N$_2$O, 271.9; m/z found, 272.0. $^1H$ NMR (CDCl$_3$): 8.22 (d, J=2.1 Hz, 1H), 7.75 (dd, J=8.9, 2.1 Hz, 1H), 7.69 (d, J=9.0 Hz, 1H).

The compounds in Examples 2-38 were prepared using methods analogous to those described in Example 1.

Example 2

6,8-Dichloro-4-(octahydro-pyrrolo[3,4-b]pyridin-6-yl)-benzo[4.5]furo[3,2-d]pyrimidin-2-ylamine trifluoroacetic acid salt

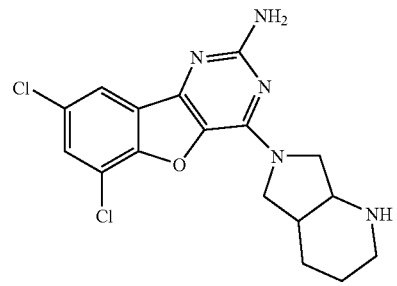

MS: 378.1. $^1H$ NMR (CD$_3$OD): 8.02 (d, J=1.8 Hz, 1H), 7.86 (d, J=1.8 Hz, 1H), 4.63-4.47 (m, 1.5H), 4.27-4.00 (m, 3.5H), 3.84-3.77 (m, 0.5H), 3.47-3.33 (m, 1.5H), 3.17-2.86 (m, 2H), 2.08-1.87 (m, 4H).

Example 3

8-Chloro-4-(4-isopropyl-[1,4]diazepan-1-yl)-benzo[4,5]furo[3,2-d]pyrimidin-2-ylamine trifluoroacetic acid salt

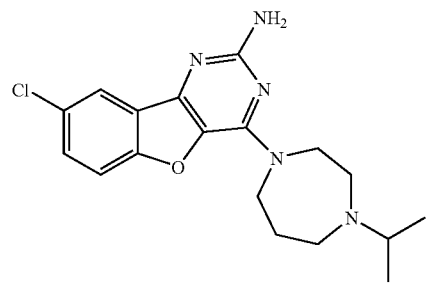

MS: 360.2. ¹H NMR (CD₃OD): 8.07-8.06 (m, 1H), 7.76-7.72 (m, 2H), 4.71-4.09 (m, 4H), 3.82-3.34 (m, 5H), 2.42-2.28 (m, 2H), 1.37 (d, J=6.6 Hz, 6H).

Example 4

4-(3-Amino-pyrrolidin-1-yl)-6,8-dichloro-benzo[4,5]furo[3,2-d]pyrimidin-2-ylamine trifluoroacetic acid salt

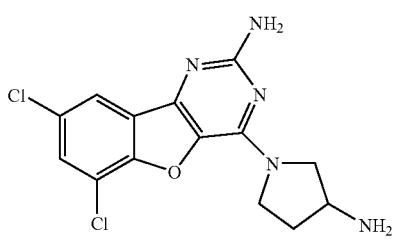

MS: 338.1. ¹H NMR (CD₃OD): 8.02 (d, J=1.8 Hz, 1H), 7.86 (d, J=1.8 Hz, 1H), 4.62-3.97 (m, 5H), 2.64-2.13 (m, 2H).

Example 5

(R)-6,8-Dichloro-4-(3-methylamino-pyrrolidin-1-yl)-benzo[4,5]furo[3,2-d]pyrimidin-2-ylamine trifluoroacetic acid salt

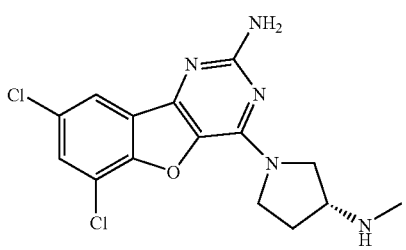

MS: 352.1. ¹H NMR (CD₃OD): 8.02 (d, J=1.8 Hz, 1H), 7.86 (d, J=1.8 Hz, 1H), 4.65-3.88 (m, 5H), 2.84 (s, 3H), 2.64-2.23 (m, 2H).

Example 6

(R)-4-(3-Methylamino-pyrrolidin-1-yl)-benzo[4,5]furo[3,2-d]pyrimidin-2-ylamine citric acid salt

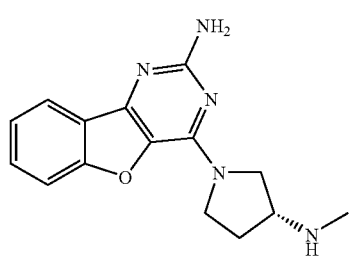

MS: 284.2. ¹H NMR (DMSO-d₆): 7.90 (d, J=7.2 Hz, 1H), 7.68-7.56 (m, 2H), 7.39 (dt, J=1.2, 7.4 Hz, 1H), 6.12 (s, 2H), 4.18-3.82 (m, 5H), 2.64-2.56 (m, 7H), 2.42-2.16 (m, 2H).

Example 7

8-Chloro-4-[1,4]diazepan-1-yl-benzo[4,5]furo[3,2-d]pyrimidin-2-ylamine trifluoroacetic acid salt

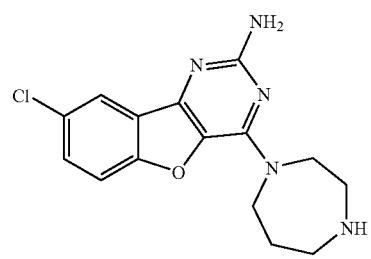

MS: 318.1. ¹H NMR (CD₃OD): 8.07-8.06 (m, 1H), 7.75-7.72 (m, 2H), 4.61-4.08 (m, 4H), 3.62-3.41 (m, 4H), 2.34-2.26 (m, 2H).

Example 8

8-Chloro-4-(octahydro-pyrido[1,2-a]pyrazin-2-yl)-benzo[4,5]furo[3,2-d]pyrimidin-2-ylamine

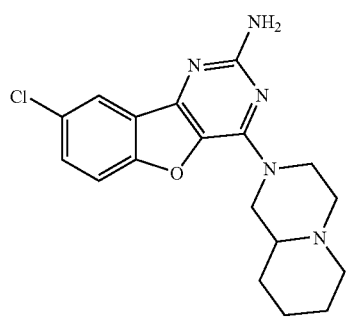

MS: 358.1. ¹H NMR (CDCl₃): 7.99 (d, J=1.9 Hz, 1H), 7.49-7.45 (m, 2H), 4.89-4.77 (m, 1H), 4.75-4.73 (m, 2H), 3.85-3.80 (m, 2H), 3.48-3.45 (m, 1H), 2.91-2.88 (m, 2H), 2.35-2.34 (m, 1H), 2.10-2.07 (m, 2H), 1.74-1.73 (m, 1H), 1.69-1.63 (m, 3H), 1.36-1.34 (m, 2H).

Example 9

8-Chloro-4-(octahydro-pyrrolo[3,4-b]pyridin-6-yl)-benzo[4,5]furo[3,2-d]pyrimidin-2-ylamine

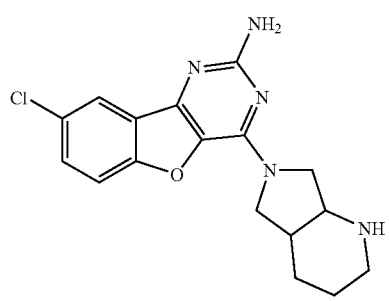

MS: 344.1. ¹H NMR (CDCl₃): 7.94 (d, J=1.9 Hz, 1H), 7.42-7.41 (m, 2H), 4.11-3.97 (m, 2H), 3.79-3.64 (m, 2H), 3.49-3.47 (m, 1H), 3.03-3.00 (m, 1H), 2.70-2.60 (m, 2H), 2.43-2.38 (m, 1H), 1.82-1.53 (m, 4H).

Example 10

8-Chloro-4-(4-methyl-[1,4]diazepan-1-yl)-benzo[4,5]furo[3,2-d]pyrimidin-2-ylamine

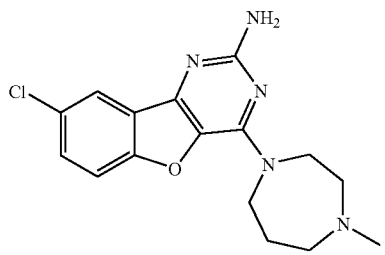

MS: 332.1. ¹H NMR (CDCl₃): 7.99 (d, J=2.5 Hz, 1H), 7.47-7.40 (m, 2H), 4.79 (s, 2H), 4.11-4.08 (m, 4H), 2.81-2.79 (m, 2H), 2.63-2.61 (m, 2H), 2.41 (s, 3H), 2.11-2.06 (m, 2H).

Example 11

(S,S)-8-Chloro-4-(2,5-diaza-bicyclo[2.2.1]hept-2-yl)-benzo[4,5]furo[3,2-d]pyrimidin-2-ylamine

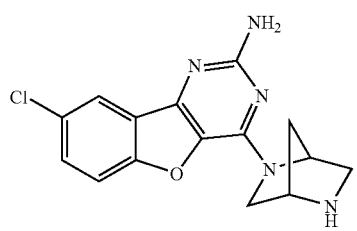

MS: 316.1. ¹H NMR (CDCl₃): 7.99 (d, J=2.5 Hz, 1H), 7.45-7.40 (m, 2H), 4.87-4.84 (m, 2H), 3.91-3.89 (m, 1H), 3.81-3.79 (m, 1H), 3.15-3.11 (m, 2H), 1.98-1.96 (m, 2H).

Example 12

8-Chloro-4-(3-methylamino-pyrrolidin-1-yl)-benzo[4,5]furo[3,2-d]pyrimidin-2-ylamine

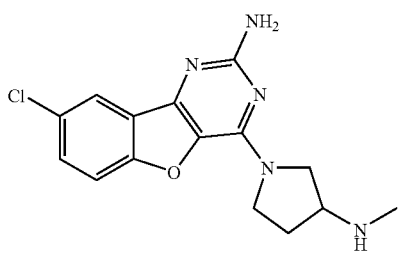

MS: 318.1. ¹H NMR (CD₃OD): 7.99 (d, J=2.5 Hz, 1H), 7.47-7.41 (m, 2H), 4.78-4.75 (m, 2H), 3.95-3.90 (m, 2H), 3.82-3.81 (m, 1H), 3.43-3.41 (m, 1H), 2.53 (s, 3H), 2.24-2.21 (m, 1H), 1.93-1.89 (m, 1H).

Example 13

(S)-4-(3-Amino-piperidin-1-yl)-8-chloro-benzo[4,5]furo[3,2-d]pyrimidin-2-ylamine trifluoroacetic acid salt

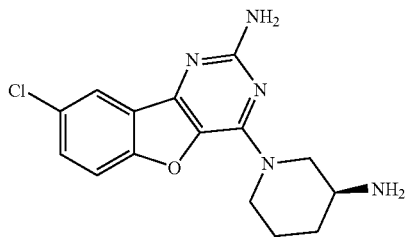

MS: 318.1. ¹H NMR (CD₃OD): 7.99 (d, J=2.5 Hz, 1H), 7.47-7.41 (m, 2H), 4.99-4.97 (m, 1H), 4.81-4.73 (m, 1H), 4.56-4.53 (m, 1H), 3.95-3.90 (m, 1H), 3.56-3.53 (m, 1H), 2.26-2.23 (m, 1H), 2.02-2.00 (m, 1H), 1.90-1.82 (m, 2H).

Example 14

8-Chloro-4-piperazin-1-yl-benzo[4,5]furo[3,2-d]pyrimidin-2-ylamine trifluoroacetic acid salt

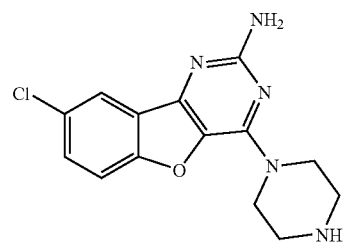

MS: 304.1. ¹H NMR (CD₃OD): 8.00 (d, J=2.5 Hz, 1H), 7.67-7.57 (m, 2H), 4.46-4.44 (m, 4H), 3.44-3.34 (m, 4H).

Example 15

8-Chloro-4-(3-dimethylamino-pyrrolidin-1-yl)-benzo[4,5]furo[3,2-d]pyrimidin-2-ylamine trifluoroacetic acid salt

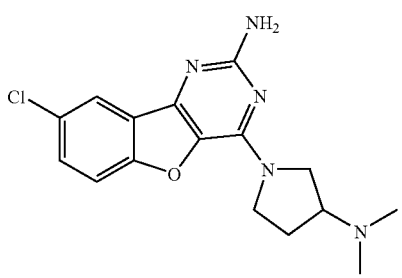

MS: 332.1. ¹H NMR (CD₃OD): 8.05 (d, J=2.5 Hz, 1H), 7.57-7.49 (m, 2H), 4.40-4.30 (m, 2H), 3.97-3.81 (m, 2H), 3.79-3.76 (m, 1H), 2.85 (s, 6H), 2.60-2.51 (m, 2H).

Example 16

4-(3-Amino-pyrrolidin-1-yl)-8-chloro-benzo[4,5]furo[3,2-d]pyrimidin-2-ylamine trifluoroacetic acid salt

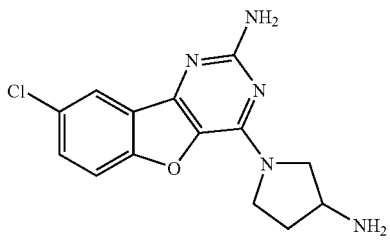

MS: 304.1. ¹H NMR (CD₃OD): 8.05 (d, J=2.5 Hz, 1H), 7.75-7.70 (m, 2H), 4.44-4.05 (m, 5H), 2.68-2.61 (m, 2H).

Example 17

(S)-8-Chloro-4-(3-methylamino-pyrrolidin-1-yl)-benzo[4,5]furo[3,2-d]pyrimidin-2-ylamine

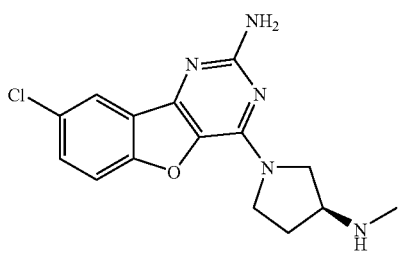

MS: 318.1. ¹H NMR (CDCl₃): 7.99 (d, J=2.5 Hz, 1H), 7.47-7.41 (m, 2H), 4.78-4.75 (m, 2H), 3.95-3.90 (m, 2H), 3.82-3.81 (m, 1H), 3.43-3.41 (m, 1H), 2.53 (s, 3H), 2.24-2.21 (m, 1H), 1.93-1.89 (m, 1H).

Example 18

(R)-8-Chloro-4-(3-methylamino-pyrrolidin-1-yl)-benzo[4,5]furo[3,2-d]pyrimidin-2-ylamine

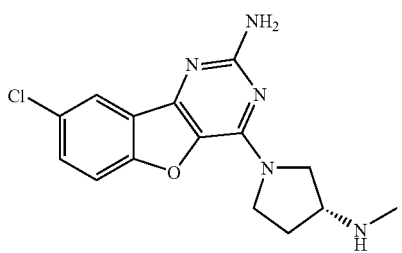

MS: 318.1. ¹H NMR (CDCl₃): 7.99 (d, J=2.5 Hz, 1H), 7.47-7.41 (m, 2H), 4.78-4.75 (m, 2H), 3.95-3.90 (m, 2H), 3.82-3.81 (m, 1H), 3.43-3.41 (m, 1H), 2.53 (s, 3H), 2.24-2.21 (m, 1H), 1.93-1.89 (m, 1H).

Example 19

(R)-8-Bromo-4-(3-methylamino-pyrrolidin-1-yl)-benzo[4,5]furo[3,2-d]pyrimidin-2-ylamine trifluoroacetic acid salt

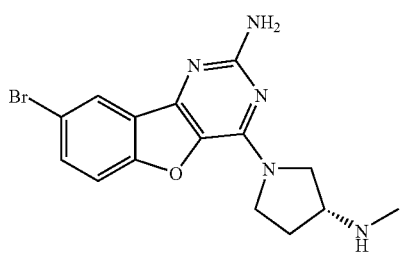

MS: 363.1. ¹H NMR (CDCl₃): 8.16 (d, J=1.9 Hz, 1H), 7.80 (dd, J=9.0, 1.9 Hz, 1H), 7.64 (d, J=9.0 Hz, 1H), 4.41-3.93 (m, 5H), 2.84 (s, 3H), 2.72-2.64 (m, 2H).

Example 20

8-Bromo-4-(hexahydro-pyrrolo[1,2-a]pyrazin-2-yl)-benzo[4,5]furo[3,2-d]pyrimidin-2-ylamine trifluoroacetic acid salt

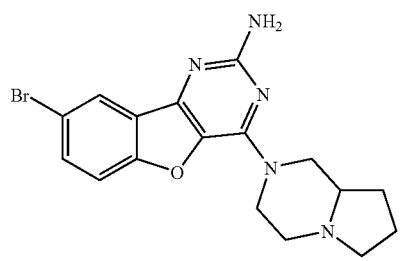

MS: 388.1. ¹H NMR (CDCl₃): 8.20 (d, J=1.9 Hz, 1H), 7.82 (dd, J=1.9, 9.0 Hz, 1H), 7.66 (d, J=9.0 Hz, 1H), 3.92-3.50 (m, 9H), 2.39-1.95 (m, 4H).

Example 21

4-(3-Amino-pyrrolidin-1-yl)-benzo[4,5]furo[3,2-d]pyrimidin-2-ylamine trifluoroacetic acid salt

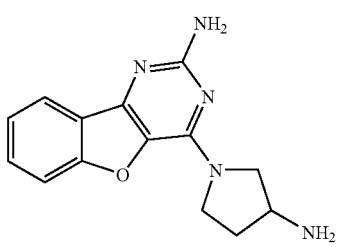

MS: 270.1. ¹H NMR (CD₃OD): 8.05 (d, J=7.8 Hz, 1H), 7.78-7.74 (m, 2H), 7.55-7.52 (m, 1H), 4.62-4.38 (m, 2H), 4.24-3.93 (m, 3H), 2.68-2.20 (m, 2H).

Example 22

(R)-4-(3-Dimethylamino-pyrrolidin-1-yl)-benzo[4,5]furo[3,2-d]pyrimidin-2-ylamine trifluoroacetic acid salt

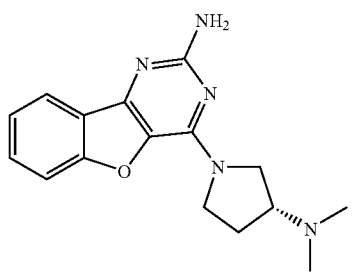

MS: 298.2. ¹H NMR (CD₃OD): 8.04 (d, J=7.8 Hz, 1H), 7.75-7.68 (m, 2H), 7.52-7.50 (m, 1H), 4.60-3.81 (m, 5H), 3.04 (s, 6H), 2.73-2.31 (m, 2H).

Example 23

4-Piperazin-1-yl-benzo[4,5]furo[3,2-d]pyrimidin-2-ylamine trifluoroacetic acid salt

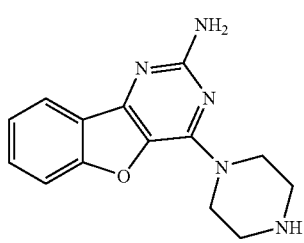

MS: 270.1. ¹H NMR (CD₃OD): 8.07 (d, J=7.8 Hz, 1H), 7.79-7.74 (m, 2H), 7.56-7.53 (m, 1H), 4.54-4.43 (m, 4H), 3.50-3.45 (m, 4H).

Example 24

(R)-8-Chloro-4-(3-dimethylamino-pyrrolidin-1-yl)-benzo[4,5]furo[3,2-d]pyrimidin-2-ylamine trifluoroacetic acid salt

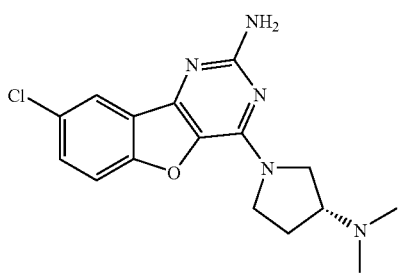

MS: 332.1. ¹H NMR (CD₃OD): 8.02 (s, 1H), 7.72-7.65 (m, 2H), 4.58-3.76 (m, 5H), 3.04 (s, 6H), 2.76-2.28 (m, 2H).

Example 25

(R)-4-(3-Amino-pyrrolidin-1-yl)-8-chloro-benzo[4,5]furo[3,2-d]pyrimidin-2-ylamine trifluoroacetic acid salt

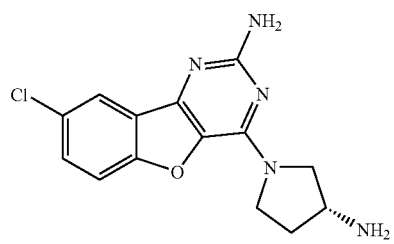

MS: 304.1. ¹H NMR (CD₃OD): 8.06-8.05 (m, 1H), 7.76-7.70 (m, 2H), 4.60-3.88 (m, 5H), 2.68-2.18 (m, 2H).

Example 26

(S)-4-(3-Aminomethyl-pyrrolidin-1-yl)-8-chloro-benzo[4,5]furo[3,2-d]pyrimidin-2-ylamine trifluoroacetic acid salt

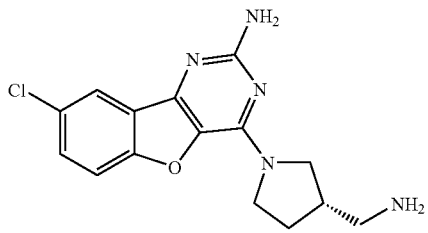

MS: 318.1. ¹H NMR (CD₃OD): 8.03 (s, 1H), 7.75-7.68 (m, 2H), 4.58-4.36 (m, 1H), 4.22-4.01 (m, 1.5H), 3.94-3.72 (m, 1H), 3.59-3.52 (m, 0.5H), 3.22-3.08 (m, 2H), 2.85-2.62 (m, 1H), 2.47-2.24 (m, 1H), 2.04-1.81 (m, 1H).

Example 27

8-Chloro-4-(hexahydro-pyrrolo[3,4-c]pyrrol-2-yl)-benzo[4,5]furo[3,2-d]pyrimidin-2-ylamine trifluoroacetic acid salt

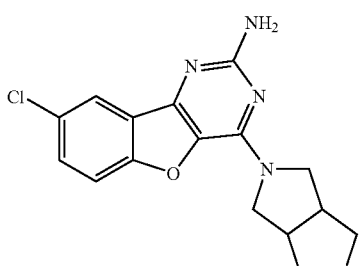

MS: 330.1.

Example 28

(R)-4-(3-Amino-piperidin-1-yl)-8-chloro-benzo[4,5]furo[3,2-d]pyrimidin-2-ylamine trifluoroacetic acid salt

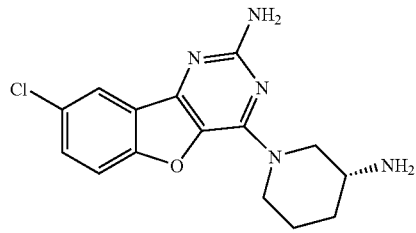

MS: 318.1.

Example 29

4-(3-Aminomethyl-pyrrolidin-1-yl)-8-chloro-benzo[4,5]furo[3,2-d]pyrimidin-2-ylamine trifluoroacetic acid salt

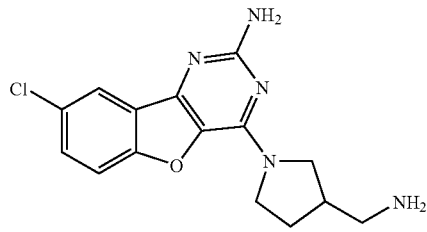

MS: 318.1.

Example 30

(R)-4-(3-Aminomethyl-pyrrolidin-1-yl)-8-chloro-benzo[4,5]furo[3,2-d]pyrimidin-2-ylamine trifluoroacetic acid salt

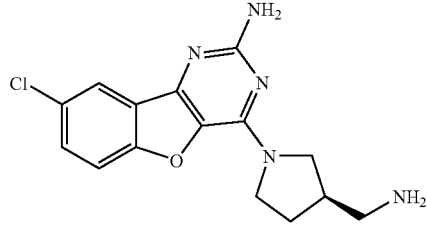

MS: 318.1.

Example 31

6,8-Dichloro-4-piperazin-1-yl-benzo[4,5]furo[3,2-d]pyrimidin-2-ylamine trifluoroacetic acid salt

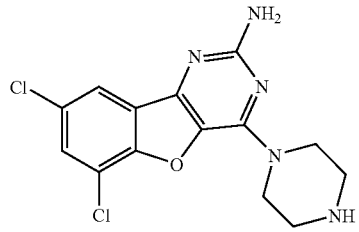

MS: 338.1.

Example 32

6,8-Dichloro-4-[1,4]diazepan-1-yl-benzo[4,5]furo[3,2-d]pyrimidin-2-ylamine trifluoroacetic acid salt

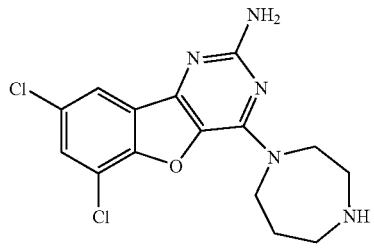

MS: 352.1.

Example 33

(S,S)-4-(2,5-Diaza-bicyclo[2.2.1]hept-2-yl)-benzo[4,5]furo[3,2-d]pyrimidin-2-ylamine trifluoroacetic acid salt

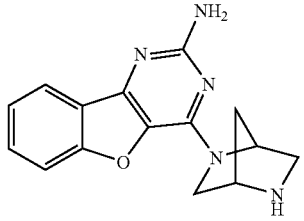

MS: 282.1.

Example 34

8-Chloro-4-(4-isopropyl-piperazin-1-yl)-benzo[4,5]furo[3,2-d]pyrimidin-2-ylamine trifluoroacetic acid salt

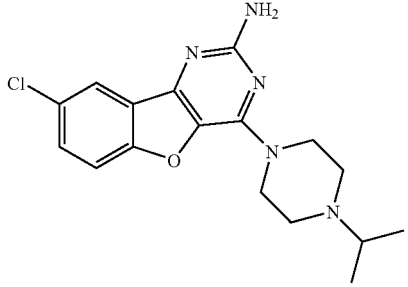

MS: 346.2.

Example 35

6,8-Dichloro-4-(3-dimethylamino-pyrrolidin-1-yl)-benzo[4,5]furo[3,2-d]pyrimidin-2-ylamine trifluoroacetic acid salt

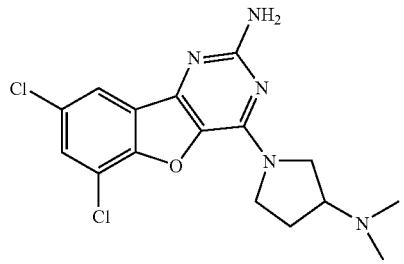

MS: 366.1.

Example 36

4-(Octahydro-pyrido[1,2-a]pyrazin-2-yl)-benzo[4,5]furo[3,2-d]pyrimidin-2-ylamine trifluoroacetic acid salt

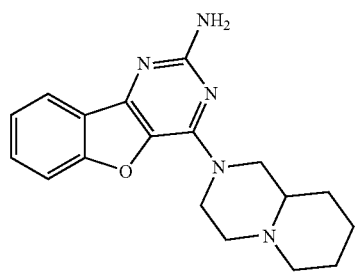

MS: 324.2.

Example 37

6,8-Dichloro-4-(octahydro-pyrido[1,2-a]pyrazin-2-yl)-benzo[4,5]furo[3,2-d]pyrimidin-2-ylamine trifluoroacetic acid salt

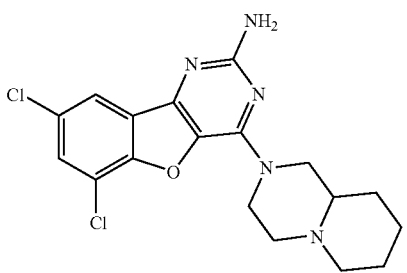

MS: 392.1.

Example 38

(S,S)-6,8-Dichloro-4-(2,5-diaza-bicyclo[2.2.1]hept-2-yl)-benzo[4,5]furo[3,2-d]pyrimidin-2-ylamine trifluoroacetic acid salt

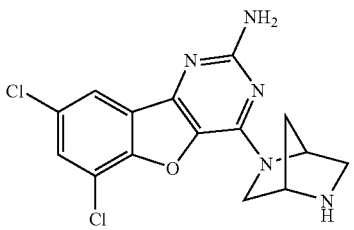

MS: 350.1.

Example 39

(R)-8-Fluoro-4-(3-methylamino-pyrrolidin-1-yl)-benzo[4,5]furo[3,2-d]pyrimidin-2-ylamine trifluoroacetic acid salt

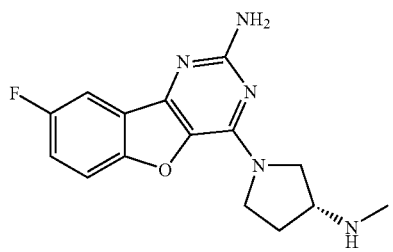

Step A: 3-Amino-5-fluoro-benzofuran-2-carboxylic acid ethyl ester. To a solution of 2,5-difluoro-benzonitrite (10 g, 72.0 mmol) in DMF (200 mL) was added hydroxy-acetic acid ethyl ester (8.6 mL, 86.4 mmol) followed by $K_2CO_3$ (43.7 g, 316 mmol). After 24 h at 100° C., the reaction mixture was diluted with 1 N NaOH (200 mL) and extracted with $CH_2Cl_2$ (3×150 mL). The combined organic layers were washed with 1 N NaOH (100 mL), dried, and concentrated to afford the desired product (3.35 g, 21%). $^1$H NMR ($CDCl_3$): 7.39 (dd, J=9.0, 4.0 Hz, 1H), 7.21-7.15 (m, 2H), 4.90 (s, 2H), 4.45 (q, J=7.1 Hz, 2H), 1.47 (t, J=7.1 Hz, 3H).

Step B. The title compound was prepared from 3-amino-5-fluoro-benzofuran-2-carboxylic acid ethyl ester using methods analogous to those described in Example 1, Steps C-H. MS: 302.2. $^1$H NMR ($CDCl_3$): 7.76-7.73 (m, 2H), 7.53-7.49 (m, 1H), 4.43-3.93 (m, 5H), 2.84 (s, 3H), 2.72-2.64 (m, 2H).

The compounds in Examples 40-43 were prepared using methods analogous to those described in Example 39.

Example 40

8-Fluoro-4-(hexahydro-pyrrolo[1,2-a]pyrazin-2-yl)-benzo[4,5]furo[3,2-d]pyrimidin-2-ylamine trifluoroacetic acid salt

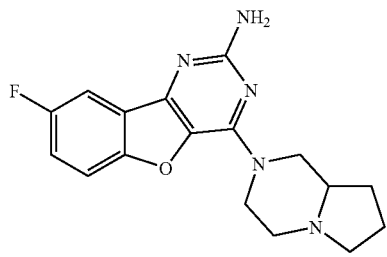

MS: 328.1. ¹H NMR (CDCl₃): 7.76-7.73 (m, 2H), 7.53-7.49 (m, 1H), 3.92-3.50 (m, 9H), 2.39-1.95 (m, 4H).

Example 41

8-Fluoro-N⁴-methyl-N⁴-(1-methyl-pyrrolidin-3-yl)-benzo[4,5]furo[3,2-d]pyrimidine-2,4-diamine trifluoroacetic acid salt

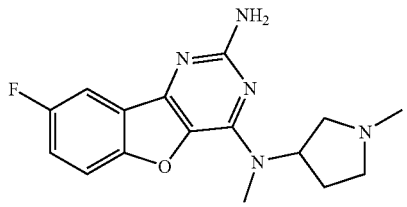

MS: 316.2.

Example 42

(R)-8-(3-Methylamino-pyrrolidin-1-yl)-9-oxa-1,5,7-triaza-fluoren-6-ylamine

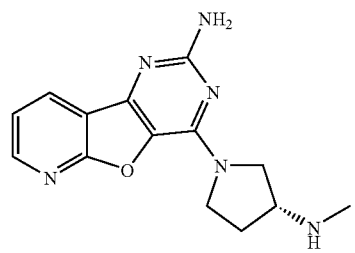

MS: 285.2. ¹H NMR (CDCl₃): 8.50 (dd, J=1.8, 4.8 Hz, 1H), 8.37 (dd, J=1.8, 7.8 Hz, 1H), 7.36-7.34 (m, 1H), 4.77 (s, 2H), 4.30-3.38 (m, 5H), 2.52 (s, 3H), 2.28-2.16 (m, 1H), 1.98-1.86 (m, 1H).

Example 43

8-(Octahydro-pyrrolo[3,4-b]pyridin-6-yl)-9-oxa-1,5,7-triaza-fluoren-6-ylamine

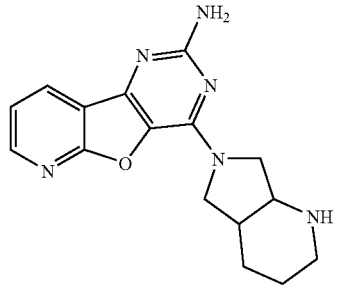

MS: 311.2. ¹H: NMR (CDCl₃): 8.50 (dd, J=1.8, 4.8 Hz, 1H), 8.36 (dd, J=1.8, 7.8 Hz, 1H), 7.36-7.34 (m, 1H), 4.75 (s, 2H), 4.23-4.04 (m, 2H), 3.82-3.62 (m, 2H), 3.54-3.42 (m, 1H), 3.06-3.02 (m, 1H), 2.74-2.67 (m, 1H), 2.48-2.32 (m, 1H), 1.90-1.52 (m, 4H).

Example 44

4-(4-Methyl-piperazin-1-yl)-benzo[4,5]thieno[3,2-d]pyrimidin-2-ylamine

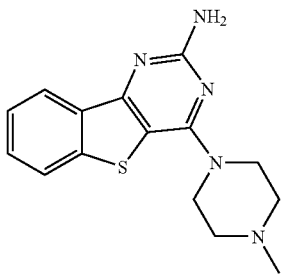

Step A: 3-Amino-benzo[b]thiophene-2-carboxylic acid methyl ester. To a solution of 2-fluorobenzonitrile (9.0 g, 74.3 mmol) and methyl thioglycolate (13.3 mL, 148.6 mmol) in DMF (50 mL) at 0° C. was added potassium tert-butoxide portionwise (16.7 g. 149 mmol) over 15 min with vigorous stirring. The orange solution was warmed to rt and stirred for 1 h before being poured into 700 mL of vigorously stirring ice water. The precipitate was filtered and air-dried to give a pale yellow solid (13.6 g, 88%) that was used without purification. ¹H NMR (CD₃OD): 8.16-8.12 (m, 1H), 7.85-7.82 (m, 1H), 7.54-7.49 (m, 1H), 7.43-7.38 (m, 1H), 7.19 (s, 2H), 3.79 (s, 3H).

Step B: 2-Amino-benzo[4,5]thieno[3,2-d]pyrimidin-4-ol hydrochloride. A suspension of 3-amino-benzo[b]thiophene-2-carboxylic acid methyl ester (1.03 g, 5.0 mmol) and chloroformamidine hydrochloride (800 mg, 7.0 mmol) in diglyme (8 mL) were heated at 160° C. for 1 h. The resulting suspension was cooled to rt and filtered, and the collected solid was suction dried to give the title compound (1.14 g, 90%). ¹H NMR (DMSO-d₆): 8.06 (d, J=7.9 Hz, 1H), 7.89 (d, J=8.1 Hz, 1H), 7.73-7.47 (m, 2H), 7.45-7.39 (m, 1H), 7.38-7.33 (m, 1H), 7.18 (s, 0.6H), 7.05 (s, 0.6H), 6.92 (s, 0.6H).

Step C: 4-Chloro-benzo[4,5]thieno[3,2-d]pyrimidin-2-ylamine. A suspension of 2-amino-benzo[4,5]thieno[3,2-d]pyrimidin-4-ol hydrochloride (179 mg, 0.7 mmol), POCl₃ (1.5 mL), and N,N-dimethylaniline (0.15 mL) was heated at 110° C. for 3 h. The mixture was cooled to rt and the resulting suspension was added dropwise to a 0° C. solution of aq. NH₄OH (19 g/L; 30 mL). The suspension was filtered and the collected solid dried to yield 87 mg (52%) of a crude solid, which was immediately used without purification.

Step D. A solution of crude 4-chloro-benzo[4,5]thieno[3,2-d]pyrimidin-2-ylamine (30 mg, 0.13 mmol) and N-methyl piperizine (0.03 mL, 0.27 mmol) in EtOH was heated at 70° C. for 1 h. The mixture was cooled to rt and concentrated and the crude residue purified by FCC to yield a white solid (9.8 mg, 26%). MS: 300.4. ¹H NMR (CDCl₃): 8.34-8.27 (m, 1H), 7.81-7.75 (m, 1H), 7.57-7.51 (m, 1H), 7.48-7.43 (m, 1H), 4.85 (s, 2H), 3.98 (t, J=4.9 Hz, 4H), 2.56 (t, J=4.9 Hz, 4H), 2.37 (s, 3H).

The compounds in Examples 45-83 were prepared using methods analogous to those described in the preceding examples, with alterations where noted.

Example 45

8-Bromo-4-(octahydro-pyrrolo[3,4-b]pyridin-6-yl)-benzo[4,5]thieno[3,2-d]pyrimidin-2-ylamine hydrochloride salt

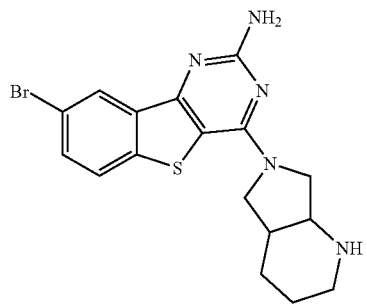

MS: 405.1. ¹H NMR (DMSO-d₆): 8.18 (d, J=2.0 Hz, 1H), 7.98 (d, J=8.6 Hz, 1H), 7.71 (dd, J=8.6, 2.1 Hz, 1H), 6.14 (s, 2H), 4.06-3.49 (m, 4H), 3.31-3.21 (m, 1H), 2.87-2.79 (m, 1H), 2.38-2.21 (m, 2H), 1.80-1.60 (m, 2H), 1.61-1.46 (m, 1H), 1.44-1.34 (m, 1H).

Example 46

7-Bromo-4-(octahydro-pyrrolo[3,4-b]pyridin-6-yl)-benzo[4,5]thieno[3,2-d]pyrimidin-2-ylamine trifluoroacetic acid salt

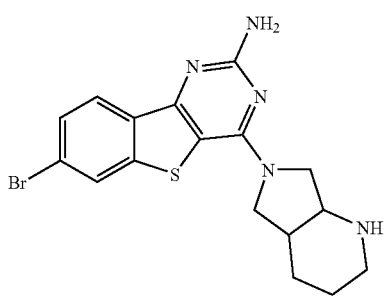

Step A: 2-Amino-7-bromo-1H-benzo[4,5]thieno[3,2-d]pyrimidin-4-one. The title compound was using methods analogous to those described in Example 44, Steps A and B. ¹H NMR (DMSO-d₆): 8.44-8.42 (m, 1H), 8.14-8.10 (m, 1H), 7.75-7.70 (m, 1H), 7.61-7.46 (m, 1.5H), 7.42 (s, 0.5H), 7.29 (s, 0.5H), 7.17 (s, 0.5H).

Step B: (7-Bromo-4-chloro-benzo[4,5]thieno[3,2-d]pyrimidin-2-yl)-phosphoramidic acid. A suspension of 2-amino-7-bromo-1H-benzo[4,5]thieno[3,2-d]pyrimidin-4-one (864 mg, 3.0 mmol), POCl₃ (2.5 mL), and N,N-dimethylaniline (765 μL, 6.0 mmol) was heated at 110° C. for 3 h, cooled to 0° C., and poured into a 1:1:1 mixture of ice water, acetonitrile, and 30% aq. NH₄OH with vigorous stirring. The mixture was filtered and the collected solid air-dried to give a pale green solid that was used without purification (1.10 g, 92%).

Step C. To a mixture of (7-bromo-4-chloro-benzo[4,5]thieno[3,2-d]pyrimidin-2-yl)-phosphoramidic acid (100 mg, 0.25 mmol) in EtOH (1.3 mL) was added octahydro-pyrrolo[3,4-b]pyridine-1-carboxylic acid tert-butyl ester (75 mg, 0.33 mmol) and pyridine (41 μL, 0.51 mmol). After 2 h at 75° C., the solution was cooled to rt and treated with 12 N HCl (0.3 mL). The mixture was heated at 75° C. for 1 h, then cooled to 0° C. The mixture was diluted with satd. aq. NaHCO₃ and extracted with CH₂Cl₂ (3×15 mL). The combined organic layers were dried and concentrated. The residue was purified by reversed-phase HPLC to yield the title compound (20 mg, 20%). MS: 404.3. ¹H NMR (DMSO-d₆): 9.35-9.17 (s, 1H), 8.82-8.59 (s, 1H), 8.56-8.40 (s, 1H), 8.33-8.15 (m, 1H), 7.85-7.70 (m, 1H), 4.45-3.78 (m, 6H), 3.06-2.75 (m, 3H), 1.94-1.62 (m, 4H).

Example 47

(S)-8-Bromo-4-(3-methylamino-pyrrolidin-1-yl)-benzo[4,5]thieno[3,2-d]pyrimidin-2-ylamine hydrochloride salt

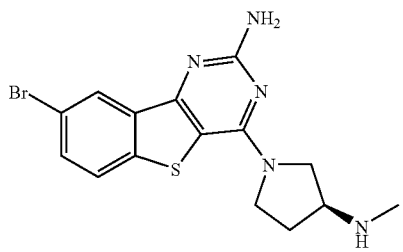

MS: 378.0. ¹H NMR (CDCl₃): 8.42 (d, J=1.9 Hz, 1H), 7.67-7.55 (m, 2H), 4.79 (br s, 2H), 4.08-3.96 (m, 2H), 3.96-3.86 (m, 1H), 3.73-3.64 (m, 1H), 3.44-3.37 (m, 1H), 2.51 (s, 1H), 2.21 (dt, J=12.7, 6.6 Hz, 1H), 1.92 (dt, J=13.1, 6.0 Hz, 1H).

Example 48

(R)-8-Bromo-4-(3-methylamino-pyrrolidin-1-yl)-benzo[4,5]thieno[3,2-d]pyrimidin-2-ylamine hydrochloride salt

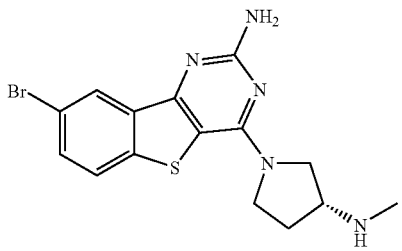

MS: 378.0. $^1$H NMR (CDCl$_3$): 8.42 (d, J=1.9 Hz, 1H), 7.67-7.55 (m, 2H), 4.79 (br s, 2H), 4.08-3.96 (m, 2H), 3.96-3.86 (m, 1H), 3.73-3.64 (m, 1H), 3.44-3.37 (m, 1H), 2.51 (s, 1H), 2.21 (dt, J=12.7, 6.6 Hz, 1H), 1.92 (dt, J=13.1, 6.0 Hz, 1H).

Example 49

(S,S)-8-Bromo-4-(2,5-diaza-bicyclo[2.2.1]hept-2-yl)-benzo[4,5]thieno[3,2-d]pyrimidin-2-ylamine hydrochloride salt

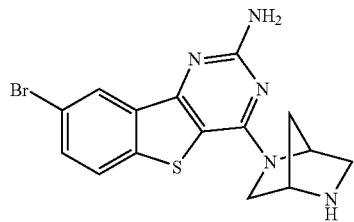

MS: 376.0. $^1$H NMR (CDCl$_3$): 8.42 (d, J=1.5 Hz, 1H), 7.66-7.56 (m, 2H), 5.13 (s, 1H), 4.82 (s, 2H), 3.98-3.88 (m, 2H), 3.80-3.70 (m, 2H), 3.23-3.13 (m, 2H), 1.92 (q, J=9.9 Hz, 2H).

Example 50

8-Bromo-4-(4-methyl-piperazin-1-yl)-benzo[4,5]thieno[3,2-d]pyrimidin-2-ylamine hydrochloride salt

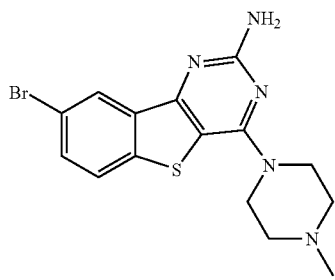

MS: 379.0. $^1$H NMR (CDCl$_3$): 8.42-8.40 (m, 1H), 7.61-7.58 (m, 2H), 4.95 (s, 2H), 3.95 (t, J=4.9 Hz, 4H), 2.54 (t, J=4.9 Hz, 4H), 2.35 (s, 3H).

Example 51

(S)-4-(3-Methylamino-pyrrolidin-1-yl)-7-trifluoromethyl-benzo[4,5]thieno[3,2-d]pyrimidin-2-ylamine trifluoroacetic acid salt

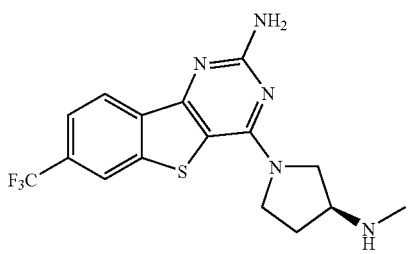

MS: 368.1. $^1$H NMR (DMSO-d$_6$): 9.14-8.88 (m, 2H), 8.79-8.68 (m, 1H), 8.53 (d, J=8.3 Hz, 1H), 7.95 (d, J=8.3 Hz, 1H), 7.83-7.41 (br m, 1H), 4.35-3.88 (m, 6H), 2.69 (s, 3H), 2.48-2.40 (m, 1H), 2.39-2.27 (m, 1H).

Example 52

(R)-4-(3-Methylamino-pyrrolidin-1-yl)-7-trifluoromethyl-benzo[4,5]thieno[3,2-d]pyrimidin-2-ylamine trifluoroacetic acid salt

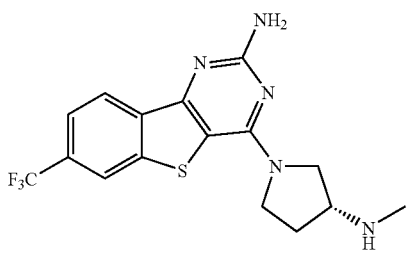

MS: 368.1. $^1$H NMR (DMSO-d$_6$): 9.14-8.88 (m, 2H), 8.79-8.68 (m, 1H), 8.53 (d, J=8.3 Hz, 1H), 7.95 (d, J=8.3 Hz, 1H), 7.83-7.41 (br m, 1H), 4.35-3.88 (m, 6H), 2.69 (s, 3H), 2.48-2.40 (m, 1H), 2.39-2.27 (m, 1H).

Example 53

(S,S)-4-(2,5-Diaza-bicyclo[2.2.1]hept-2-yl)-7-trifluoromethyl-benzo[4,5]thieno[3,2-d]pyrimidin-2-ylamine trifluoroacetic acid salt

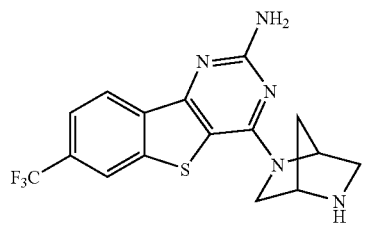

MS: 366.1. $^1$H NMR (DMSO-$d_6$): 9.47 (brs, 1H), 8.83 (brs, 1H), 8.72 (s, 1H), 8.50 (d, J=8.4 Hz, 1H), 7.94 (d, J=8.4 Hz, 1H), 7.83-7.27 (br m, 1H), 5.24 (s, 1H), 4.62 (s, 1H), 4.25-4.03 (m, 3H), 3.44 (s, 2H), 2.28 (d, J=10.6 Hz, 1H), 2.04 (d, J=11.0 Hz, 1H).

Example 54

4-(4-Methyl-piperazin-1-yl)-7-trifluoromethyl-benzo[4,5]thieno[3,2-d]pyrimidin-2-ylamine trifluoroacetic acid salt

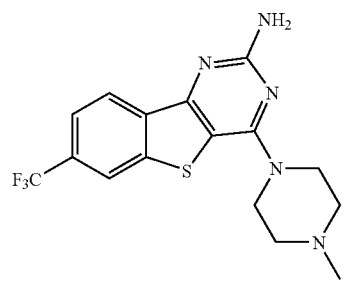

MS: 368.1. $^1$H NMR (CD$_3$OD): 8.53 (d, J=8.5 Hz, 1H), 8.46 (s, 1H), 7.89 (dd, J=8.6, 1.2 Hz, 1H), 4.76-4.11 (m, 4H), 3.61-3.45 (m, 4H), 3.00 (s, 3H).

Example 55

7-Bromo-4-(4-methyl-piperazin-1-yl)-benzo[4,5]thieno[3,2-d]pyrimidin-2-ylamine trifluoroacetic acid salt

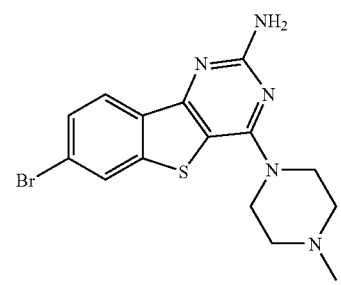

MS: 379.0. $^1$H NMR (DMSO-$d_6$): 10.23 (s, 1H), 8.42 (s, 1H), 8.16 (d, J=8.6 Hz, 1H), 7.74 (d, J=8.3 Hz, 1H), 7.24-6.72 (m, 2H), 4.80-4.56 (m, 2H), 3.28-3.06 (m, 4H), 2.94-2.78 (m, 4H).

Example 56

(R)-7-Bromo-4-(3-methylamino-pyrrolidin-1-yl)-benzo[4,5]thieno[3,2-d]pyrimidin-2-ylamine trifluoroacetic acid salt

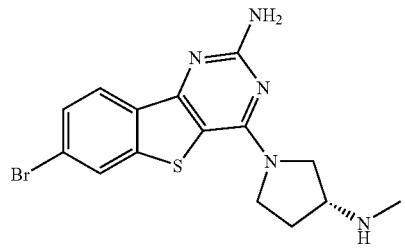

MS: 37960. $^1$H NMR (DMSO-$d_6$): 8.97-8.76 (m, 1H), 8.51 (s, 1H), 8.25 (d, J=8.1 Hz, 1H), 7.80 (d, J=8.2 Hz, 1H), 4.22-3.89 (m, 6H), 2.72-2.63 (m, 3H), 2.46-2.37 (m, 1H), 2.36-2.25 (m, 1H).

Example 57

(S)-7-Bromo-4-(3-methylamino-pyrrolidin-1-yl)-benzo[4,5]thieno[3,2-d]pyrimidin-2-ylamine trifluoroacetic acid salt

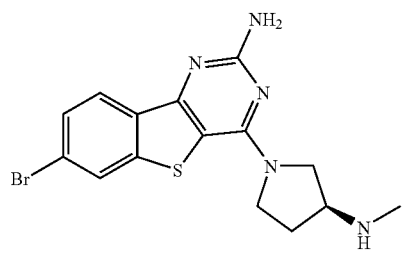

MS: 379.0. $^1$H NMR (DMSO-$d_6$): 8.97-8.76 (m, 1H), 8.51 (s, 1H), 8.25 (d, J=8.1 Hz, 1H), 7.80 (d, J=8.2 Hz, 1H), 4.22-3.89 (m, 6H), 2.72-2.63 (m, 3H), 2.46-2.37 (m, 1H), 2.36-2.25 (m, 1H).

Example 58

4-(Octahydro-pyrrolo[3,4-b]pyridin-6-yl)-7-trifluoromethyl-benzo[4,5]thieno[3,2-d]pyrimidin-2-ylamine trifluoroacetic acid salt

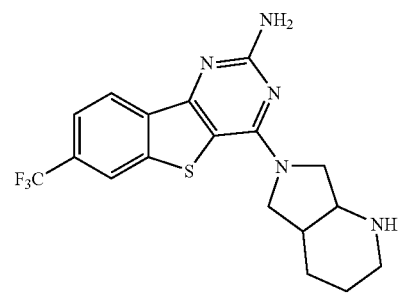

MS: 394.1. $^1$H NMR (DMSO-$d_6$): 9.25 (br s, 1H), 9.02-8.62 (br m, 2H), 8.50 (d, J=8.3 Hz, 1H, 7.91 (d, J=8.4 Hz, 1H), 7.87-7.42 (m, 1H), 4.43-3.44 (m, 5H), 3.29-3.14 (m, 1H), 2.99-2.80 (m, 2H), 1.79 (s, 1H), 1.66 (s, 1H).

Example 59

7-Chloro-4-(octahydro-pyrrolo[3,4-b]pyridin-6-yl)-benzo[4,5]thieno[3,2-d]pyrimidin-2-ylamine trifluoroacetic acid salt

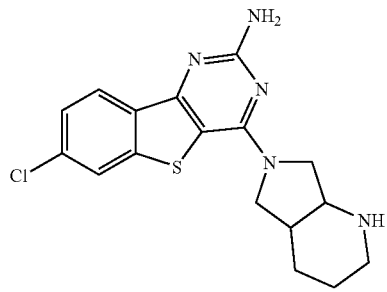

MS: 360.1. $^1$H NMR (CD$_3$OD): 8.30 (d, J=8.7 Hz, 1H), 8.13 (d, J=1.6 Hz, 1H), 7.65 (dd, J=8.7, 1.7 Hz, 1H), 4.46-3.98 (m, 5H), 3.47-3.37 (m, 1H), 3.27-3.16 (m, 1H), 3.10-3.01 (m, 1H), 2.09-1.99 (m, 2H), 1.96-1.88 (m, 2H).

Example 60

(R)-7-Chloro-4-(3-methylamino-pyrrolidin-1-yl)-benzo[4,5]thieno[3,2-d]pyrimidin-2-ylamine trifluoroacetic acid salt

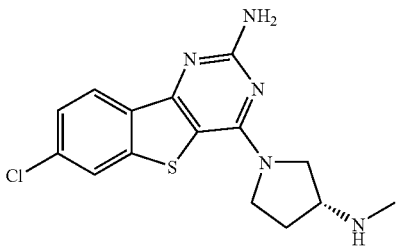

MS: 334.1. $^1$H NMR (CD$_3$OD): 6.77 (d, J=8.7 Hz, 1H), 6.60 (d, J=1.7 Hz, 1H), 6.11 (dd, J=8.7, 1.8 Hz, 1H), 2.92-2.65 (m, 4H), 2.63-2.54 (m, 1H), 1.41-1.34 (m, 3H), 1.24-1.10 (m, 1H), 1.04-0.89 (m, 1H).

Example 61

(S)-7-Chloro-4-(3-methylamino-pyrrolidin-1-yl)-benzo[4,5]thieno[3,2-d]pyrimidin-2-ylamine trifluoroacetic acid salt

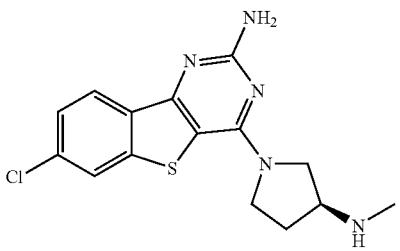

MS: 334.1. $^1$H NMR (CD$_3$OD): 6.77 (d, J=8.7 Hz, 1H), 6.61 (d, J=1.7 Hz, 1H), 6.11 (dd, J=8.7, 1.8 Hz, 1H), 2.92-2.65 (m, 4H), 2.63-2.54 (m, 1H), 1.41-1.34 (m, 3H), 1.24-1.10 (m, 1H), 1.04-0.89 (m, 1H).

Example 62

(S,S)-7-Chloro-4-(2,5-diaza-bicyclo[2.2.1]hept-2-yl)-benzo[4,5]thieno[3,2-d]pyrimidin-2-ylamine trifluoroacetic acid salt

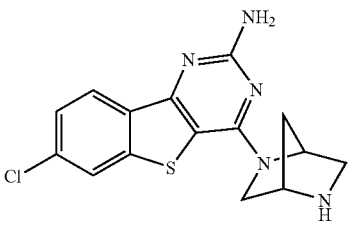

MS: 332.1. $^1$H NMR (CD$_3$OD): 8.30 (d, J=8.7 Hz, 1H), 8.12 (d, J=1.5 Hz, 1H), 7.63 (dd, J=8.7, 1.7 Hz, 1H), 5.51 (s, 1H), 4.70 (s, 1H), 4.33-4.20 (m, 2H), 3.64-3.51 (m, 2H), 2.47-2.37 (m, 1H), 2.26-2.19 (m, 1H).

Example 63

7-Chloro-4-(4-methyl-piperazin-1-yl)-benzo[4,5]thieno[3,2-d]pyrimidin-2-ylamine trifluoroacetic acid salt

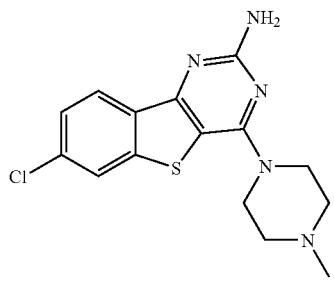

MS: 334.1. $^1$H NMR (CD$_3$OD): 7.00 (d, J=8.7 Hz, 1H), 6.80 (d, J=1.8 Hz 1H), 6.33 (dd, J=8.7, 1.8 Hz, 1H), 3.35-2.51 (m, 4H), 2.20 (s, 4H), 1.68 (s, 3H).

Example 64

8-Chloro-4-(octahydro-pyrrolo[3,4-b]pyridin-6-yl)-benzo[4,5]thieno[3,2-d]pyrimidin-2-ylamine trifluoroacetic acid salt

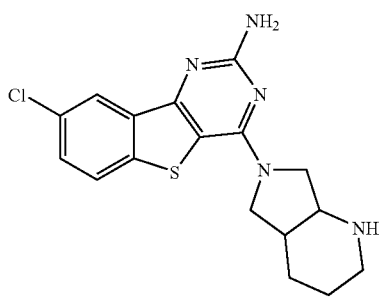

MS: 360.1. $^1$H NMR (CD$_3$OD): 8.33 (d, J=1.8 Hz, 1H), 8.06 (d, J=8.7, 1H), 7.72 (dd, J=8.7, 2.0 Hz, 1H), 4.50-3.93 (m, 5H), 3.44-3.37 (m, 1H), 3.17-3.06 (m, 1H), 3.05-2.90 (m, 1H), 2.06-1.95 (m, 2H), 1.93-1.85 (m, 2H).

Example 65

(S)-8-Chloro-4-(3-methylamino-pyrrolidin-1-yl)-benzo[4,5]thieno[3,2-d]pyrimidin-2-ylamine trifluoroacetic acid salt

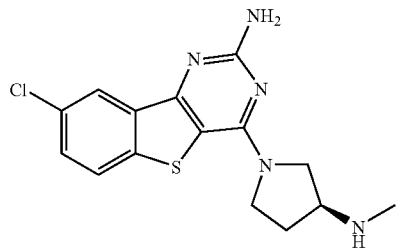

MS: 334.1. ¹H NMR (CD₃OD): 8.32 (d, J=2.0 Hz, 1H), 8.00 (d, J=8.8 Hz, 1H), 7.68 (dd, J=8.8, 2.0 Hz, 1H), 4.39-4.14 (m, 4H), 4.11-4.01 (m, 1H), 2.84 (s, 3H), 2.71-2.57 (m, 1H), 2.50-2.37 (m, 1H).

Example 66

(R)-8-Chloro-4-(3-methylamino-pyrrolidin-1-yl)-benzo[4,5]thieno[3,2-d]pyrimidin-2-ylamine trifluoroacetic acid salt

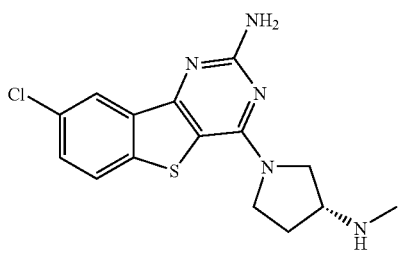

MS: 334.1. ¹H NMR (CD₃OD): 8.32 (d, J=2.0 Hz, 1H), 8.02 (d, J=8.8 Hz, 1H), 7.68 (dd, J=8.8, 2.0 Hz, 1H), 4.39-4.14 (m, 4H), 4.11-4.01 (m, 1H), 2.84 (s, 3H), 2.71-2.57 (m, 1H), 2.50-2.37 (m, 1H).

Example 67

8-Chloro-4-(4-methyl-piperazin-1-yl)-benzo[4,5]thieno[3,2-d]pyrimidin-2-ylamine trifluoroacetic acid salt

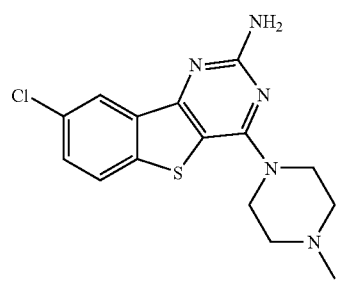

MS: 334.01. ¹H NMR (CD₃OD): 8.35 (d, J=1.8 Hz, 1H), 8.00 (d, J=8.7 Hz, 1H), 7.69 (dd, J=8.7, 2.0 Hz, 1H), 4.70-3.86 (m, 4H), 3.53 (s, 4H), 2.99 (s, 3H).

Example 68

(S,S)-8-Chloro-4-(2,5-diaza-bicyclo[2.2.1]hept-2-yl)-benzo[4.5]thieno[3,2-d]pyrimidin-2-ylamine trifluoroacetic acid salt

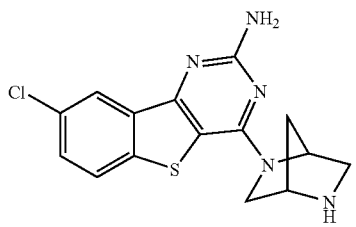

MS: 332.0. ¹H NMR (CD₃OD): 8.35 (d, J=1.7 Hz, 1H), 8.03 (d, J=8.8 Hz, 1H), 7.69 (dd, J=8.8, 1.9 Hz, 1H), 5.54-5.45 (m, 1H), 4.73-4.65 (m, 1H), 4.36-4.14 (m, 2H), 3.66-3.50 (m, 2H), 2.48-2.35 (m, 1H), 2.26-2.17 (m, 1H).

Example 69

8-Chloro-4-(hexahydro-pyrrolo[1,2-a]pyrazin-2-yl)-benzo[4,5]furo[3,2-d]pyrimidin-2-ylamine trifluoroacetic acid salt

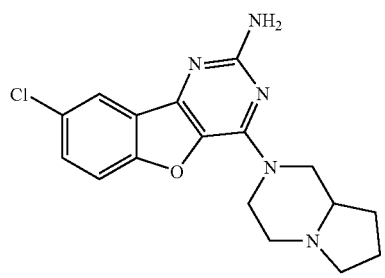

MS: 344.1.

Example 70

8-Fluoro-4-(4-methyl-piperazin-1-yl)-benzo[4,5]thieno[3,2-d]pyrimidin-2-ylamine trifluoroacetic acid salt

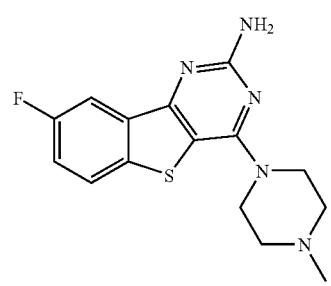

MS: 318.0.

Example 71

8-Fluoro-4-(hexahydro-pyrrolo[3,4-b]pyrrol-5-yl)-benzo[4,5]furo[3,2-d]pyrimidin-2-ylamine trifluoroacetic acid salt

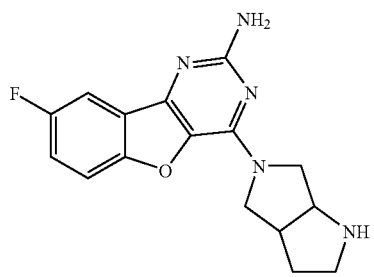

MS: 314.2.

Example 72

(S)-8-Chloro-4-(3-ethylamino-piperidin-1-yl)-benzo[4,5]furo[3,2-d]pyrimidin-2-ylamine trifluoroacetic acid salt

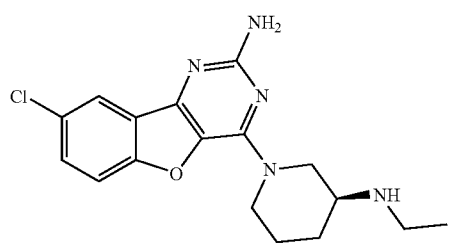

MS: 346.2. $^1$H NMR (CD$_3$OD): 8.04 (d, J=1.8 Hz, 1H), 7.72-7.68 (m, 2H), 4.62-3.86 (m, 5H), 3.27-3.17 (m, 2H), 2.68-2.35 (m, 2H), 1.38 (t, J=7.2 Hz, 3H).

Example 73

(R)-8-Chloro-4-(3-ethylamino-pyrrolidin-1-yl)-benzo[4,5]furo[3,2-d]pyrimidin-2-ylamine trifluoroacetic acid salt

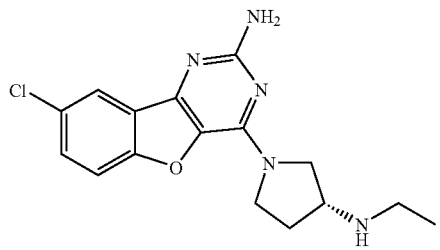

MS: 332.1. $^1$H NMR (CD$_3$OD): 8.04 (d, J=1.8 Hz, 1H), 7.72-7.68 (m, 2H), 4.62-3.86 (m, 5H), 3.27-3.17 (m, 2H), 2.68-2.35 (m, 2H), 1.38 (t, J=7.2 Hz, 3H).

Example 74

(S)-8-Chloro-4-(3-methylamino-piperidin-1-yl)-benzo[4,5]furo[3,2-d]pyrimidin-2-ylamine citrate salt

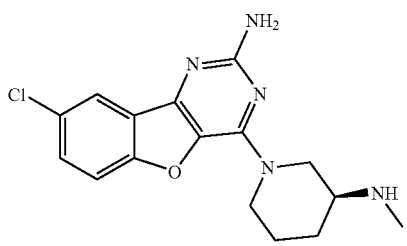

MS: 332.1.

Example 75

(S)-8-Chloro-4-(3-dimethylamino-piperidin-1-yl)-benzo[4,5]furo[3,2-d]pyrimidin-2-ylamine trifluoroacetic acid salt

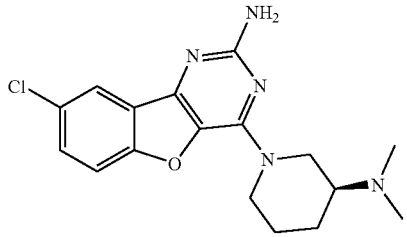

MS: 346.2.

Example 76

(R)-8-Fluoro-4-(3-methylamino-pyrrolidin-1-yl)-benzo[4.5]thieno[3,2-d]pyrimidin-2-ylamine trifluoroacetic acid salt

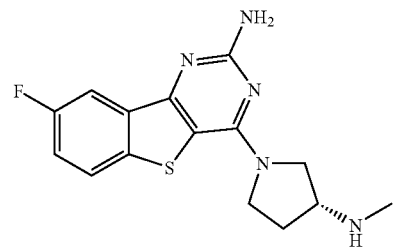

MS: 318.0.

Example 77

(S,S)-7-Bromo-4-(2,5-diaza-bicyclo[2.2.1]hept-2-yl)-benzo[4,5]thieno[3,2-d]pyrimidin-2-ylamine trifluoroacetic acid salt

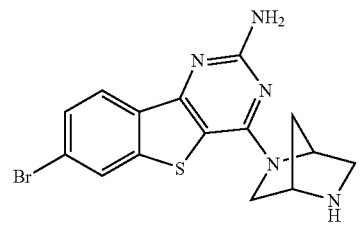

MS: 377.3.

Example 78

4-(6-Amino-3-aza-bicyclo[3.1.0]hex-3-yl)-8-chloro-benzo[4,5]furo[3,2-d]pyrimidin-2-ylamine trifluoroacetic acid salt

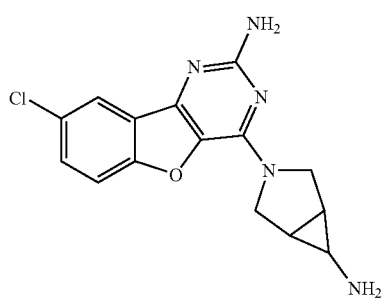

MS: 316.1.

Example 79

(R)-4-(2-Aminomethyl-pyrrolidin-1-yl)-8-chloro-benzo[4,5]furo[3,2-d]pyrimidin-2-ylamine trifluoroacetic acid salt

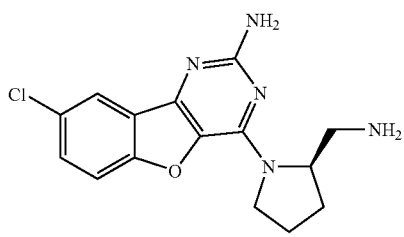

MS: 318.1.

Example 80

8-Chloro-4-(hexahydro-pyrrolo[3,4-b]pyrrol-5-yl)-benzo[4,5]furo[3,2-d]pyrimidin-2-ylamine trifluoroacetic acid salt

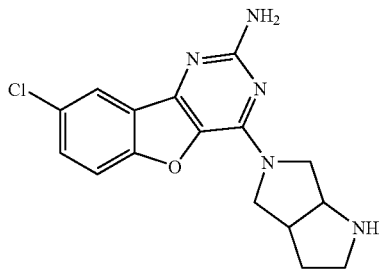

MS: 330.1. $^1$H NMR (CD$_3$OD): 8.05 (s, 1H), 7.75-7.62 (m, 2H), 4.58-3.93 (m, 5H), 3.55-3.33 (m, 3H), 2.43-2.32 (m, 1H), 2.17-2.04 (m, 1H).

Example 81

(R,R)-8-Chloro-4-(2,5-diaza-bicyclo[2.2.1]hept-2-yl)-benzo[4,5]furo[3,2-d]pyrimidin-2-ylamine trifluoroacetic acid salt

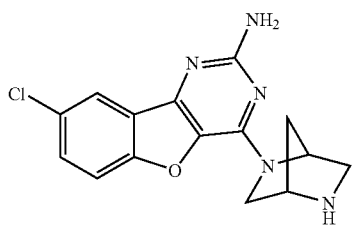

MS: 316.1.

Example 82

(R,R)-8-Chloro-4-(octahydro-pyrrolo[3,4-b]pyridin-6-yl)-benzo[4,5]furo[3,2-d]pyrimidin-2-ylamine citrate salt

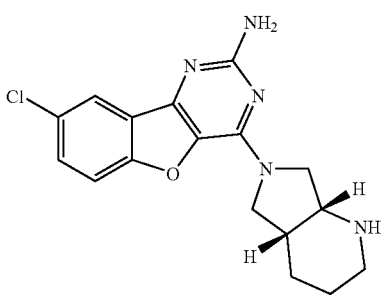

MS: 344.1.

Example 83

8-Chloro-4-(octahydro-pyrrolo[3,4-b]pyridin-6-yl)-benzo[4,5]furo[3,2-d]pyrimidin-2-ylamine citrate salt

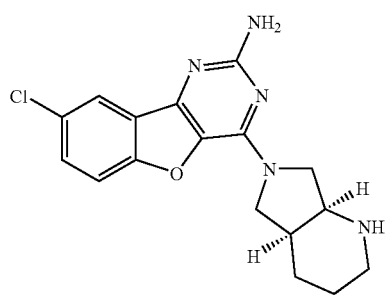

MS: 344.1.

The compounds in Examples 84-163 were prepared using methods analogous to those described in the preceding examples.

Example 84

(R)-4-(3-Methylamino-pyrrolidin-1-yl)-9-trifluoromethyl-benzo[4,5]furo[3,2-d]pyrimidin-2-ylamine citrate salt

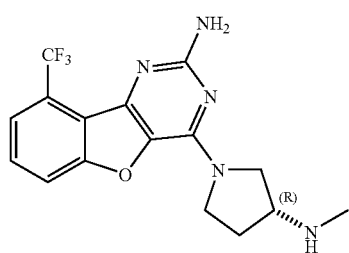

MS (ESI): mass calcd. for $C_{16}H_{16}F_3N_5O$, 351.1; m/z found, 352.3 [M+H]$^+$. $^1$H NMR (CDCl$_3$): 7.70 (d, J=8.38 Hz, 1H), 7.66 (d, J=7.54 Hz, 1H), 7.57 (t, J=7.94 Hz, 1H), 4.77 (s, 2H), 4.17-3.60 (m, 3H), 2.54 (s, 3H), 2.28-2.20 (m, 1H), 1.98-1.88 (m, 1H).

Example 85

(S,S)-4-(2,5-Diaza-bicyclo[2.2.1]hept-2-yl)-9-methoxy-benzo[4,5]furo[3,2-d]pyrimidin-2-ylamine trifluoroacetic acid salt

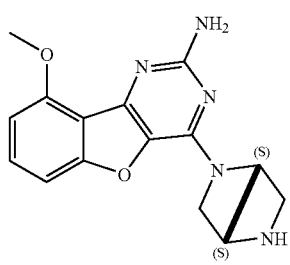

MS (ESI): mass calcd. for $C_{15}H_{17}N_5O_2$, 311.1; m/z found, 312.2 [M+H]$^+$. $^1$H NMR (CDCl$_3$): 7.78-7.68 (m, 1H), 7.39-7.27 (m, 1H), 7.09-7.02 (m, 1H), 5.77 (s, 0.5H), 5.50 (m, 0.5H), 4.73-4.69 (m, 1H), 4.42 and 4.33 (AB; J$_{AB}$=12.1 Hz, 1H), 4.12 (s, 3H), 4.03 and 3.99 (AB, J$_{AB}$=13.3 Hz, 1H), 3.74-3.44 (m, 2H), 2.48-2.20 (m, 2H).

Example 86

9-Methoxy-4-piperazin-1-yl-benzo[4,5]furo[3,2-d]pyrimidin-2-ylamine trifluoroacetic acid salt

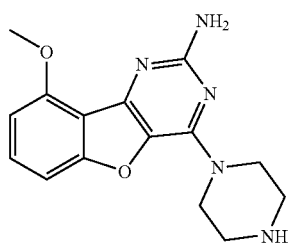

MS (ESI): mass calcd. for $C_{15}H_{17}N_5O_2$, 299.1; m/z found, 300.2 [M+H]$^+$. $^1$H NMR (CDCl$_3$): 7.73 (t, J=8.36 Hz, 1H), 7.33 (d, J=8.46 Hz, 1H), 7.06 (d, J=8.19 Hz, 1H), 4.57-4.38 (m, 4H), 4.16-4.09 (m, 3H), 3.54-3.45 (m, 4H).

Example 87

(S)-4-(3-Amino-piperidin-1-yl)-9-methoxy-benzo[4,5]furo[3,2-d]pyrimidin-2-ylamine trifluoroacetic acid salt

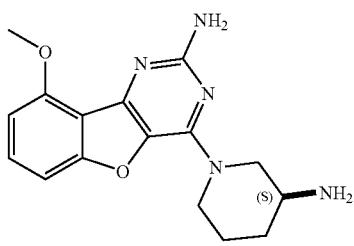

MS (ESI): mass calcd. for $C_{16}H_{19}N_5O_2$, 313.1; m/z found, 314.2 [M+H]$^+$. $^1$H NMR (CDCl$_3$): 7.72 (t, J=8.36 Hz, 1H), 7.33 (d, J=8.49 Hz, 1H), 7.04 (d, J=8.20 Hz, 1H), 4.63-4.50 (m, 1H), 4.12 (s, 3H), 4.01-3.89 (m, 1H), 3.74-3.65 (m, 1H), 3.66-3.61 (m, 1H), 3.60-3.52 (m, 1H), 2.37-2.19 (m, 1H), 2.09-1.97 (m, 1H), 1.95-1.78 (m, 2H).

Example 88

9-Methoxy-4-(4-methyl-piperazin-1-yl)-benzo[4,5]furo[3,2-d]pyrimidin-2-ylamine trifluoroacetic acid salt

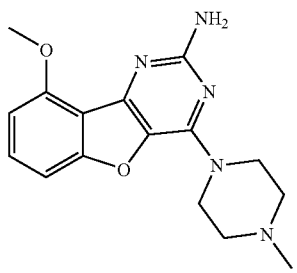

MS (ESI): mass calcd. for $C_{16}H_{19}N_5O_2$, 313.1; m/z found, 314.2 [M+H]$^+$. $^1$H NMR (CDCl$_3$): 7.74 (t, J=8.35 Hz, 1H), 7.33 (d, J=8.47 Hz, 1H), 7.06 (d, J=8.22 Hz, 1H), 4.81 (s, 3H), 4.13 (s, 4H), 3.79-3.43 (m, 4H), 3.01 (s, 3H).

Example 89

8-Methoxy-4-(4-methyl-piperazin-1-yl)-benzo[4,5]furo[3,2-d]pyrimidin-2-ylamine trifluoroacetic acid salt

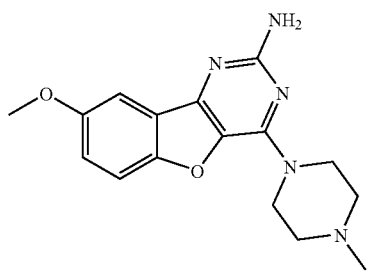

MS (ESI): mass calcd. for $C_{16}H_{19}N_5O_2$, 313.1; m/z found, 314.2 [M+H]$^+$. $^1$H NMR (CDCl$_3$): 7.58 (d, J=9.23 Hz, 1H), 7.43 (d, J=2.54 Hz, 1H), 7.29 (dd, J=9.22, 2.63 Hz, 1H), 4.83 (s, 3H), 3.88-3.80 (m, 4H), 3.58-3.34 (m, 4H), 2.92 (s, 3H).

Example 90

4-Piperazin-1-yl-9-trifluoromethyl-benzo[4,5]furo[3,2-d]pyrimidin-2-ylamine citrate salt

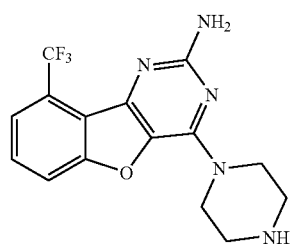

MS (ESI): mass calcd. for $C_{15}H_{14}F_3N_5O$, 337.1; m/z found, 338.1 [M+H]$^+$. $^1$H NMR (CDCl$_3$): 7.72 (d, J=8.37 Hz, 1H), 7.67 (d, J=7.59 Hz, 1H), 7.59 (t, J=7.91, 7.91 Hz, 1H), 4.77 (s, 2H), 4.06-4.02 (m, 4H), 3.07-2.98 (m, 4H).

Example 91

4-(4-Methyl-piperazin-1-yl)-9-trifluoromethyl-benzo[4,5]furo[3,2-d]pyrimidin-2-ylamine citrate salt

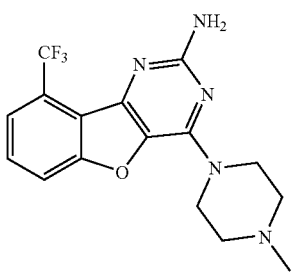

MS (ESI): mass calcd. for $C_{16}H_{16}F_3N_5O$, 351.1; m/z found, 352.2 [M+H]$^+$. $^1$H NMR (CDCl$_3$): 7.72 (d, J=8.33 Hz, 1H), 7.67 (d, J=7.55 Hz, 1H), 7.59 (t, J=7.94, 7.94 Hz, 1H), 4.78 (s, 2H), 4.13-4.02 (m, 4H), 2.61-2.50 (m, 4H), 2.38 (s, 3H).

Example 92

(S)-4-(3-Amino-piperidin-1-yl)-9-trifluoromethyl-benzo[4,5]furo[3,2-d]pyrimidin-2-ylamine citrate salt

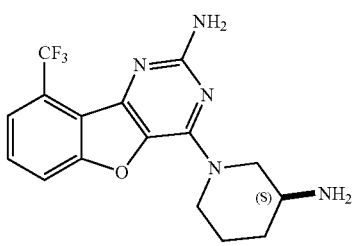

MS (ESI): mass calcd. for $C_{16}H_{16}F_3N_5O$, 351.1; m/z found, 352.2 [M+H]$^+$. $^1$H NMR (CDCl$_3$): 7.73 (d, J=8.30 Hz, 1H), 7.67 (d, J=7.54 Hz, 1H), 7.59 (t, J=7.96 Hz, 1H), 4.77 (s, 2H), 4.73-4.68 (m, 1H), 4.61 (d, J=13.26 Hz, 1H), 3.36-3.29 (m, 1H), 3.10-3.03 (m, 1H), 3.01-2.95 (m, 1H), 2.12-2.03 (m, 1H), 1.94-1.84 (m, 1H), 1.74-1.63 (m, 1H), 1.49-1.38 (m, 1H).

Example 93

(S)-4-(3-Amino-piperidin-1-yl)-8,9-dichloro-benzo[4,5]furo[3,2-d]pyrimidin-2-ylamine trifluoroacetic acid salt

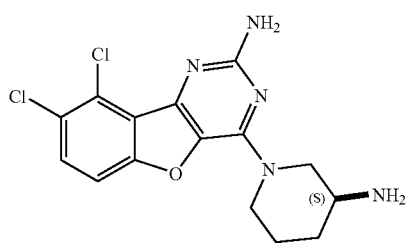

MS (ESI): mass calcd. for $C_{15}H_{15}Cl_2N_5O$, 352.1; m/z found, 353.1 [M+H]$^+$. $^1$H NMR (CD$_3$OD): 7.90 (dd, J=8.99, 3.64 Hz, 1H), 7.77 (dd, J=9.01, 3.58 Hz, 1H), 4.83-4.74 (m, 1H), 4.62-4.51 (m, 1H), 4.01-3.88 (m, 2H), 3.63-3.53 (m, 1H), 2.31-2.21 (m, 1H), 2.10-2.00 (m, 1H), 1.95-1.81 (m, 2H).

Example 94

(S,S)-4-(2,5-Diaza-bicyclo[2.2.1]hept-2-yl)-9-trifluoromethyl-benzo[4,5]furo[3,2-d]pyrimidin-2-ylamine citrate salt

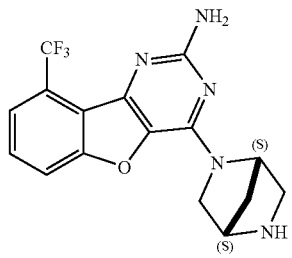

MS (ESI): mass calcd. for $C_{15}H_{15}Cl_2N_5O$, 349.1; m/z found, 350.2 [M+H]$^+$. $^1$H NMR (CDCl$_3$): 7.71 (d, J=8.21 Hz, 1H), 7.67 (d, J=7.34 Hz, 1H), 7.61-7.56 (m, 1H), 4.78 (s, 2H), 3.93-3.88 (m, 1H), 3.24-3.09 (m, 2H), 2.02-1.88 (m, 2H), 1.42-1.31 (m, 1H).

Example 95

(cis)-8-Chloro-4-(hexahydro-pyrrolo[3,4-b]pyrrol-1-yl)-benzo[4,5]furo[3,2-d]pyrimidin-2-ylamine trifluoroacetic acid salt

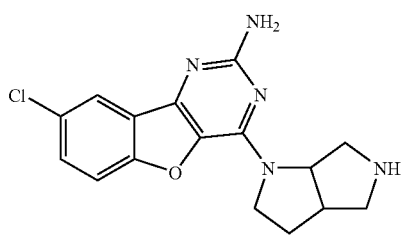

MS (ESI): mass calcd. for $C_{16}H_{16}ClN_5O$, 329.1; m/z found, 330.1 [M+H]$^+$. $^1$H NMR (CD$_3$OD): 8.02-7.97 (m, 1H), 7.71-7.63 (m, 2H), 4.99-4.87 (m, 1H), 4.48-4.12 (m, 2H), 3.89-3.69 (m, 1H), 3.64-3.52 (m, 2H), 3.34-3.25 (m, 2H), 2.41-2.23 (m, 1H), 2.16-1.99 (m, 1H).

Example 96

N$^4$-(2-Amino-ethyl)-8-chloro-N$^4$-methyl-benzo[4,5]furo[3,2-d]pyrimidine-2,4-diamine trifluoroacetic acid salt

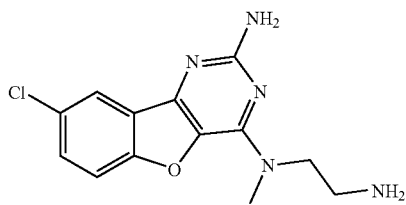

MS (ESI): mass calcd. for $C_{13}H_{14}ClN_5O$, 292.1; m/z found, 292.2 [M+H]$^+$. $^1$H NMR (CD$_3$OD): 8.06 (d, J=1.98 Hz, 1H), 7.77-7.68 (m, 2H), 4.24-4.07 (m, 2H), 3.67 (s, 3H), 3.40 (t, J=5.87 Hz, 2H).

Example 97

8-Chloro-4-(3,8-diaza-bicyclo[3.2.1]oct-3-yl)-benzo[4,5]furo[3,2-d]pyrimidin-2-ylamine trifluoroacetic acid salt

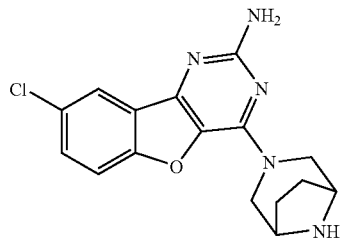

MS (ESI): mass calcd. for $C_{16}H_{16}ClN_5O$, 329.1; m/z found, 330.1 [M+H]$^+$. $^1$H NMR (CD$_3$OD): 8.11-8.10 (m, 1H), 7.77-7.73 (m, 2H), 5.07 (d, J=13.50 Hz, 2H), 4.37-4.31 (m, 2H), 3.95-3.70 (m, 2H), 2.28-2.16 (m, 2H), 2.13-2.05 (m, 2H).

Example 98

(S,S)-8,9-Dichloro-4-(2,5-diaza-bicyclo[2.2.1]hept-2-yl)-benzo[4,5]furo[3,2-d]pyrimidin-2-ylamine trifluoroacetic acid salt

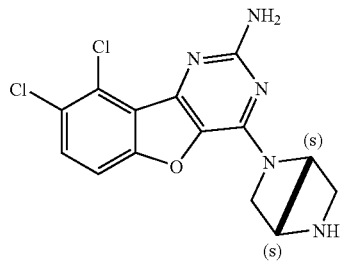

MS (ESI): mass calcd. for $C_{15}H_{13}Cl_2N_5O$, 349.1; m/z found, 351.1 [M+H]$^+$. $^1$H NMR (CD$_3$OD): 7.90 (d, J=8.99 Hz, 1H), 7.77 (d, J=8.66 Hz, 1H), 5.88-5.38 (m, 1H), 4.78-4.65 (m, 1H), 4.55-3.91 (m, 2H), 3.75-3.49 (m, 2H), 2.50-2.34 (m, 1H), 2.33-2.18 (m, 1H).

Example 99

(R)-8,9-Dichloro-4-(3-methylamino-pyrrolidin-1-yl)-benzo[4,5]furo[3,2-d]pyrimidin-2-ylamine trifluoroacetic acid salt

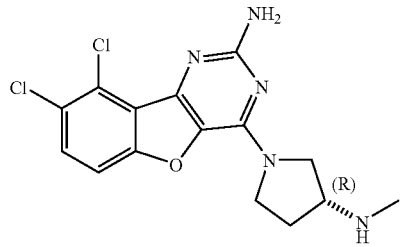

MS (ESI): mass calcd. for $C_{15}H_{15}Cl_2N_5O$, 352.1; m/z found, 353.1 [M+H]$^+$. $^1$H NMR (CD$_3$OD): 7.87 (d, J=9.02 Hz, 1H), 7.78-7.71 (m, 1H), 4.67-3.83 (m, 5H), 2.86 (s, 3H), 2.76-2.27 (m, 2H).

Example 100

(R)-9-Methoxy-4-(3-methylamino-pyrrolidin-1-yl)-benzo[4,5]furo[3,2-d]pyrimidin-2-ylamine trifluoroacetic acid salt

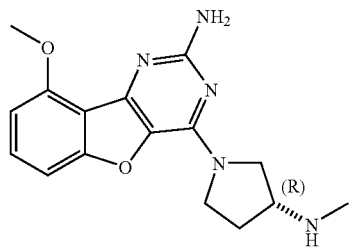

MS (ESI): mass calcd. for $C_{16}H_{19}N_5O_2$, 313.1; m/z found, 314.1 [M+H]$^+$. $^1$H NMR (CD$_3$OD): 7.70 (t, J=8.37 Hz, 1H), 7.31 (d, J=8.50 Hz, 1H), 7.03 (d, J=8.15 Hz, 1H), 4.62-4.25 (m, 2H), 4.21-3.92 (m, 6H), 2.88-2.81 (m, 3H), 2.73-2.27 (m, 2H).

Example 101

8,9-Dichloro-4-(4-methyl-piperazin-1-yl)-benzo[4,5]furo[3,2-d]pyrimidin-2-ylamine trifluoroacetic acid salt

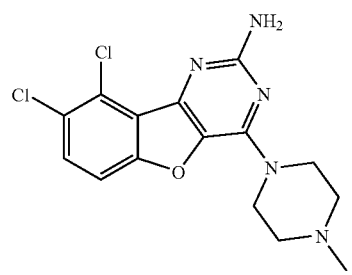

MS (ESI): mass calcd. for $C_{15}H_{15}Cl_2N_5O$, 351.1; m/z found, 353.1 [M+H]$^+$. $^1$H NMR (CD$_3$OD): 7.89 (d, J=9.00 Hz, 1H), 7.76-7.74 (m, 1H), 3.67-3.45 (m, 4H), 3.37-3.26 (m, 4H), 3.01 (s, 3H).

Example 102

(R)-8-Methoxy-4-(3-methylamino-pyrrolidin-1-yl)-benzo[4,5]furo[3,2-d]pyrimidin-2-ylamine trifluoroacetic acid salt

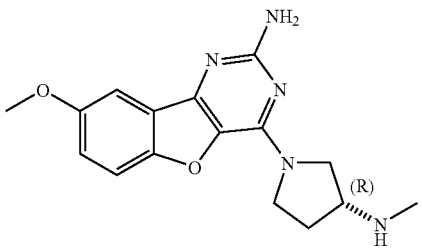

MS (ESI): mass calcd. for $C_{16}H_{19}N_5O_2$, 313.1; m/z found, 314.2 [M+H]$^+$. $^1$H NMR (CD$_3$OD): 7.57 (d, J=9.20 Hz, 1H), 7.41 (d, J=2.60 Hz, 1H), 7.27 (dd, J=9.23, 2.66 Hz, 1H), 4.54-4.16 (m, 2H), 4.15-3.88 (m, 3H), 3.82 (s, 3H), 2.77 (s, 3H), 2.64-2.43 (m, 1H), 2.41-2.16 (m, 1H).

Example 103

4-(3-Aminomethyl-azetidin-1-yl)-8-chloro-benzo[4,5]furo[3,2-d]pyrimidin-2-ylamine trifluoroacetic acid salt

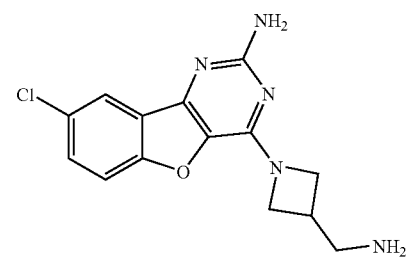

MS (ESI): mass calcd. for $C_{14}H_{14}ClN_5O$, 303.1; m/z found, 304.1 [M+H]$^+$. $^1$H NMR (CD$_3$OD): 8.06-8.01 (m, 1H), 7.72-7.69 (m, 2H), 4.68-4.39 (m, 2H), 4.36-4.09 (m, 1H), 3.40 (d, J=7.53 Hz, 2H), 3.33-3.26 (m, 2H).

Example 104

8,9-Dichloro-4-piperazin-1-yl-benzo[4,5]furo[3,2-d]pyrimidin-2-ylamine trifluoroacetic acid salt

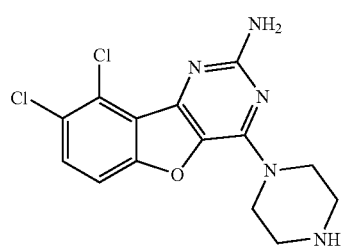

MS (ESI): mass calcd. for $C_{14}H_{13}Cl_2N_5O$, 337.1; m/z found, 339.1 [M+H]$^+$. $^1$H NMR (CD$_3$OD): 7.91-7.86 (m, 1H), 7.76-7.72 (m, 1H), 4.53-4.38 (m, 4H), 3.54-3.44 (m, 4H).

Example 105

(cis)-8-Methoxy-4-(octahydro-pyrrolo[3,4-b]pyridin-6-yl)-benzo[4,5]furo[3,2-d]pyrimidin-2-ylamine trifluoroacetic acid salt

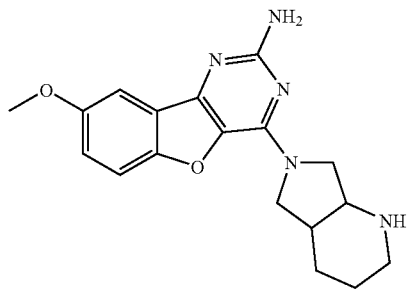

MS (ESI): mass calcd. for $C_{18}H_{21}N_5O_2$, 339.1; m/z found, 340.1 [M+H]$^+$. $^1$H NMR (CD$_3$OD): 7.70-7.61 (m, 1H), 7.52-7.47 (m, 1H), 7.39-7.32 (m, 1H), 4.66-4.38 (m, 1H), 4.27-3.98 (m, 3H), 3.93 (s, 3H), 3.49-3.38 (m, 1H), 3.21-2.83 (m, 3H), 2.09-1.84 (m, 4H).

Example 106

(S,S)-8-Chloro-4-(5-methyl-2,5-diaza-bicyclo[2.2.1]hept-2-yl)-benzo[4,5]furo[3,2-d]pyrimidin-2-ylamine trifluoroacetic acid salt

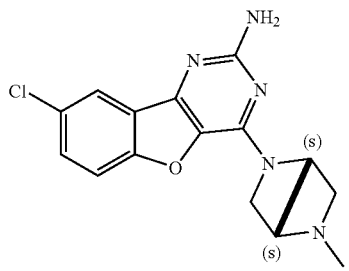

MS (ESI): mass calcd. for $C_{16}H_{16}ClN_5O$, 329.1; m/z found, 330.1 [M+H]$^+$. $^1$H NMR (CD$_3$OD): 8.06 (s, 1H), 7.81-7.67 (m, 2H), 5.79-5.71 (m, 0.5H), 5.54-5.43 (m, 0.5H), 4.69-4.49 (m, 2H), 4.44-4.30 (m, 1H), 4.25-3.94 (m, 2H), 3.09 (s, 3H), 2.70-2.35 (m, 3H).

Example 107

(S)-4-(3-Amino-piperidin-1-yl)-8-methoxy-benzo[4,5]furo[3,2-d]pyrimidin-2-ylamine trifluoroacetic acid salt

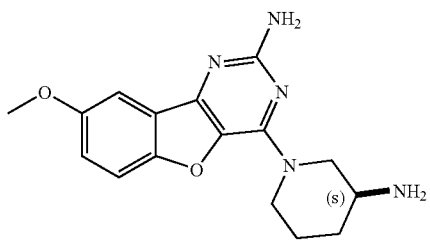

MS (ESI): mass calcd. for $C_{16}H_{19}N_5O_2$, 313.1; m/z found, 314.1 [M+H]$^+$. $^1$H NMR (CD$_3$OD): 7.67 (d, J=9.23 Hz, 1H), 7.54-7.47 (m, 1H), 7.36 (dd, J=9.21, 2.64 Hz, 1H), 4.65-4.50 (m, 1H), 4.00-3.86 (m, 5H), 3.61-3.50 (m, 2H), 2.32-2.19 (m, 1H), 2.07-1.99 (m, 1H), 1.95-1.79 (m, 2H).

Example 108

(R)-4-(3-Amino-pyrrolidin-1-yl)-benzo[4,5]furo[3,2-d]pyrimidin-2-ylamine

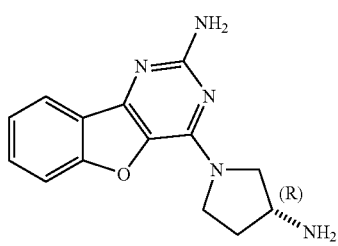

MS (ESI): mass calcd. for $C_{14}H_{15}N_5O$, 269.1; m/z found, 270.2 [M+H]$^+$. $^1$H NMR (DMSO): 7.89 (d, J=7.75 Hz, 1H), 7.63 (d, J=8.35 Hz, 1H), 7.58-7.53 (m, 1H), 7.38-7.34 (m, 1H), 5.92-5.86 (m, 2H), 3.22-3.08 (m, 2H), 2.54-2.45 (m, 3H), 2.13-1.99 (m, 1H), 1.79-1.66 (m, 1H).

Example 109

(R)-3-Chloro-8-(3-methylamino-pyrrolidin-1-yl)-9-oxa-1,5,7-triaza-fluoren-6-ylamine

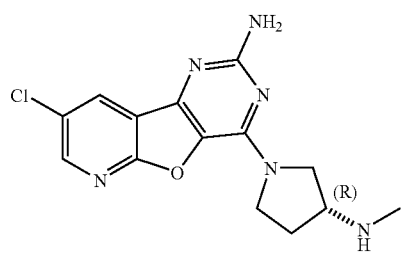

MS (ESI): mass calcd. for $C_{14}H_{15}ClN_6O$, 318.1; m/z found, 319.1 [M+H]$^+$. $^1$H NMR (CD$_3$OD): 8.56 (d, J=2.40 Hz, 1H), 8.44 (d, J=2.34 Hz, 1H), 4.52-3.85 (m, 5H), 2.75 (s, 3H), 2.59-2.42 (m, 1H), 2.40-2.21 (m, 1H).

Example 110

N$^4$-Azetidin-3-ylmethyl-8-chloro-benzo[4,5]furo[3,2-d]pyrimidine-2,4-diamine trifluoroacetic acid salt

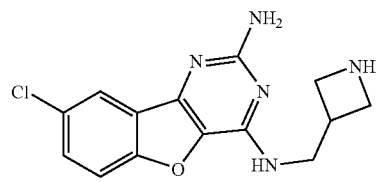

MS (ESI): mass calcd. for $C_{14}H_{14}ClN_5O$, 303.1; m/z found, 304.1 [M+H]$^+$. $^1$H NMR (CD$_3$OD): 8.05 (d, J=1.95 Hz, 1H), 7.77-7.69 (m, 2H), 4.19 (t, J=10.09 Hz, 2H), 4.15-4.07 (m, 2H), 3.92 (d, J=6.49 Hz, 2H), 3.41-3.35 (m, 1H).

Example 111

N⁴-Azetidin-3-yl-8-chloro-benzo[4,5]furo[3,2-d]pyrimidine-2,4-diamine trifluoroacetic acid salt

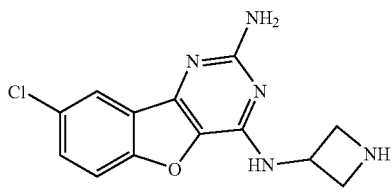

MS (ESI): mass calcd. for $C_{13}H_{12}ClN_5O$, 289.1; m/z found, 290.1 [M+H]⁺. ¹H NMR (CD₃OD): 8.09-8.04 (m, 1H), 7.80-7.70 (m, 2H), 5.18-5.06 (m, 1H), 4.55-4.38 (m, 4H).

Example 112

N⁴-(2-Amino-ethyl)-8-chloro-benzo[4,5]furo[3,2-d]pyrimidine-2,4-diamine trifluoroacetic acid salt

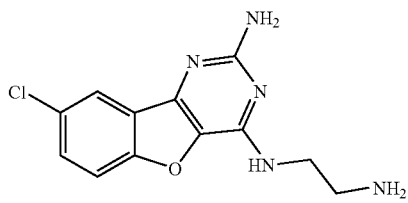

MS (ESI): mass calcd. for $C_{12}H_{12}ClN_5O$, 277.1; m/z found, 278.1 [M+H]⁺. ¹H NMR (CD₃OD): 8.09-8.05 (m, 1H), 7.77-7.70 (m, 2H), 4.02-3.90 (m, 2H), 3.37-3.33 (m, 2H).

Example 113

(S,S)-4-(2,5-Diaza-bicyclo[2.2.1]hept-2-yl)-8-methoxy-benzo[4,5]furo[3,2-d]pyrimidin-2-ylamine trifluoroacetic acid salt

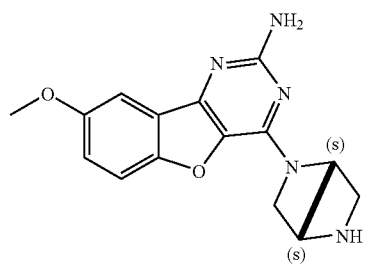

MS (ESI): mass calcd. for $C_{16}H_{17}N_5O_2$, 311.1; m/z found, 312.1 [M+H]⁺. ¹H NMR, (CD₃OD): 7.71-7.60 (m, 1H), 7.55-7.47 (m, 1H), 7.39-7.32 (m, 1H), 5.86-5.70 (m, 1H), 5.57-5.39 (m, 1H), 4.76-4.59 (m, 1H), 4.50-4.23 (m, 1H), 4.13-3.85 (m, 4H), 3.72-3.50 (m, 2H), 2.51-2.16 (m, 2H).

Example 114

(cis)-4-(Hexahydro-pyrrolo[3,4-b]pyrrol-5-yl)-8-methoxy-benzo[4,5]furo[3,2-d]pyrimidin-2-ylamine trifluoroacetic acid salt

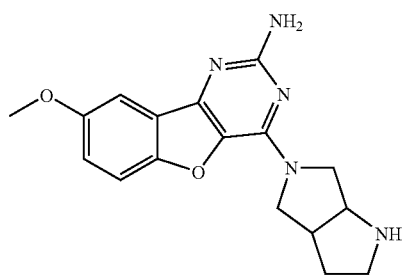

MS (ESI): mass calcd. for $C_{17}H_{19}N_5O_2$, 325.1; m/z found, 326.2 [M+H]⁺. ¹H NMR (CD₃OD): 7.65 (d, J=9.22 Hz, 1H), 7.53-7.46 (m, 1H), 7.41-7.30 (m, 1H), 4.65-4.44 (m, 2H), 4.26-4.00 (m, 2H), 3.92 (s, 3H), 3.84-3.80 (m, 1H), 3.60-3.37 (m, 3H), 2.48-2.35 (m, 1H), 2.20-2.07 (m, 1H).

Example 115

2-[8-Chloro-4-(4-methyl-piperazin-1-yl)-benzo[4,5]furo[3,2-d]pyrimidin-2-ylamino]-ethanol MS (ESI): mass calcd. for $C_{17}H_{20}ClN_5O_2$, 361.8; m/z found, 362.1 [M+H]⁺. ¹H NMR (CD₃OD): 7.97 (d, J=1.64 Hz, 1H), 7.49-7.39 (m, 2H), 5.23 (t, J=5.80 Hz, 1H), 4.10-3.98 (m, 4H), 3.90-3.84 (m, 2H), 3.65-3.59 (m, 2H), 2.61-2.50 (m, 4H), 2.36 (s, 3H).

Example 116

2-[4-(4-Methyl-piperazin-1-yl)-benzo[4,5]furo[3,2-d]pyrimidin-2-ylamino]-ethanol

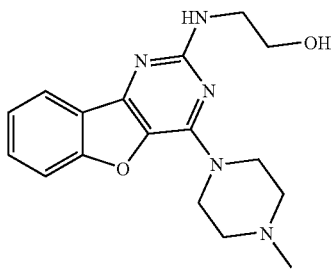

MS (ESI): mass calcd. for $C_{17}H_{21}N_5O_2$, 327.4; m/z found, 328.2 [M+H]+. $^1$H NMR (CD$_3$OD): 8.01 (d, J=7.68 Hz, 1H), 7.56-7.48 (m, 2H), 7.38-7.32 (m, 1H), 5.27 (t, J=5.63 Hz, 1H), 4.11-4.02 (m, 4H), 3.91-3.85 (m, 2H), 3.66-3.60 (m, 2H), 2.60-2.54 (m, 4H), 2.38 (s, 3H).

Example 117

(cis)-2-[8-Chloro-4-(octahydro-pyrrolo[3,4-b]pyridin-6-yl)-benzo[4,5]furo[3,2-d]pyrimidin-2-ylamino]-ethanol

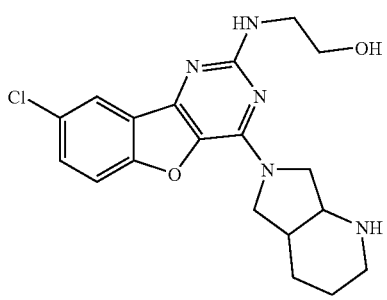

MS (ESI): mass calcd. for $C_{19}H_{22}ClN_5O_2$, 387.8; m/z found, 388.2 [M+H]+. $^1$H NMR (CDCl$_3$): 7.97-7.94 (m, 1H), 7.47-7.39 (m, 2H), 5.27-5.21 (m, 1H), 4.18-3.96 (m, 2H), 3.91-3.81 (m, 2H), 3.81-3.55 (m, 4H), 3.06-2.99 (m, 1H), 2.75-2.65 (m, 1H), 2.48-2.27 (m, 1H), 1.93-1.47 (m, 5H).

Example 118

2-[8-Methoxy-4-(4-methyl-piperazin-1-yl)-benzo[4,5]furo[3,2-d]pyrimidin-2-ylamino]-ethanol

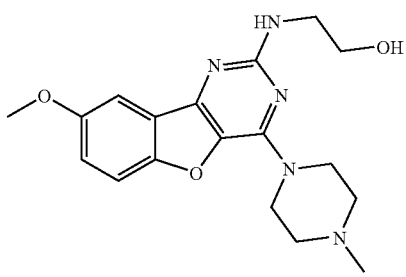

MS (ESI): mass calcd. for $C_{18}H_{23}N_5O_3$, 357.4; m/z found, 358.2 [M+H]+. $^1$H NMR (CDCl$_3$): 7.42-7.37 (m, 2H), 7.14-7.12 (m, 1H), 5.27-5.22 (m, 1H), 4.11-4.03 (m, 4H), 3.92-3.86 (m, 5H), 3.67-3.61 (m, 2H), 2.59-2.53 (m, 4H), 2.38 (s, 3H).

Example 119

[8-Chloro-4-(4-methyl-piperazin-1-yl)-benzo[4,5]furo[3,2-d]pyrimidin-2-yl]-cyclopropyl-amine

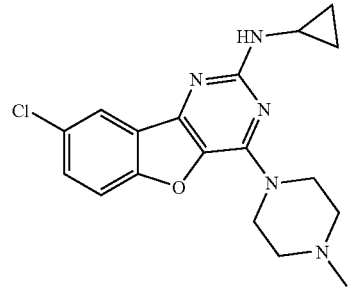

MS (ESI): mass calcd. for $C_{18}H_{20}ClN_5O$, 357.8; m/z found, 358.1 [M+H]+. $^1$H NMR (CDCl$_3$): 8.02 (d, J=2.03 Hz, 1H), 7.47-7.38 (m, 2H), 4.12-3.97 (m, 4H), 2.84-2.76 (m, 1H), 2.59-2.53 (m, 4H), 2.36 (s, 3H), 0.80-0.73 (m, 2H), 0.57-0.52 (m, 2H).

Example 120

[8-Chloro-4-(4-methyl-piperazin-1-yl)-benzo[4,5]furo[3,2-d]pyrimidin-2-yl]-isobutyl-amine

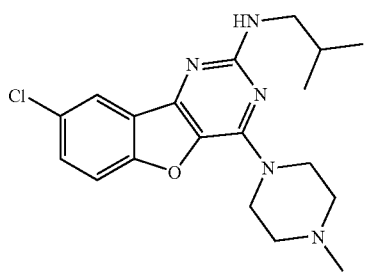

MS (ESI): mass calcd. for $C_{19}H_{24}ClN_5O$, 373.8; m/z found, 374.2 [M+H]+. $^1$H NMR (CDCl$_3$): 8.03 (d, J=2.06 Hz, 1H), 7.47-7.39 (m, 2H), 4.12-4.04 (m, 4H), 3.28-3.23 (m, 2H), 2.62-2.55 (m, 4H), 2.38 (s, 3H), 1.95-1.87 (m, 1H), 0.98 (d, J=6.71 Hz, 6H).

Example 121

Allyl-[8-chloro-4-(4-methyl-piperazin-1-yl)-benzo[4,5]furo[3,2-d]pyrimidin-2-yl]-amine

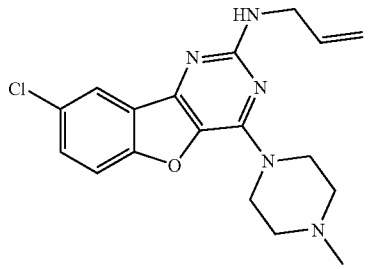

MS (ESI): mass calcd. for $C_{18}H_{20}ClN_5O$, 357.8; m/z found, 358.2 [M+H]+. 1H NMR (CDCl3): 8.02 (d, J=2.06 Hz, 1H), 7.48-7.37 (m, 2H), 6.03-5.92 (m, 1H), 5.28-5.24 (m, 1H), 5.15-5.11 (m, 1H), 4.12-4.02 (m, 4H), 2.62-2.56 (m, 4H), 2.38 (s, 3H).

Example 122

N1-[8-Chloro-4-(4-methyl-piperazin-1-yl)-benzo[4,5]furo[3,2-d]pyrimidin-2-yl]-propane-1,3-diamine

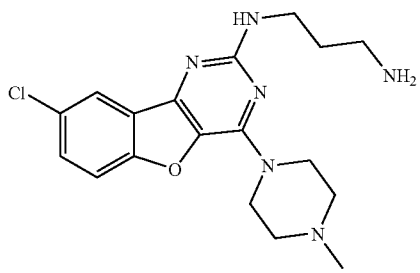

MS (ESI): mass calcd. for $C_{17}H_{21}ClN_6O$, 360.8; m/z found, 361.2 [M+H]+. 1H NMR (CDCl3): 8.00 (d, J=2.03 Hz, 1H), 7.49-7.40 (m, 2H), 5.09 (t, J=5.91 Hz, 1H), 4.12-3.98 (m, 4H), 3.54 (dd, J=11.90, 5.97 Hz, 1H), 2.97 (t, J=5.94 Hz, 2H), 2.58-2.54 (m, 4H), 2.38 (s, 3H).

Example 123

[8-Chloro-4-(4-methyl-piperazin-1-yl)-benzo[4,5]furo[3,2-d]pyrimidin-2-yl]-(2-methylsulfanyl-ethyl)-amine

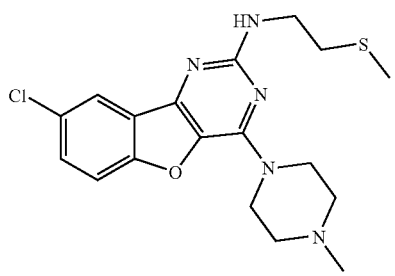

MS (ESI): mass calcd. for $C_{18}H_{22}ClN_5OS$, 391.9; m/z found, 392.2 [M+H]+. 1H NMR (CDCl3): 8.02 (d, J=2.07 Hz, 1H), 7.49-7.39 (m, 2H), 4.14-4.05 (m, 4H), 3.65 (m, 2H), 2.80-2.74 (m, 2H), 2.66-2.58 (m, 4H), 2.40 (s, 3H).

Example 124

[8-Chloro-4-(4-methyl-piperazin-1-yl)-benzo[4,5]furo[3,2-d]pyrimidin-2-yl]-methyl-amine

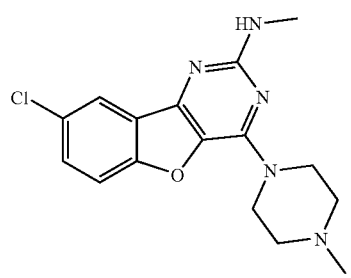

MS (ESI): mass calcd. for $C_{16}H_{18}ClN_5O$, 331.8; m/z found, 332.1 [M+H]+. 1H NMR (CDCl3): 8.01 (d, J=1.66 Hz, 1H), 7.47-7.38 (m, 2H), 4.83-4.75 (m, 1H), 4.13-3.98 (m, 4H), 3.02 (d, J=5.07 Hz, 3H), 2.58-2.53 (m, 4H), 2.37 (s, 3H).

Example 125

(S,S)-2-[8-Chloro-4-(2,5-diaza-bicyclo[2.2.1]hept-2-yl)-benzo[4,5]furo[3,2-d]pyrimidin-2-ylamino]-ethanol

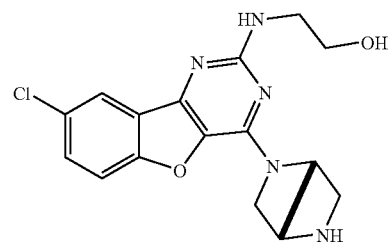

MS (ESI): mass calcd. for $C_{17}H_{18}ClN_5O_2$, 359.8; m/z found, 360.1 [M+H]+. 1H NMR (CDCl3): 7.98 (d, J=2.00 Hz, 1H), 7.49-7.41 (m, 2H), 5.30-5.25 (m, 1H), 3.91 (s, 1H), 3.89-3.86 (m, 2H), 3.68-3.55 (m, 2H), 3.25-3.09 (m, 2H), 2.02-1.88 (m, 2H).

Example 126

2-[8-Chloro-4-(3-methylamino-pyrrolidin-1-yl)-benzo[4,5]furo[3,2-d]pyrimidin-2-ylamino]-ethanol

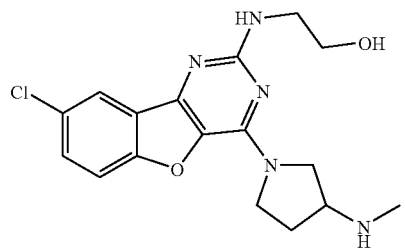

MS (ESI): mass calcd. for $C_{17}H_{20}ClN_5O_2$, 361.8; m/z found, 362.1 [M+H]+. 1H NMR (CDCl3): 7.97 (d, J=2.07 Hz, 1H), 7.47-7.39 (m, 2H), 5.29-5.24 (m, 1H), 3.92-3.84 (m, 3H), 3.65-3.59 (m, 3H), 3.46-3.39 (m, 1H), 2.53 (s, 3H), 2.28-2.15 (m, 1H), 1.98-1.87 (m, 1H), 1.72-1.48 (m, 2H).

Example 127

2-[8-Chloro-4-(4-methyl-[1,4]diazepan-1-yl)-benzo[4,5]furo[3,2-d]pyrimidin-2-ylamino]-ethanol

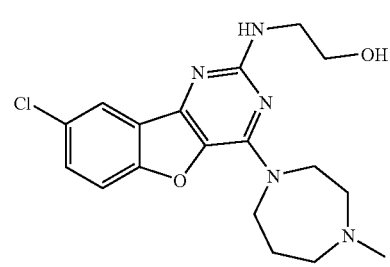

MS (ESI): mass calcd. for $C_{18}H_{22}ClN_5O_2$, 375.8; m/z found, 376.2 [M+H]$^+$. $^1$H NMR (CDCl$_3$): 7.97 (d, J=1.69 Hz, 1H), 7.47-7.38 (m, 2H), 5.22 (t, J=5.70 Hz, 1H), 4.17-3.92 (m, 4H), 3.90-3.82 (m, 2H), 3.65-3.56 (m, 2H), 2.82-2.72 (m, 2H), 2.63-2.54 (m, 2H), 2.40 (s, 3H), 2.12-2.00 (m, 2H).

Example 128

8-Chloro-4-(3,5-dimethyl-piperazin-1-yl)-benzo[4,5]furo[3,2-d]pyrimidin-2-ylamine trifluoroacetic acid salt

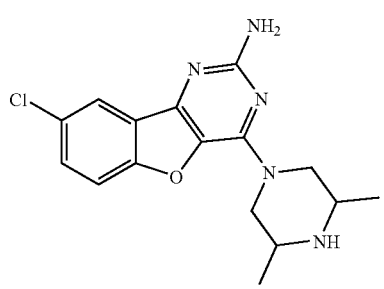

The title compound was prepared as a mixture of cis- and trans-stereoisomers. MS (ESI): mass calcd. for $C_{16}H_{18}N_5ClO$, 331.8; m/z found, 332.2 [M+H]$^+$. $^1$H NMR (CD$_3$OD): 7.98 (d, J=1.88 Hz, 1H), 7.65 (dt, J=9.00, 5.48 Hz, 2H), 5.16 (dd, J=14.43, 2.11 Hz, 2H), 3.49 (ddd, J=11.47, 6.67, 3.50 Hz, 2H), 1.37 (d, J=6.56 Hz, 6H).

Example 129

4-(3-Amino-azetidin-1-yl)-8-chloro-benzo[4,5]furo[3,2-d]pyrimidin-2-ylamine trifluoroacetic acid salt

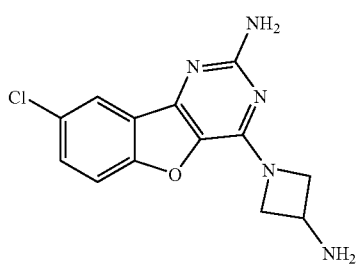

MS (ESI): mass calcd. for $C_{13}H_{12}N_5ClO$, 289.7; m/z found, 290.1 [M+H]$^+$. $^1$H NMR (DMSO-d$_6$): 9.11-8.51 (m, 1H), 7.98 (s, 1H), 7.82 (d, J=8.95 Hz, 1H), 7.69 (dd, J=8.96, 1.61 Hz, 1H), 7.39-7.03 (m, 1H), 4.78-4.54 (m, 2H), 4.51-4.34 (m, 2H), 4.34-4.22 (m, 2H).

Example 130

(2S,5R)-8-Chloro-4-(2,5-dimethyl-piperazin-1-yl)-benzo[4,5]furo[3,2-d]pyrimidin-2-ylamine trifluoroacetic acid salt

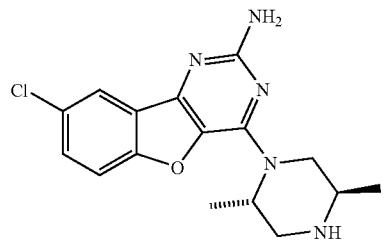

MS (ESI): mass calcd. for $C_{16}H_{18}N_5ClO$, 331.8; m/z found, 332.2 [M+H]$^+$. $^1$H NMR (CD$_3$OD): 8.00-7.96 (m, 1H), 7.66-7.64 (m, 2H), 5.40-5.28 (m, 1H), 3.97-3.70 (m, 2H), 3.59 (dd, J=13.59, 5.24 Hz, 1H), 1.48 (d, J=7.00 Hz, 1H), 1.38 (d, J=6.91 Hz, 1H).

Example 131

(S)-8-Chloro-4-(2-methyl-piperazin-1-yl)-benzo[4,5]furo[3,2-d]pyrimidin-2-ylamine trifluoroacetic acid salt

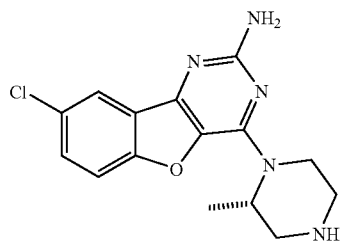

MS (ESI): mass calcd. for $C_{15}H_{16}N_5ClO$, 317.8; m/z found, 318.1 [M+H]$^+$. $^1$H NMR (CD$_3$OD): 8.13-8.03 (m, 1H), 7.83-7.64 (m, 2H), 5.60-5.47 (m, 1H), 5.22-5.14 (m, 1H), 3.84-3.70 (m, 1H), 3.63-3.55 (m, 1H), 3.53-3.44 (m, 2H), 3.39-3.32 (m, 1H), 1.57 (d, J=7.12 Hz, 3H).

Example 132

(R)-8-Chloro-4-(2-methyl-piperazin-1-yl)-benzo[4,5]furo[3,2-d]pyrimidin-2-ylamine trifluoroacetic acid salt

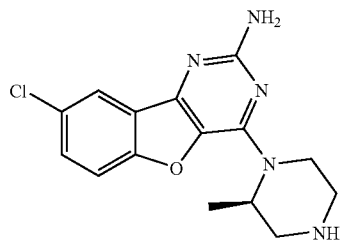

MS (ESI): mass calcd. for $C_{15}H_{16}N_5ClO$, 317.8; m/z found, 318.1 [M+H]$^+$. $^1$H NMR (CD$_3$OD): 8.03-7.93 (m, 1H), 7.71-7.57 (m, 2H), 5.53-5.37 (m, 1H), 5.16-5.03 (m, 1H), 3.79-3.59 (m, 1H), 3.49 (d, J=12.83 Hz, 1H), 3.43-3.35 (m, 2H), 3.31-3.23 (m, 1H), 1.48 (d, J=7.12 Hz, 3H).

Example 133

(S)-8-Chloro-4-(5-methyl-piperazin-1-yl)-benzo[4,5]furo[3,2-d]pyrimidin-2-ylamine trifluoroacetic acid salt

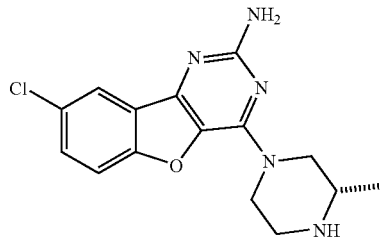

MS (ESI): mass calcd. for $C_{15}H_{16}N_5ClO$; 317.8; m/z found, 318.1 [M+H]$^+$. $^1$H NMR (CD$_3$OD): 8.10-8.02 (m, 1H), 7.79-7.70 (m, 2H), 5.11 (t, J=13.80 Hz, 1H), 3.88-3.68 (m, 1H), 3.70-3.44 (m, 1H), 3.38 (dt, J=12.98, 12.88, 3.29 Hz, 1H), 1.46 (d, J=6.42 Hz, 3H).

Example 134

(R)-8-Chloro-4-(5-methyl-piperazin-1-yl)-benzo[4,5]furo[3,2-d]pyrimidin-2-ylamine trifluoroacetic acid salt

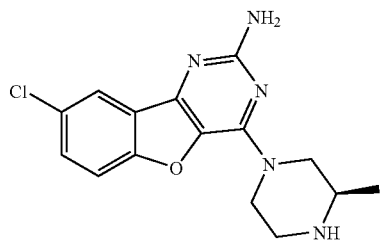

MS (ESI): mass calcd. for $C_{15}H_{16}N_5ClO$, 317.8; m/z found, 318.1 [M+H]$^+$. $^1$H NMR (CD$_3$OD): 8.12-8.03 (m, 1H), 7.82-7.71 (m, 2H), 5.22-5.05 (m, 2H), 3.91-3.70 (m, 1H), 3.69-3.47 (m, 3H), 3.44-3.32 (m, 1H), 1.31 (d, J=7.16 Hz, 1H).

Example 135

9-Fluoro-4-(4-methyl-piperazin-1-yl)-benzo[4,5]furo[3,2-d]pyrimidin-2-ylamine trifluoroacetic acid salt

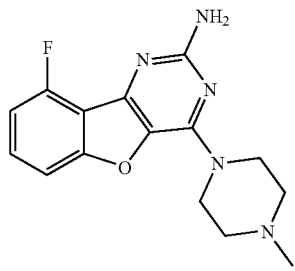

MS (ESI): mass calcd. for $C_{15}H_{16}N_5FO$; 301.3; m/z found, 302.2 [M+H]$^+$. $^1$H NMR (CD$_3$OD): 7.68 (td, J=8.38, 5.51 Hz, 1H), 7.51 (d, J=8.27 Hz, 1H), 7.22-7.16 (m, 1H), 3.61-3.28 (m, 4H), 2.90 (s, 3H).

Example 136

(R)-9-Fluoro-4-(3-methylamino-pyrrolidin-1-yl)-benzo[4,5]furo[3,2-d]pyrimidin-2-ylamine trifluoroacetic acid salt

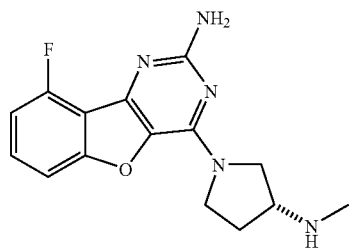

MS (ESI): mass calcd. for $C_{15}H_{16}N_5FO$, 301.3; m/z found, 302.2 [M+H]$^+$. $^1$H NMR (CD$_3$OD): 7.66 (td, J=8.31, 5.54 Hz, 1H), 7.51 (d, J=8.57 Hz, 1H), 7.26-7.11 (m, 1H), 4.61-3.68 (m, 5H), 2.75 (s, 3H), 2.67-2.15 (m, 2H).

Example 137

9-Fluoro-4-piperazin-1-yl-benzo[4,5]furo[3,2-d]pyrimidin-2-ylamine trifluoroacetic acid salt

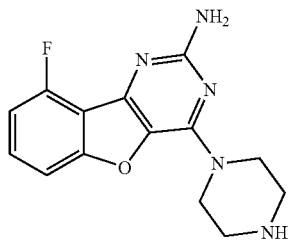

MS (ESI): mass calcd. for $C_{14}H_{14}N_5FO$, 287.3; m/z found, 288.2 [M+H]$^+$. $^1$H NMR (CD$_3$OD): 7.76 (dt, J=8.37, 5.50 Hz, 1H), 7.60 (d, J=8.24 Hz, 1H), 7.32-7.23 (m, 1H), 4.64-4.29 (m, 4H), 3.53-3.38 (m, 3H).

Example 138

4-(3-Amino-azetidin-1-yl)-9-fluoro-benzo[4,5]furo[3,2-d]pyrimidin-2-ylamine trifluoroacetic acid salt

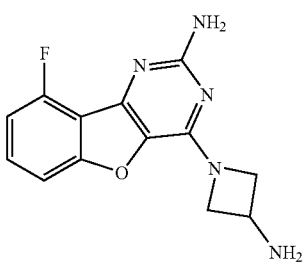

MS (ESI): mass calcd. for $C_{13}H_{12}N_5FO$, 273.3, m/z found, 374.1 [M+H]+. 1H NMR (CD3OD): 7.79-7.71 (m, 1H), 7.64-7.52 (m, 1H), 7.33-7.24 (m, 1H), 5.08-4.85 (m, 2H), 4.73-4.50 (m, 2H), 4.50-4.35 (m, 1H).

Example 139

4-(4-Methyl-piperazin-1-yl)-8-trifluoromethyl-benzo[4,5]furo[3,2-d]pyrimidin-2-ylamine trifluoroacetic acid salt

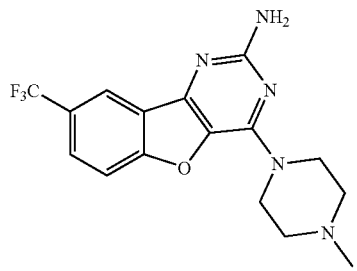

MS (ESI): mass calcd. for $C_{16}H_{16}F_3N_5O$, 351.3; m/z found, 352.1 [M+H]+. 1H NMR (CD3OD): 8.36 (s, 1H), 7.95 (dd, J=8.96, 1.77 Hz, 1H), 7.85 (d, J=8.89 Hz, 1H), 3.59-3.30 (m, 4H), 2.91 (s, 3H).

Example 140

(R)-4-(3-Methylamino-pyrrolidin-1-yl)-8-trifluoromethyl-benzo[4,5]furo[3,2-d]pyrimidin-2-ylamine trifluoroacetic acid salt

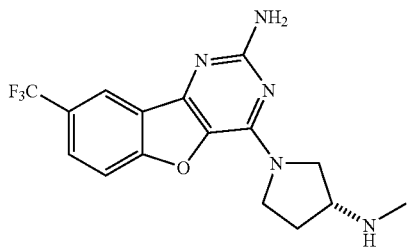

MS (ESI): mass calcd. for $C_{16}H_{16}N_5F_3O$, 351.1; m/z found, 352.1 [M+H]+. 1H NMR (CD3OD): 8.35 (s, 1H), 7.94 (dd, J=8.99, 1.69 Hz, 1H), 7.85 (d, J=8.88 Hz, 1H), 4.59-3.73 (m, 5H), 2.76 (s, 3H), 2.65-2.08 (m, 2H).

Example 141

(S)-4-(3-Amino-piperidin-1-yl)-8-trifluoromethyl-benzo[4,5]furo[3,2-d]pyrimidin-2-ylamine trifluoroacetic acid salt

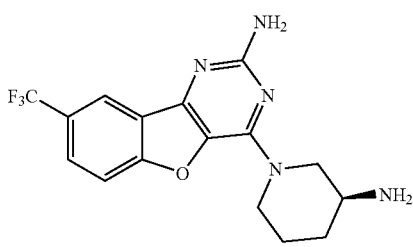

MS (ESI): mass calcd. for $C_{16}H_{16}N_5F_3O$, 351.3; m/z found, 352.1 [M+H]+. 1H NMR (CD3OD): 8.46 (s, 1H), 8.04 (dd, J=8.94, 1.62 Hz, 1H), 7.96 (d, J=8.90 Hz, 1H), 4.62-4.52 (m, 1H), 3.96 (dd, J=13.56, 8.28 Hz, 2H), 3.62-3.50 (m, 1H), 2.38-2.16 (m, 1H), 2.10-1.96 (m, 1H), 1.96-1.80 (m, 2H).

Example 142

4-Piperazin-1-yl-8-trifluoromethyl-benzo[4,5]furo[3,2-d]pyrimidin-2-ylamine trifluoroacetic acid salt

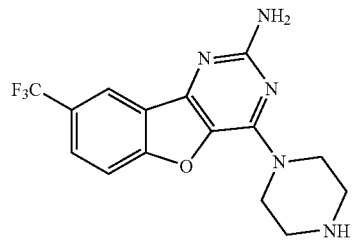

MS (ESI): mass calcd. for $C_{15}H_{14}N_5F_3O$, 337.3; m/z found, 338.2 [M+H]+. 1H NMR (CD3OD): 8.47 (s, 1H), 8.04 (dd, J=9.02, 1.71 Hz, 1H), 7.94 (d, J=8.89 Hz, 1H), 4.54-4.43 (m, 4H), 3.57-3.39 (m, 4H).

Example 143

(S,S)-4-(2,5-Diaza-bicyclo[2.2.1]hept-2-yl)-8-trifluoromethyl-benzo[4,5]furo[3,2-d]pyrimidin-2-ylamine citrate salt

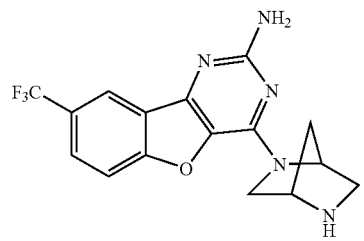

MS (ESI): mass calcd. for $C_{16}H_{14}N_5F_3O$, 349.3, m/z found, 350.1 [M+H]+. 1H NMR (CDCl3): 8.35 (s, 1H), 7.76 (dd, J=8.72, 1.31 Hz, 1H), 7.60 (d, J=8.79 Hz, 1H), 5.47-5.04 (m, 1H), 4.85-4.65 (m, 2H), 3.99-3.83 (m, 1H), 3.80-3.45 (m, 1H), 3.31-3.02 (m, 2H), 2.10-1.79 (m, 2H), 1.75-1.40 (m, 3H).

Example 144

4-(3-Amino-azetidin-1-yl)-8-trifluoromethyl-benzo[4,5]furo[3,2-d]pyrimidin-2-ylamine

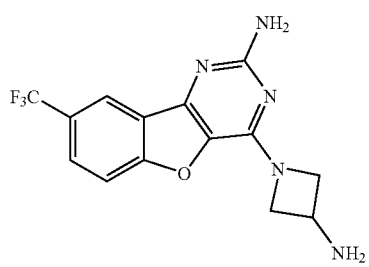

MS (ESI): mass calcd. for $C_{14}H_{12}N_5F_3O$, 323.3; m/z found, 324.1 [M+H]$^+$. $^1$H NMR (CD$_3$OD): 8.43 (s, 1H), 8.04-7.95 (m, 1H), 7.90 (d, J=8.51 Hz, 1H), 5.00-4.87 (m, 2H), 4.71-4.52 (m, 2H), 4.48-4.38 (m, 1H).

Example 145

8,9-Difluoro-4-(4-methyl-piperazin-1-yl)-benzo[4,5]furo[3,2-d]pyrimidin-2-ylamine trifluoroacetic acid salt

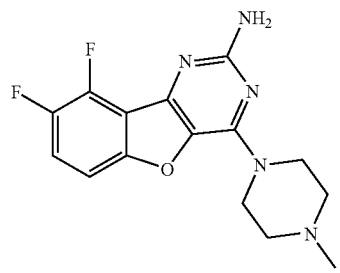

MS (ESI): mass calcd. for $C_{15}H_{15}N_5F_2O$, 319.3; m/z found, 320.2 [M+H]$^+$. $^1$H NMR (CD$_3$OD): 7.63-7.55 (m, 1H), 7.31-7.16 (m, 1H), 3.87-3.35 (m, 4H), 3.00 (s, 3H).

Example 146

8,9-Difluoro-4-piperazin-1-yl-benzo[4,5]furo[3,2-d]pyrimidin-2-ylamine trifluoroacetic acid salt

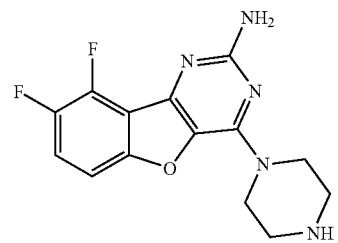

MS (ESI): mass calcd. for $C_{14}H_{13}N_5F_2O$, 305.3; m/z found, 306.2 [M+H]$^+$. $^1$H NMR (CD$_3$OD): 7.61-7.52 (m, 1H), 7.25 (dt, J=8.99, 2.79 Hz, 1H), 4.51-4.34 (m, 4H), 3.57-3.39 (m, 4H).

Example 147

(S)-4-(3-Amino-piperidin-1-yl)-8,9-difluoro-benzo[4,5]furo[3,2-d]pyrimidin-2-ylamine trifluoroacetic acid salt

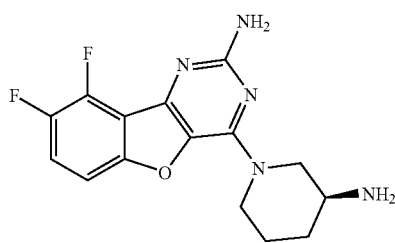

MS (ESI): mass calcd. for $C_{15}H_{15}N_5F_2O$, 319.2; m/z found, 320.2 [M+H]$^+$. $^1$H NMR (CD$_3$OD): 7.67-7.48 (m, 1H), 7.32-7.17 (m, 1H), 4.81-4.66 (m, 1H), 4.59-4.44 (m, 1H), 4.10-3.80 (m, 2H), 3.56 (td, J=11.95, 3.91 Hz, 1H), 2.36-2.15 (m, 1H), 2.13-1.96 (m, 1H), 1.96-1.74 (m, 2H).

Example 148

(R)-8,9-Difluoro-4-(3-methylamino-pyrrolidin-1-yl)-benzo[4,5]furo[3,2-d]pyrimidin-2-ylamine trifluoroacetic acid salt

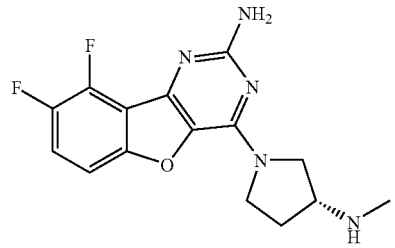

MS (ESI): mass calcd. for $C_{15}H_{15}N_5F_2O$, 319.3; m/z found, 320.2 [M+H]$^+$. $^1$H NMR (CD$_3$OD): 7.66-7.45 (m, 1H), 7.25 (dt, J=8.97, 2.77 Hz, 1H), 4.73-3.83 (m, 5H), 2.84 (s, 3H), 2.73-2.19 (m, 2H).

Example 149

(S,S)-4-(2,5-Diaza-bicyclo[2.2.1]hept-2-yl)-8,9-difluoro-benzo[4,5]furo[3,2-d]pyrimidin-2-ylamine trifluoroacetic acid salt

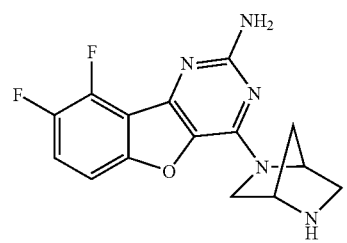

MS (ESI): mass calcd. for $C_{15}H_{13}N_5F_2O$, 317.3; m/z found, 318.2 [M+H]$^+$. $^1$H NMR (CD$_3$OD): 7.63-7.48 (m, 1H), 7.25 (dt, J=8.97, 2.72 Hz, 1H), 5.84-5.33 (m, 1H), 4.70 (s, 1H), 4.60-3.81 (m, 2H), 3.85-3.37 (m, 2H), 2.54-2.11 (m, 2H).

Example 150

4-(3-Amino-azetidin-1-yl)-8,9-difluoro-benzo[4,5]furo[3,2-d]pyrimidin-2-ylamine trifluoroacetic acid salt

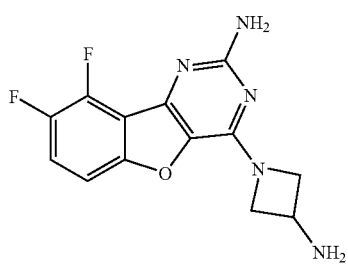

MS (ESI): mass calcd. for $C_{13}H_{11}N_5F_2O$, 291.3; m/z found, 292.1 [M+H]+. 1H NMR (CD3OD): 7.67-7.46 (m, 1H), 7.25 (dt, J=8.97, 2.76 Hz, 1H), 5.16-4.86 (m, 2H), 4.75-4.53 (m, 2H), 4.51-4.37 (m, 1H).

Example 151

9-Chloro-4-(4-methyl-piperazin-1-yl)-benzo[4,5]furo[3,2-d]pyrimidin-2-ylamine trifluoroacetic acid salt

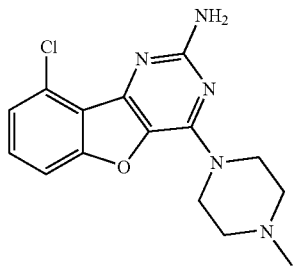

MS (ESI): mass calcd. for $C_{15}H_{16}N_6ClO$, 317.8; m/z found, 318.1 [M+H]+. 1H NMR (CD3OD): 7.74-7.58 (m, 1H), 7.50-7.44 (m, 1H), 3.72-3.29 (m, 4H), 2.90 (s, 3H).

Example 152

(R)-9-Chloro-4-(3-methylamino-pyrrolidin-1-yl)-benzo[4,5]furo[3,2-d]pyrimidin-2-ylamine trifluoroacetic acid salt

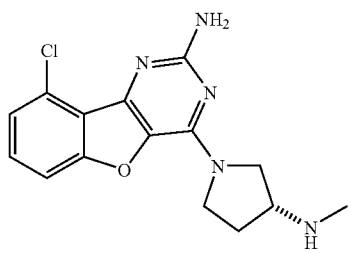

MS (ESI): mass calcd. for $C_{15}H_{16}N_5ClO$, 317.8; m/z found, 318.1 [M+H]+. 1H NMR (CD3OD): 7.86-7.75 (m, 2H), 7.69-7.59 (m, 1H), 4.72-4.35 (m, 2H), 4.33-3.95 (m, 3H), 2.93 (s, 2H).

Example 153

9-Chloro-4-piperazin-1-yl-benzo[4,5]furo[3,2-d]pyrimidin-2-ylamine trifluoroacetic acid salt

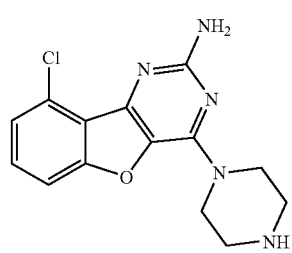

MS (ESI): mass calcd. for $C_{14}H_{14}N_5ClO$, 303.8; m/z found, 304.1 [M+H]+. 1H NMR (CD3OD): 7.64-7.49 (m, 2H), 7.25 (dt, J=8.99, 2.79 Hz, 1H), 4.57-4.29 (m, 4H), 3.63-3.36 (m, 4H).

Example 154

(S)-4-(3-Amino-piperidin-1-yl)-9-chloro-benzo[4,5]furo[3,2-d]pyrimidin-2-ylamine trifluoroacetic acid salt

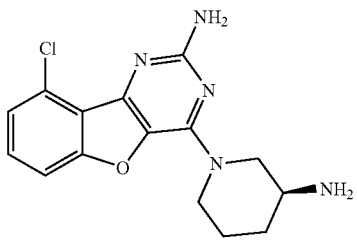

MS (ESI): mass calcd. for $C_{15}H_{16}N_5ClO$, 317.8; m/z found, 318.1 [M+H]+. 1H NMR (CD3OD): 7.80-7.69 (m, 2H), 7.64-7.51 (m, 1H), 4.65-4.51 (m, 1H), 3.97 (dd, J=13.53, 8.30 Hz, 2H), 3.64-3.49 (m, 1H), 2.34-2.16 (m, 1H), 2.10-1.97 (m, 1H), 1.95-1.77 (m, 2H).

Example 155

(S,S)-9-Chloro-4-(2,5-diaza-bicyclo[2.2.1]hept-2-yl)-benzo[4,5]furo[3,2-d]pyrimidin-2-ylamine trifluoroacetic acid salt

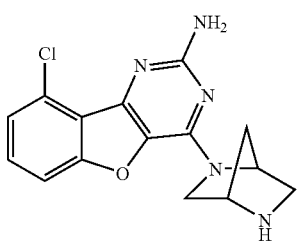

MS (ESI): mass calcd. for $C_{15}H_{14}N_5ClO$, 315.8; m/z found, 316.1 [M+H]+. 1H NMR (CD3OD): 7.83-7.62 (m, 2H), 7.62-7.49 (m, 1H), 5.95-5.24 (m, 1H), 4.70 (s, 1H), 4.51-3.88 (m, 2H), 3.79-3.46 (m, 2H), 2.51-2.11 (m, 2H).

Example 156

4-(3-Amino-azetidin-1-yl)-9-chloro-benzo[4,5]furo[3,2-d]pyrimidin-2-ylamine trifluoroacetic acid salt

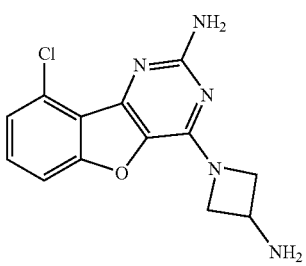

MS (ESI): mass calcd. for $C_{13}H_{12}N_5ClO$, 289.7; m/z found, 290.1 [M+H]+. 1H NMR (CD3OD): 7.75-7.64 (m, 1H), 7.61-7.47 (m, 1H), 5.04-4.86 (m, 2H), 4.72-4.55 (m, 2H), 4.52-4.30 (m, 1H).

Example 157

(R)-7-Methoxy-4-(3-methylamino-pyrrolidin-1-yl)-benzo[4,5]thieno[3,2-d]pyrimidin-2-ylamine trifluoroacetic acid salt

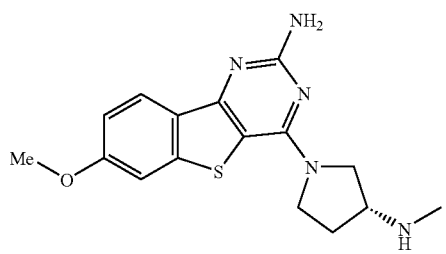

MS (ESI): mass calcd. for $C_{16}H_{19}N_5OS$, 329.4; m/z found, 330.0 [M+H]$^+$. $^1$H NMR (CD$_3$OD): 8.15 (d, J=9.03 Hz, 1H), 7.52 (d, J=2.21 Hz, 1H), 7.19 (dd, J=9.02, 2.28 Hz, 1H), 4.38-4.12 (m, 4H), 4.10-4.01 (m, 1H), 3.94 (s, 3H), 2.84 (s, 3H), 2.69-2.56 (m, 1H), 2.49-2.36 (m, 1H).

Example 158

(S)-7-Methoxy-4-(3-methylamino-pyrrolidin-1-yl)-benzo[4,5]thieno[3,2-d]pyrimidin-2-ylamine trifluoroacetic acid salt

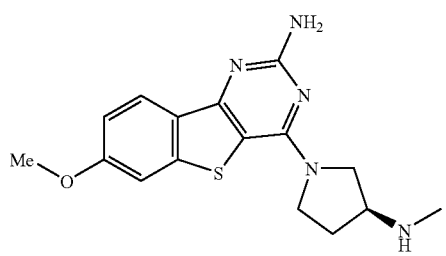

MS (ESI): mass calcd. for $C_{16}H_{19}N_5OS$, 329.4; m/z found, 330.0 [M+H]$^+$. $^1$H NMR (CD$_3$OD): 8.15 (d, J=9.06 Hz, 1H), 7.52 (d, J=2.21 Hz, 1H), 7.19 (dd, J=9.04, 2.28 Hz, 1H), 4.38-4.12 (m, 4H), 4.10-4.01 (m, 1H), 3.94 (s, 3H), 2.84 (s, 3H), 2.69-2.56 (m, 1H), 2.49-2.36 (m, 1H).

Example 159

7-Methoxy-4-(4-methyl-piperazin-1-yl)-benzo[4,5]thieno[3,2-d]pyrimidin-2-ylamine trifluoroacetic acid salt

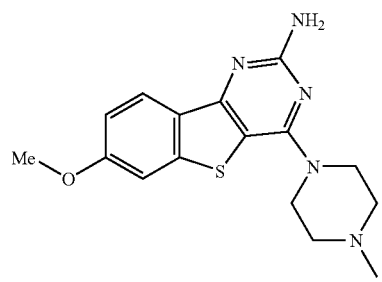

MS (ESI): mass calcd. for $C_{16}H_{19}N_5OS$, 329.4; m/z found, 330.1 [M+H]$^+$. $^1$H NMR (CD$_3$OD): 8.21 (d, J=9.01 Hz, 1H), 7.55 (d, J=2.20 Hz, 1H), 7.22 (dd, J=9.03, 2.27 Hz, 1H), 4.74-4.06 (m, 4H), 3.95 (s, 3H), 3.62-3.42 (m, 4H), 2.98 (s, 3H).

Example 160

2-(8-Chloro-4-piperazin-1-yl-benzo[4,5]furo[3,2-d]pyrimidin-2-ylamino)-ethanol

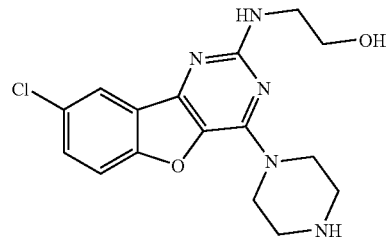

MS (ESI): mass calcd. for $C_{16}H_{18}ClN_5O_2$, 347.8; m/z found, 348.1 [M+H]$^+$. $^1$H NMR (CD$_3$OD): 8.12-8.07 (m, 1H), 7.69-7.65 (m, 2H), 4.43-4.37 (m, 4H), 3.80-3.74 (m, 2H), 3.66-3.59 (m, 2H), 2.50-2.41 (m, 4H).

Example 161

(S)-2-[4-(3-Amino-piperidin-1-yl)-8-chloro-benzo[4,5]furo[3,2-d]pyrimidin-2-ylamino]-ethanol

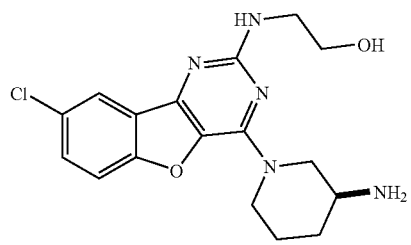

MS (ESI): mass calcd. for $C_{17}H_{20}ClN_5O_2$, 361.8; m/z found, 362.1 [M+H]$^+$. $^1$H NMR (CD$_3$OD): 8.12 (s, 1H), 7.76-7.70 (m, 2H), 5.14-4.98 (m, 2H), 4.56-4.44 (m, 2H), 4.14-4.04 (m, 2H), 3.85-3.72 (m, 3H), 3.67-3.53 (m, 5H), 3.10-2.97 (m, 2H).

Example 162

2-[4-(3-Amino-azetidin-1-yl)-8-chloro-benzo[4,5]furo[3,2-d]pyrimidin-2-ylamino]-ethanol

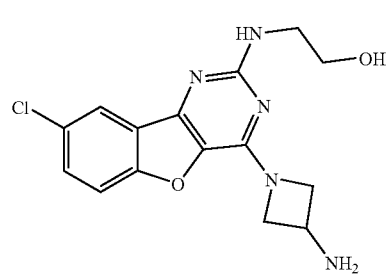

MS (ESI): mass calcd. for $C_{15}H_{16}ClN_5O_2$, 333.8; m/z found, 334.1 [M+H]$^+$. $^1$H NMR (CD$_3$OD): 8.07 (s, 1H), 7.69 (s, 2H), 4.87-4.85 (m, 2H), 4.69-4.59 (m, 2H), 4.47-4.32 (m, 1H), 3.76 (t, J=5.57 Hz, 2H), 3.60 (t, J=5.57 Hz, 2H).

Example 163

[8-Chloro-4-(4-methyl-piperazin-1-yl)-benzo[4,5]furo[3,2-d]pyrimidin-2-yl]-dimethyl-amine

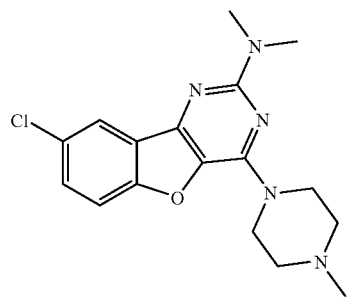

MS (ESI): mass calcd. for $C_{17}H_{20}ClN_5O_2$, 345.8; m/z found, 346.1 [M+H]$^+$. $^1$H NMR (CD$_3$OD): 8.28-8.27 (m, 1H), 7.73-7.70 (m, 2H), 3.54-3.47 (m, 4H), 3.34-3.31 (m, 9H), 3.01-2.89 (m, 4H).

Biological Testing:

Binding Assay on Recombinant Human Histamine H$_4$ Receptor

SK-N-MC cells or COS7 cells were transiently transfected with pH4R and grown in 150 cm$^2$ tissue culture dishes. Cells were washed with saline solution, scraped with a cell scraper and collected by centrifugation (1000 rpm, 5 min). Cell membranes were prepared by homogenization of the cell pellet in 20 mM Tris-HCl with a polytron tissue homogenizer for 10 sec at high speed. Homogenate was centrifuged at 1000 rpm for 5 min at 4° C. The supernatant was then collected and centrifuged at 20,000×g for 25 min at 4° C. The final pellet was resuspended in 50 mM Tris-HCl. Cell membranes were incubated with $^3$H-histamine (5-70 nM) in the presence or absence of excess histamine (10,000 nM). Incubation occurred at room temperature for 45 min. Membranes were harvested by rapid filtration over Whatman GF/C filters and washed 4 times with ice-cold 50 mM Tris HCl. Filters were then dried, mixed with scintillant and counted for radioactivity. SK-N-MC or COS7 cells expressing human histamine H$_4$ receptor were used to measure the affinity of binding of other compounds and their ability to displace $^3$H-ligand binding by incubating the above-described reaction in the presence of various concentrations of inhibitor or compound to be tested. For competition binding studies using $^3$H-histamine, $K_i$ values were calculated, based on an experimentally determined $K_D$ value of 5 nM and a ligand concentration of 5 nM, according to Y.-C. Cheng and W. H. Prusoff (Biochem. Pharmacol. 1973, 22(23):3099-3108): $K_i=(IC_{50})/(1+([L]/(K_D))$. Results for the compounds tested in this assay are presented in Table 1 as an average of results obtained.

TABLE 1

| Ex. | $K_i$ (nM) |
|---|---|
| 1 | 0.14 |
| 2 | 7.1 |

TABLE 1-continued

| Ex. | $K_i$ (nM) |
|---|---|
| 3 | 76 |
| 4 | 31 |
| 5 | 1.9 |
| 6 | 3.4 |
| 7 | 1.1 |
| 8 | 16 |
| 9 | 2.1 |
| 10 | 0.74 |
| 11 | 25 |
| 12 | 0.86 |
| 13 | 9.6 |
| 14 | 1.1 |
| 15 | 6.2 |
| 16 | 2.3 |
| 17 | 2.1 |
| 18 | 0.42 |
| 19 | 0.74 |
| 20 | 4.7 |
| 21 | 5.7 |
| 22 | 12 |
| 23 | 21 |
| 24 | 5.5 |
| 25 | 2.4 |
| 26 | 90 |
| 27 | 110 |
| 28 | 110 |
| 29 | 140 |
| 30 | 140 |
| 31 | 140 |
| 32 | 160 |
| 33 | 200 |
| 34 | 240 |
| 35 | 380 |
| 36 | 680 |
| 37 | 790 |
| 38 | >10000 |
| 39 | 2.3 |
| 40 | 44 |
| 41 | 110 |
| 42 | 71 |
| 43 | 87 |
| 44 | 29 |
| 45 | 4.8 |
| 46 | 28 |
| 47 | 100 |
| 48 | 2.1 |
| 49 | 350 |
| 50 | 1.0 |
| 51 | >10000 |
| 52 | 120 |
| 53 | >10000 |
| 54 | 440 |
| 55 | 43 |
| 56 | 25 |
| 57 | 150 |
| 58 | 300 |
| 59 | NT |
| 60 | 5.2 |
| 61 | 33 |
| 62 | 880 |
| 63 | 19 |
| 64 | 5.0 |
| 65 | 100 |
| 66 | 1.0 |
| 67 | 14 |
| 68 | 840 |
| 69 | 15 |
| 70 | 18.9 |
| 71 | 7.8 |
| 72 | 343 |
| 73 | 75 |
| 74 | 216 |
| 75 | 650 |
| 76 | 32 |
| 77 | 3230 |
| 78 | 22 |
| 79 | >10000 |
| 80 | 3.6 |

TABLE 1-continued

| Ex. | $K_i$ (nM) |
|---|---|
| 81 | 100 |
| 82 | 21 |
| 83 | 4.7 |
| 84 | >10000 |
| 85 | >10000 |
| 86 | 47 |
| 87 | >10000 |
| 88 | 30 |
| 89 | 12 |
| 90 | 120 |
| 91 | 50 |
| 92 | >10000 |
| 93 | >10000 |
| 94 | 880 |
| 95 | 140 |
| 96 | 2.8 |
| 97 | 42 |
| 98 | >10000 |
| 99 | 10 |
| 100 | 20 |
| 101 | 7.8 |
| 102 | 12 |
| 103 | 3.4 |
| 104 | 61 |
| 105 | 14 |
| 106 | 11 |
| 107 | 360 |
| 108 | 2.6 |
| 109 | 260 |
| 110 | 1820 |
| 111 | 330 |
| 112 | 41 |
| 113 | 420 |
| 114 | 91 |
| 115 | 4.3 |
| 116 | 68 |
| 117 | 930 |
| 118 | 200 |
| 119 | 350 |
| 120 | 3330 |
| 121 | 220 |
| 122 | 300 |
| 123 | 520 |
| 124 | 97 |
| 125 | 580 |
| 126 | 210 |
| 127 | 260 |
| 128 | >10000 |
| 129 | 19 |
| 130 | 140 |
| 131 | 60 |
| 132 | 120 |
| 133 | 5.7 |
| 134 | 50 |
| 135 | 21 |
| 136 | 10 |
| 137 | 150 |
| 138 | >10000 |
| 139 | 0.8 |
| 140 | 1.0 |
| 141 | 43 |
| 142 | 13 |
| 143 | 270 |
| 144 | >10000 |
| 145 | 160 |
| 146 | 1280 |
| 147 | >10000 |
| 148 | 39 |
| 149 | >10000 |
| 150 | 5380 |
| 151 | 74 |
| 152 | 87 |
| 153 | 1030 |
| 154 | >10000 |
| 155 | 460 |
| 156 | >10000 |
| 157 | 160 |
| 158 | 250 |
| 159 | 180 |
| 160 | >10000 |
| 161 | >10000 |
| 162 | >10000 |
| 163 | 718 |

While the invention has been illustrated by reference to examples, it is understood that the invention is intended not to be limited to the foregoing detailed description.

What is claimed is:

1. A chemical entity selected from compounds of Formula (I):

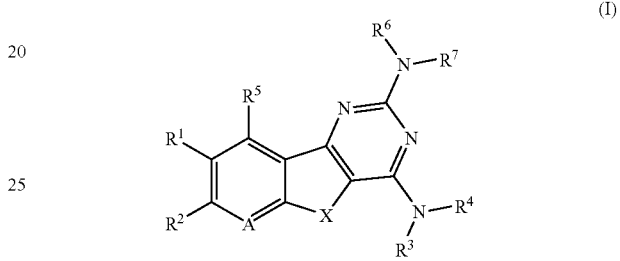

wherein
$R^1$ and $R^2$ are each independently H, Cl, F, Br, methyl, ethyl, methoxy, $NO_2$, or $CF_3$;
$R^5$ is H, methoxy, Cl, F, Br, or $CF_3$;
A is N or $CR^a$;
  where $R^a$ is H or Cl;
  with the proviso that at least two of $R^1$, $R^2$, $R^5$, and $R^a$ are H;
X is O or S;
—$N(R^3)R^4$ is one of the moieties:

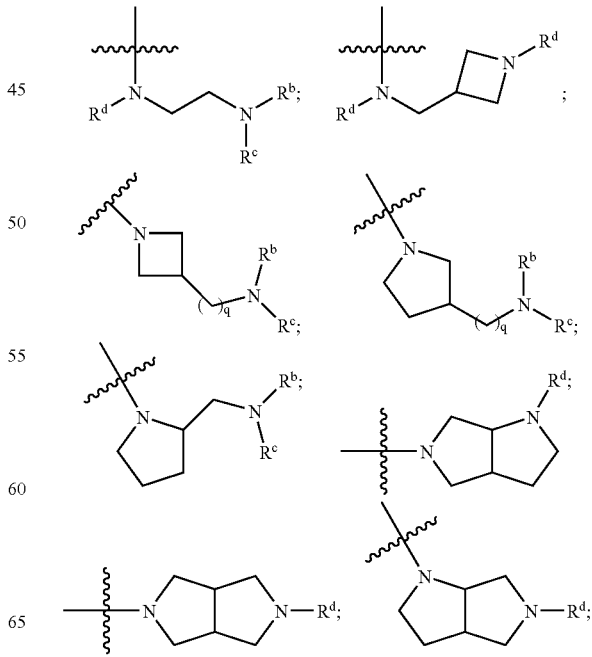

-continued

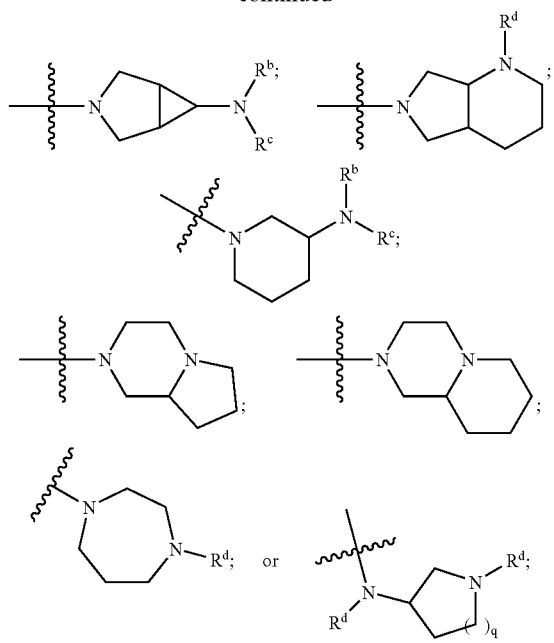

where q is 0 or 1;
$R^bR^c$ and $R^d$ are each independently H or $C_{1-3}$alkyl; and
each $R^e$ substitutent is methyl or two $R^e$ substituents taken together form a methylene or ethylene bridge;
$R^6$ is H or methyl;
$R^7$ is H; $C_{1-4}$alkyl unsubstituted or substituted with —OH, —SCH$_3$, or —NH$_2$; allyl; or cyclopropyl;
and pharmaceutically acceptable salts of compounds of Formula (I).

2. A chemical entity as defined in claim 1, wherein $R^1$ is H, methoxy, Cl, Br, F, or CF$_3$.

3. A chemical entity as defined in claim 1, wherein $R^2$ is H.

4. A chemical entity as defined in claim 1, wherein $R^5$ is H.

5. A chemical entity as defined in claim 1, wherein $R^5$ is H or CF$_3$.

6. A chemical entity as defined in claim 1, wherein A is N.

7. A chemical entity as defined in claim 1, wherein A is CR$^a$.

8. A chemical entity as defined in claim 7, wherein $R^a$ is H.

9. A chemical entity as defined in claim 1, wherein X is O.

10. A chemical entity as defined in claim 1, wherein X is S.

11. A chemical entity as defined in claim 1, wherein —N(R$^3$)R$^4$ is:

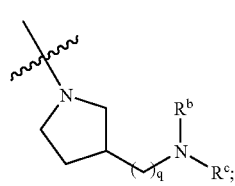

where q is 0.

12. A chemical entity as defined in claim 1, wherein —N(R$^3$)R$^4$ is:

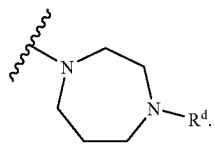

13. A chemical entity as defined in claim 1, wherein —N(R$^3$)R$^4$ is:

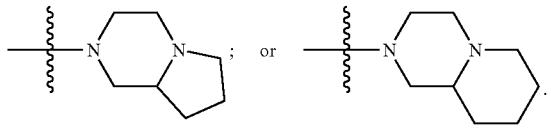

14. A chemical entity as defined in claim 1, wherein —N(R$^3$)R$^4$ is:

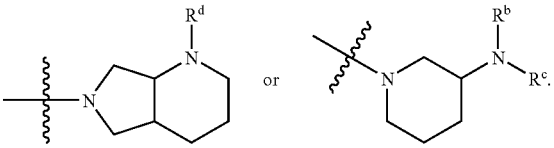

15. A chemical entity as defined in claim 1, wherein —N(R$^3$)R$^4$ is:

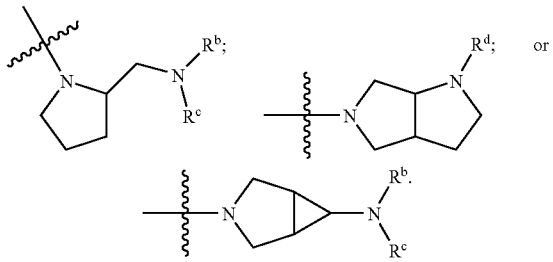

16. A chemical entity as defined in claim 1, wherein —N(R$^3$)R$^4$ is:

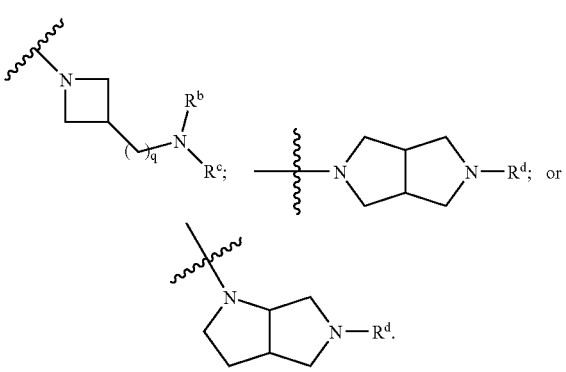

17. A chemical entity as defined in claim 1, wherein —N(R³)R⁴ is:

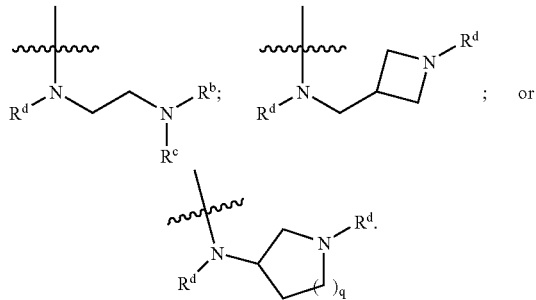

; or

18. A chemical entity as defined in claim 1, wherein R^b, R^C and R^d are each independently H or methyl.
19. A chemical entity as defined in claim 1, wherein R⁷ is H.
20. A chemical entity as defined in claim 1, wherein R⁷ is methyl, 2-hydroxyethyl, 2-methanesulfanylethyl, or 2-aminoethyl.
21. A chemical entity selected from:
  6,8-Dichloro-4-(octahydro-pyrrolo[3,4-b]pyridin-6-yl)-benzo[4,5]furo[3,2-d]pyrimidin-2-ylamine;
  8-Chloro-4-(4-isopropyl-[1,4]diazepan-1-yl)-benzo[4,5]furo[3,2-d]pyrimidin-2-ylamine;
  4-(3-Amino-pyrrolidin-1-yl)-6,8-dichloro-benzo[4,5]furo[3,2-d]pyrimidin-2-ylamine;
  (R)-6,8-Dichloro-4-(3-methylamino-pyrrolidin-1-yl)-benzo[4,5]furo[3,2-d]pyrimidin-2-ylamine;
  (R)-4-(3-Methylamino-pyrrolidin-1-yl)-benzo[4,5]furo[3,2-d]pyrimidin-2-ylamine;
  8-Chloro-4-[1,4]diazepan-1-yl-benzo[4,5]furo[3,2-d]pyrimidin-2-ylamine;
  8-Chloro-4-(octahydro-pyrido[1,2-a]pyrazin-2-yl)-benzo[4,5]furo[3,2-d]pyrimidin-2-ylamine;
  8-Chloro-4-(octahydro-pyrrolo[3,4-b]pyridin-6-yl)-benzo[4,5]furo[3,2-d]pyrimidin-2-ylamine;
  8-Chloro-4-(4-methyl-[1,4]diazepan-1-yl)-benzo[4,5]furo[3,2-d]pyrimidin-2-ylamine;
  (S,S)-8-Chloro-4-(2,5-diaza-bicyclo[2.2.1]hept-2-yl)-benzo[4,5]furo[3,2-d]pyrimidin-2-ylamine;
  8-Chloro-4-(3-methylamino-pyrrolidin-1-yl)-benzo[4,5]furo[3,2-d]pyrimidin-2-ylamine;
  (S)-4-(3-Amino-piperidin-1-yl)-8-chloro-benzo[4,5]furo[3,2-d]pyrimidin-2-ylamine;
  8-Chloro-4-(3-dimethylamino-pyrrolidin-1-yl)-benzo[4,5]furo[3,2-d]pyrimidin-2-ylamine;
  4-(3-Amino-pyrrolidin-1-yl)-8-chloro-benzo[4,5]furo[3,2-d]pyrimidin-2-ylamine;
  (S)-8-Chloro-4-(3-methylamino-pyrrolidin-1-yl)-benzo[4,5]furo[3,2-d]pyrimidin-2-ylamine;
  (R)-8-Chloro-4-(3-methylamino-pyrrolidin-1-yl)-benzo[4,5]furo[3,2-d]pyrimidin-2-ylamine;
  (R)-8-Bromo-4-(3-methylamino-pyrrolidin-1-yl)-benzo[4,5]furo[3,2-d]pyrimidin-2-ylamine;
  8-Bromo-4-(hexahydro-pyrrolo[1,2-a]pyrazin-2-yl)-benzo[4,5]furo[3,2-d]pyrimidin-2-ylamine;
  4-(3-Amino-pyrrolidin-1-yl)-benzo[4,5]furo[3,2-d]pyrimidin-2-ylamine;
  (R)-4-(3-Dimethylamino-pyrrolidin-1-yl)-benzo[4,5]furo[3,2-d]pyrimidin-2-ylamine;
  (R)-8-Chloro-4-(3-dimethylamino-pyrrol din-1-yl)-benzo[4,5]furo[3,2-d]pyrimidin-2-ylamine;
  (R)-4-(3-Amino-pyrrolidin-1-yl)-8-chloro-benzo[4,5]furo[3,2-d]pyrimidin-2-ylamine;
  (S)-4-(3-Aminomethyl-pyrrolidin-1-yl)-8-chloro-benzo[4,5]furo[3,2-d]pyrimidin-2-ylamine;
  8-Chloro-4-(hexahydro-pyrrolo[3,4-c]pyrrol-2-yl)-benzo[4,5]furo[3,2-d]pyrimidin-2-ylamine;
  (R)-4-(3-Amino-piperidin-1-yl)-8-chloro-benzo[4,5]furo[3,2-d]pyrimidin-2-ylamine;
  4-(3-Aminomethyl-pyrrolidin-1-yl)-8-chloro-benzo[4,5]furo[3,2-d]pyrimidin-2-ylamine;
  (R)-4-(3-Aminomethyl-pyrrolidin-1-yl)-8-chloro-benzo[4,5]furo[3,2-d]pyrimidin-2-ylamine;
  6,8-Dichloro-4-[1,4]diazepan-1-yl-benzo[4,5]furo[3,2-d]pyrimidin-2-ylamine;
  (S,S)-4-(2,5-Diaza-bicyclo[2.2.1]hept-2-yl)-benzo[4,5]furo[3,2-d]pyrimidin-2-ylamine;
  6,8-Dichloro-4-(3-dimethylamino-pyrrolidin-1-yl)-benzo[4,5]furo[3,2-d]pyrimidin-2-ylamine;
  4-(Octahydro-pyrido[1,2-a]pyrazin-2-yl)-benzo[4,5]furo[3,2-d]pyrimidin-2-ylamine;
  6,8-Dichloro-4-(octahydro-pyrido[1,2-a]pyrazin-2-yl)-benzo[4,5]furo[3,2-d]pyrimidin-2-ylamine;
  (S,S)-6,8-Dichloro-4-(2,5-diaza-bicyclo[2.2.1]hept-2-yl)-benzo[4,5]furo[3,2-d]pyrimidin-2-ylamine;
  (R)-8-Fluoro-4-(3-methylamino-pyrrolidin-1-yl)-benzo[4,5]furo[3,2-d]pyrimidin-2-ylamine;
  8-Fluoro-4-(hexahydro-pyrrolo[1,2-a]pyrazin-2-yl)-benzo[4,5]furo[3,2-d]pyrimidin-2-ylamine;
  8-Fluoro-N⁴-methyl-N⁴-(1-methyl-pyrrolidin-3-yl)-benzo[4,5]furo[3,2-d]pyrimidine-2,4-diamine;
  (R)-8-(3-Methylamino-pyrrolidin-1-yl)-9-oxa-1,5,7-triaza-fluoren-6-ylamine;
  8-(Octahydro-pyrrolo[3,4-b]pyridin-6-yl)-9-oxa-1,5,7-triaza-fluoren-6-ylamine;
  8-Bromo-4-(octahydro-pyrrolo[3,4-b]pyridin-6-yl)-benzo[4,5]thieno[3,2-d]pyrimidin-2-ylamine;
  7-Bromo-4-(octahydro-pyrrolo[3,4-b]pyridin-6-yl)-benzo[4,5]thieno[3,2-d]pyrimidin-2-ylamine;
  (S)-8-Bromo-4-(3-methylamino-pyrrolidin-1-yl)-benzo[4,5]thieno[3,2-d]pyrimidin-2-ylamine;
  (R)-8-Bromo-4-(3-methylamino-pyrrolidin-1-yl)-benzo[4,5]thieno[3,2-d]pyrimidin-2-ylamine;
  (S,S)-8-Bromo-4-(2,5-diaza-bicyclo[2.2.1]hept-2-yl)-benzo[4,5]thieno[3,2-d]pyrimidin-2-ylamine;
  (S)-4-(3-Methylamino-pyrrolidin-1-yl)-7-trifluoromethyl-benzo[4,5]thieno[3,2-d]pyrimidin-2-ylamine;
  (R)-4-(3-Methylamino-pyrrolidin-1-yl)-7-trifluoromethyl-benzo[4,5]thieno[3,2-d]pyrimidin-2-ylamine;
  (S,S)-4-(2,5-Diaza-bicyclo[2.2.1]hept-2-yl)-7-trifluoromethyl-benzo[4,5]thieno[3,2-d]pyrimidin-2-ylamine;
  (R)-7-Bromo-4-(3-methylamino-pyrrolidin-1-yl)-benzo[4,5]thieno[3,2-d]pyrimidin-2-ylamine;
  (S)-7-Bromo-4-(3-methylamino-pyrrolidin-1-yl)-benzo[4,5]thieno[3,2-d]pyrimidin-2-ylamine;
  4-(Octahydro-pyrrolo[3,4-b]pyridin-6-yl)-7-trifluoromethyl-benzo[4,5]thieno[3,2-d]pyrimidin-2-ylamine;
  7-Chloro-4-(octahydro-pyrrolo[3,4-b]pyridin-6-yl)-benzo[4,5]thieno[3,2-d]pyrimidin-2-ylamine;
  (R)-7-Chloro-4-(3-methylamino-pyrrolidin-1-yl)-benzo[4,5]thieno[3,2-d]pyrimidin-2-ylamine;
  (S)-7-Chloro-4-(3-methylamino-pyrrolidin-1-yl)-benzo[4,5]thieno[3,2-d]pyrimidin-2-ylamine;
  (S,S)-7-Chloro-4-(2,5-diaza-bicyclo[2.2.1]hept-2-yl)-benzo[4,5]thieno[3,2-d]pyrimidin-2-ylamine;
  8-Chloro-4-(octahydro-pyrrolo[3,4-b]pyridin-6-yl)-benzo[4,5]thieno[3,2-d]pyrimidin-2-ylamine;

(S)-8-Chloro-4-(3-methylamino-pyrrolidin-1-yl)-benzo[4,5]thieno[3,2-d]pyrimidin-2-ylamine;
(R)-8-Chloro-4-(3-methylamino-pyrrolidin-1-yl)-benzo[4,5]thieno[3,2-d]pyrimidin-2-ylamine;
(S,S)-8-Chloro-4-(2,5-diaza-bicyclo[2.2.1]hept-2-yl)-benzo[4,5]thieno[3,2-d]pyrimidin-2-ylamine;
8-Chloro-4-(hexahydro-pyrrolo[1,2-a]pyrazin-2-yl)-benzo[4,5]furo[3,2-d]pyrimidin-2-ylamine;
8-Fluoro-4-(hexahydro-pyrrolo[3,4-b]pyrrol-5-yl)-benzo[4,5]furo[3,2-d]pyrimidin-2-ylamine;
(S)-8-Chloro-4-(3-ethylamino-piperidin-1-yl)-benzo[4,5]furo[3,2-d]pyrimidin-2-ylamine;
(R)-8-Chloro-4-(3-ethylamino-pyrrolidin-1-yl)-benzo[4,5]furo[3,2-d]pyrimidin-2-ylamine;
(S)-8-Chloro-4-(3-methylamino-piperidin-1-yl)-benzo[4,5]furo[3,2-d]pyrimidin-2-ylamine;
(S)-8-Chloro-4-(3-dimethylamino-piperidin-1-yl)-benzo[4,5]furo[3,2-d]pyrimidin-2-ylamine;
(R)-8-Fluoro-4-(3-methylamino-pyrrolidin-1-yl)-benzo[4,5]thieno[3,2-d]pyrimidin-2-ylamine;
(S,S)-7-Bromo-4-(2,5-diaza-bicyclo[2.2.1]hept-2-yl)-benzo[4,5]thieno[3,2-d]pyrimidin-2-ylamine;
4-(6-Amino-3-aza-bicyclo[3.1.0]hex-3-yl)-8-chloro-benzo[4,5]furo[3,2-d]pyrimidin-2-ylamine;
(R)-4-(2-Aminomethyl-pyrrolidin-1-yl)-8-chloro-benzo[4,5]furo[3,2-d]pyrimidin-2-ylamine;
8-Chloro-4-(hexahydro-pyrrolo[3,4-b]pyrrol-5-yl)-benzo[4,5]furo[3,2-d]pyrimidin-2-ylamine;
(R,R)-8-Chloro-4-(2,5-diaza-bicyclo[2.2.1]hept-2-yl)-benzo[4,5]furo[3,2-d]pyrimidin-2-ylamine;
(R,R)-8-Chloro-4-(octahydro-pyrrolo[3,4-b]pyridin-6-yl)-benzo[4,5]furo[3,2-d]pyrimidin-2-ylamine;
8-Chloro-4-(octahydro-pyrrolo[3,4-b]pyridin-6-yl)-benzo[4,5]furo[3,2-d]pyrimidin-2-ylamine;
(R)-4-(3-Methylamino-pyrrolidin-1-yl)-9-trifluoromethyl-benzo[4,5]furo[3,2-d]pyrimidin-2-ylamine;
(S,S)-4-(2,5-Diaza-bicyclo[2.2.1]hept-2-yl)-9-methoxy-benzo[4,5]furo[3,2-d]pyrimidin-2-ylamine;
(S)-4-(3-Amino-piperidin-1-yl)-9-methoxy-benzo[4,5]furo[3,2-d]pyrimidin-2-ylamine;
(S)-4-(3-Amino-piperidin-1-yl)-9-trifluoromethyl-benzo[4,5]furo[3,2-d]pyrimidin-2-ylamine;
(S)-4-(3-Amino-piperidin-1-yl)-8,9-dichloro-benzo[4,5]furo[3,2-d]pyrimidin-2-ylamine;
(S,S)-4-(2,5-Diaza-bicyclo[2.2.1]hept-2-yl)-9-trifluoromethyl-benzo[4,5]furo[3,2-d]pyrimidin-2-ylamine;
(cis)-8-Chloro-4-(hexahydro-pyrrolo[3,4-b]pyrrol-1-yl)-benzo[4,5]furo[3,2-d]pyrimidin-2-ylamine;
N⁴-(2-Amino-ethyl)-8-chloro-N⁴-methyl-benzo[4,5]furo[3,2-d]pyrimidine-2,4-diamine;
8-Chloro-4-(3,8-diaza-bicyclo[3.2.1]oct-3-yl)-benzo[4,5]furo[3,2-d]pyrimidin-2-ylamine;
(S,S)-8,9-Dichloro-4-(2,5-diaza-bicyclo[2.2.1]hept-2-yl)-benzo[4,5]furo[3,2-d]pyrimidin-2-ylamine;
(R)-8,9-Dichloro-4-(3-methylamino-pyrrolidin-1-yl)-benzo[4,5]furo[3,2-d]pyrimidin-2-ylamine;
(R)-9-Methoxy-4-(3-methylamino-pyrrolidin-1-yl)-benzo[4,5]furo[3,2-d]pyrimidin-2-ylamine;
(R)-8-Methoxy-4-(3-methylamino-pyrrolidin-1-yl)-benzo[4,5]furo[3,2-d]pyrimidin-2-ylamine;
4-(3-Aminomethyl-azetidin-1-yl)-8-chloro-benzo[4,5]furo[3,2-d]pyrimidin-2-ylamine;
(cis)-8-Methoxy-4-(octahydro-pyrrolo[3,4-b]pyridin-6-yl)-benzo[4,5]furo[3,2-d]pyrimidin-2-ylamine;
(S,S)-8-Chloro-4-(5-methyl-2,5-diaza-bicyclo[2.2.1]hept-2-yl)-benzo[4,5]furo[3,2-d]pyrimidin-2-ylamine;
(S)-4-(3-Amino-piperidin-1-yl)-8-methoxy-benzo[4,5]furo[3,2-d]pyrimidin-2-ylamine;
(R)-4-(3-Amino-pyrrolidin-1-yl)-benzo[4,5]furo[3,2-d]pyrimidin-2-ylamine;
(R)-3-Chloro-8-(3-methylamino-pyrrolidin-1-yl)-9-oxa-1,5,7-triaza-fluoren-6-ylamine;
N⁴-Azetidin-3-ylmethyl-8-chloro-benzo[4,5]furo[3,2-d]pyrimidine-2,4-diamine;
N⁴-Azetidin-3-yl-8-chloro-benzo[4,5]furo[3,2-d]pyrimidine-2,4-diamine;
N⁴-(2-Amino-ethyl)-8-chloro-benzo[4,5]furo[3,2-d]pyrimidine-2,4-diamine;
(S,S)-4-(2,5-Diaza-bicyclo[2.2.1]hept-2-yl)-8-methoxy-benzo[4,5]furo[3,2-d]pyrimidin-2-ylamine;
(cis)-4-(Hexahydro-pyrrolo[3,4-b]pyrrol-5-yl)-8-methoxy-benzo[4,5]furo[3,2-d]pyrimidin-2-ylamine;
(cis)-2-[8-Chloro-4-(octahydro-pyrrolo[3,4-b]pyridin-6-yl)-benzo[4,5]furo[3,2-d]pyrimidin-2-ylamino]-ethanol;
(S,S)-2-[8-Chloro-4-(2,5-diaza-bicyclo[2.2.1]hept-2-yl)-benzo[4,5]furo[3,2-d]pyrimidin-2-ylamino]-ethanol;
2-[8-Chloro-4-(3-methylamino-pyrrolidin-1-yl)-benzo[4,5]furo[3,2-d]pyrimidin-2-ylamino]-ethanol;
2-[8-Chloro-4-(4-methyl-[1,4]diazepan-1-yl)-benzo[4,5]furo[3,2-d]pyrimidin-2-ylamino]-ethanol;
4-(3-Amino-azetidin-1-yl)-8-chloro-benzo[4,5]furo[3,2-d]pyrimidin-2-ylamine;
(R)-9-Fluoro-4-(3-methylamino-pyrrolidin-1-yl)-benzo[4,5]furo[3,2-d]pyrimidin-2-ylamine;
4-(3-Amino-azetidin-1-yl)-9-fluoro-benzo[4,5]furo[3,2-d]pyrimidin-2-ylamine;
(R)-4-(3-Methylamino-pyrrolidin-1-yl)-8-trifluoromethyl-benzo[4,5]furo[3,2-d]pyrimidin-2-ylamine;
(S)-4-(3-Amino-piperidin-1-yl)-8-trifluoromethyl-benzo[4,5]furo[3,2-d]pyrimidin-2-ylamine;
(S,S)-4-(2,5-Diaza-bicyclo[2.2.1]hept-2-yl)-8-trifluoromethyl-benzo[4,5]furo[3,2-d]pyrimidin-2-ylamine;
4-(3-Amino-azetidin-1-yl)-8-trifluoromethyl-benzo[4,5]furo[3,2-d]pyrimidin-2-ylamine;
(S)-4-(3-Amino-piperidin-1-yl)-8,9-difluoro-benzo[4,5]furo[3,2-d]pyrimidin-2-ylamine;
(R)-8,9-Difluoro-4-(3-methylamino-pyrrolidin-1-yl)-benzo[4,5]furo[3,2-d]pyrimidin-2-ylamine;
(S,S)-4-(2,5-Diaza-bicyclo[2.2.1]hept-2-yl)-8,9-difluoro-benzo[4,5]furo[3,2-d]pyrimidin-2-ylamine;
4-(3-Amino-azetidin-1-yl)-8,9-difluoro-benzo[4,5]furo[3,2-d]pyrimidin-2-ylamine;
(R)-9-Chloro-4-(3-methylamino-pyrrolidin-1-yl)-benzo[4,5]furo[3,2-d]pyrimidin-2-ylamine;
(S)-4-(3-Amino-piperidin-1-yl)-9-chloro-benzo[4,5]furo[3,2-d]pyrimidin-2-ylamine;
(S,S)-9-Chloro-4-(2,5-diaza-bicyclo[2.2.1]hept-2-yl)-benzo[4,5]furo[3,2-d]pyrimidin-2-ylamine;
4-(3-Amino-azetidin-1-yl)-9-chloro-benzo[4,5]furo[3,2-d]pyrimidin-2-ylamine;
(R)-7-Methoxy-4-(3-methylamino-pyrrolidin-1-yl)-benzo[4,5]thieno[3,2-d]pyrimidin-2-ylamine;
(S)-7-Methoxy-4-(3-methylamino-pyrrolidin-1-yl)-benzo[4,5]thieno[3,2-d]pyrimidin-2-ylamine;
(S)-2-[4-(3-Amino-piperidin-1-yl)-8-chloro-benzo[4,5]furo[3,2-d]pyrimidin-2-ylamino]-ethanol;
2-[4-(3-Amino-azetidin-1-yl)-8-chloro-benzo[4,5]furo[3,2-d]pyrimidin-2-ylamino]-ethanol;
and pharmaceutically acceptable salts thereof.

22. A pharmaceutical composition comprising at least one of a chemical entity selected from compounds of Formula (I), and pharmaceutically acceptable salts of compounds of Formula (I):

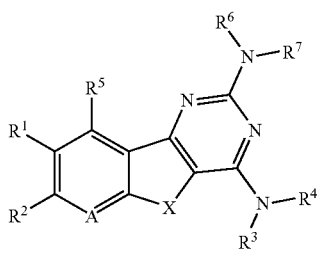
(I)

wherein $R^1$ and $R^2$ are each independently H, Cl, F, Br, methyl, ethyl, methoxy, $NO_2$, or $CF_3$;

$R^5$ is H, methoxy, Cl, F, Br, or $CF_3$;

A is N or $CR^a$;
where $R^a$ is H or Cl;
with the proviso that at least two of $R^1$, $R^2$, $R^5$, and $R^a$ are H;

X is O or S;

$-N(R^3)R^4$ is one of the moieties:

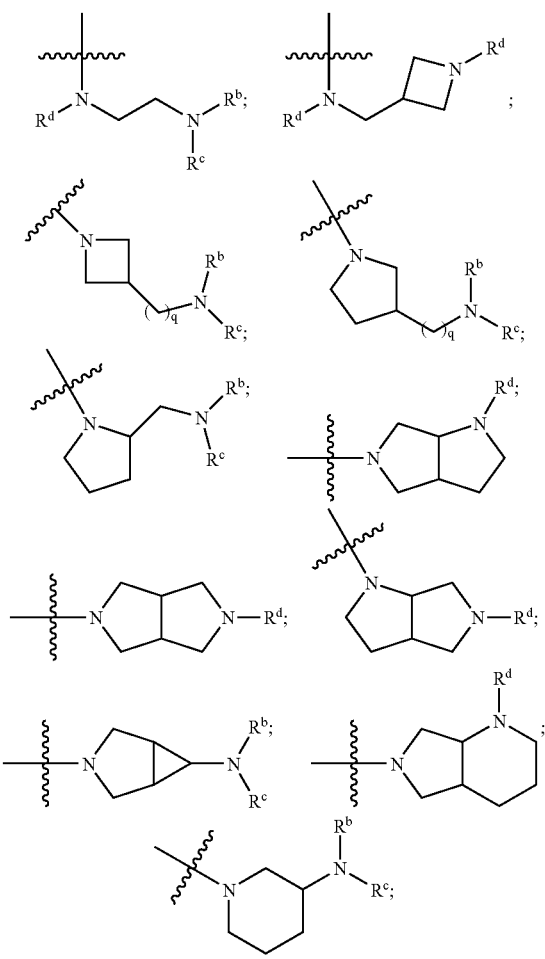

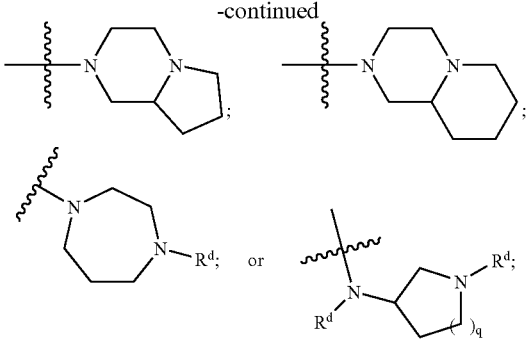

where q is 0 or 1;

$R^3$ and $R^4$ are taken together or separately as defined by the structure of each one of said moieties;

$R^b R^c$ and $R^d$ are each independently H or $C_{1-3}$alkyl; and each $R^e$ substitutent is methyl or two $R^e$ substituents taken together form a methylene or ethylene bridge;

$R^6$ is H or methyl;

$R^7$ is H; $C_{1-4}$alkyl unsubstituted or substituted with —OH, —$SCH_3$, or —$NH_2$; allyl; or cyclopropyl.

23. A pharmaceutical composition according to claim 22, wherein said chemical entity is selected from:

6,8-Dichloro-4-(octahydro-pyrrolo[3,4-b]pyridin-6-yl)-benzo[4,5]furo[3,2-d]pyrimidin-2-ylamine;

8-Chloro-4-(4-isopropyl-[1,4]diazepan-1-yl)-benzo[4,5]furo[3,2-d]pyrimidin-2-ylamine;

4-(3-Amino-pyrrolidin-1-yl)-6,8-dichloro-benzo[4,5]furo[3,2-d]pyrimidin-2-ylamine;

(R)-6,8-Dichloro-4-(3-methylamino-pyrrolidin-1-yl)-benzo[4,5]furo[3,2-d]pyrimidin-2-ylamine;

(R)-4-(3-Methylamino-pyrrolidin-1-yl)-benzo[4,5]furo[3,2-d]pyrimidin-2-ylamine;

8-Chloro-4-[1,4]diazepan-1-yl-benzo[4,5]furo[3,2-d]pyrimidin-2-ylamine;

8-Chloro-4-(octahydro-pyrido[1,2-a]pyrazin-2-yl)-benzo[4,5]furo[3,2-d]pyrimidin-2-ylamine;

8-Chloro-4-(octahydro-pyrrolo[3,4-b]pyridin-6-yl)-benzo[4,5]furo[3,2-d]pyrimidin-2-ylamine;

8-Chloro-4-(4-methyl-[1,4]diazepan-1-yl)-benzo[4,5]furo[3,2-d]pyrimidin-2-ylamine;

(S,S)-8-Chloro-4-(2,5-diaza-bicyclo[2.2.1]hept-2-yl)-benzo[4,5]furo[3,2-d]pyrimidin-2-ylamine;

8-Chloro-4-(3-methylamino-pyrrolidin-1-yl)-benzo[4,5]furo[3,2-d]pyrimidin-2-ylamine;

(S)-4-(3-Amino-piperidin-1-yl)-8-chloro-benzo[4,5]furo[3,2-d]pyrimidin-2-ylamine;

8-Chloro-4-(3-dimethylamino-pyrrolidin-1-yl)-benzo[4,5]furo[3,2-d]pyrimidin-2-ylamine;

4-(3-Amino-pyrrolidin-1-yl)-8-chloro-benzo[4,5]furo[3,2-d]pyrimidin-2-ylamine;

(S)-8-Chloro-4-(3-methylamino-pyrrolidin-1-yl)-benzo[4,5]furo[3,2-d]pyrimidin-2-ylamine;

(R)-8-Chloro-4-(3-methylamino-pyrrolidin-1-yl)-benzo[4,5]furo[3,2-d]pyrimidin-2-ylamine;

(R)-8-Bromo-4-(3-methylamino-pyrrolidin-1-yl)-benzo[4,5]furo[3,2-d]pyrimidin-2-ylamine;

8-Bromo-4-(hexahydro-pyrrolo[1,2-a]pyrazin-2-yl)-benzo[4,5]furo[3,2-d]pyrimidin-2-ylamine;

4-(3-Amino-pyrrolidin-1-yl)-benzo[4,5]furo[3,2-d]pyrimidin-2-ylamine;

(R)-4-(3-Dimethylamino-pyrrolidin-1-yl)-benzo[4,5]furo[3,2-d]pyrimidin-2-ylamine;

(R)-8-Chloro-4-(3-dimethylamino-pyrrolidin-1-yl)-benzo[4,5]furo[3,2-d]pyrimidin-2-ylamine;
(R)-4-(3-Amino-pyrrolidin-1-yl)-8-chloro-benzo[4,5]furo[3,2-d]pyrimidin-2-ylamine;
(S)-4-(3-Aminomethyl-pyrrolidin-1-yl)-8-chloro-benzo[4,5]furo[3,2-d]pyrimidin-2-ylamine;
8-Chloro-4-(hexahydro-pyrrolo[3,4-c]pyrrol-2-yl)-benzo[4,5]furo[3,2-d]pyrimidin-2-ylamine;
(R)-4-(3-Amino-piperidin-1-yl)-8-chloro-benzo[4,5]furo[3,2-d]pyrimidin-2-ylamine;
4-(3-Aminomethyl-pyrrolidin-1-yl)-8-chloro-benzo[4,5]furo[3,2-d]pyrimidin-2-ylamine;
(R)-4-(3-Aminomethyl-pyrrolidin-1-yl)-8-chloro-benzo[4,5]furo[3,2-d]pyrimidin-2-ylamine;
6,8-Dichloro-4-[1,4]diazepan-1-yl-benzo[4,5]furo[3,2-d]pyrimidin-2-ylamine;
(S,S)-4-(2,5-Diaza-bicyclo[2.2.1]hept-2-yl)-benzo[4,5]furo[3,2-d]pyrimidin-2-ylamine;
6,8-Dichloro-4-(3-dimethylamino-pyrrolidin-1-yl)-benzo[4,5]furo[3,2-d]pyrimidin-2-ylamine;
4-(Octahydro-pyrido[1,2-a]pyrazin-2-yl)-benzo[4,5]furo[3,2-d]pyrimidin-2-ylamine;
6,8-Dichloro-4-(octahydro-pyrido[1,2-a]pyrazin-2-yl)-benzo[4,5]furo[3,2-d]pyrimidin-2-ylamine;
(S,S)-6,8-Dichloro-4-(2,5-diaza-bicyclo[2.2.1]hept-2-yl)-benzo[4,5]furo[3,2-d]pyrimidin-2-ylamine;
(R)-8-Fluoro-4-(3-methylamino-pyrrolidin-1-yl)-benzo[4,5]furo[3,2-d]pyrimidin-2-ylamine;
8-Fluoro-4-(hexahydro-pyrrolo[1,2-a]pyrazin-2-yl)-benzo[4,5]furo[3,2-d]pyrimidin-2-ylamine;
8-Fluoro-$N^4$-methyl-$N^4$-(1-methyl-pyrrolidin-3-yl)-benzo[4,5]furo[3,2-d]pyrimidine-2,4-diamine;
(R)-8-(3-Methylamino-pyrrolidin-1-yl)-9-oxa-1,5,7-triaza-fluoren-6-ylamine;
8-(Octahydro-pyrrolo[3,4-b]pyridin-6-yl)-9-oxa-1,5,7-triaza-fluoren-6-ylamine;
8-Bromo-4-(octahydro-pyrrolo[3,4-b]pyridin-6-yl)-benzo[4,5]thieno[3,2-d]pyrimidin-2-ylamine;
7-Bromo-4-(octahydro-pyrrolo[3,4-b]pyridin-6-yl)-benzo[4,5]thieno[3,2-d]pyrimidin-2-ylamine;
(S)-8-Bromo-4-(3-methylamino-pyrrolidin-1-yl)-benzo[4,5]thieno[3,2-d]pyrimidin-2-ylamine;
(R)-8-Bromo-4-(3-methylamino-pyrrolidin-1-yl)-benzo[4,5]thieno[3,2-d]pyrimidin-2-ylamine;
(S,S)-8-Bromo-4-(2,5-diaza-bicyclo[2.2.1]hept-2-yl)-benzo[4,5]thieno[3,2-d]pyrimidin-2-ylamine;
(S)-4-(3-Methylamino-pyrrolidin-1-yl)-7-trifluoromethyl-benzo[4,5]thieno[3,2-d]pyrimidin-2-ylamine;
(R)-4-(3-Methylamino-pyrrolidin-1-yl)-7-trifluoromethyl-benzo[4,5]thieno[3,2-d]pyrimidin-2-ylamine;
(S,S)-4-(2,5-Diaza-bicyclo[2.2.1]hept-2-yl)-7-trifluoromethyl-benzo[4,5]thieno[3,2-d]pyrimidin-2-ylamine;
(R)-7-Bromo-4-(3-methylamino-pyrrolidin-1-yl)-benzo[4,5]thieno[3,2-d]pyrimidin-2-ylamine;
(S)-7-Bromo-4-(3-methylamino-pyrrolidin-1-yl)-benzo[4,5]thieno[3,2-d]pyrimidin-2-ylamine;
4-(Octahydro-pyrrolo[3,4-b]pyridin-6-yl)-7-trifluoromethyl-benzo[4,5]thieno[3,2-d]pyrimidin-2-ylamine;
7-Chloro-4-(octahydro-pyrrolo[3,4-b]pyridin-6-yl)-benzo[4,5]thieno[3,2-d]pyrimidin-2-ylamine;
(R)-7-Chloro-4-(3-methylamino-pyrrolidin-1-yl)-benzo[4,5]thieno[3,2-d]pyrimidin-2-ylamine;
(S)-7-Chloro-4-(3-methylamino-pyrrolidin-1-yl)-benzo[4,5]thieno[3,2-d]pyrimidin-2-ylamine;
(S,S)-7-Chloro-4-(2,5-diaza-bicyclo[2.2.1]hept-2-yl)-benzo[4,5]thieno[3,2-d]pyrimidin-2-ylamine;
8-Chloro-4-(octahydro-pyrrolo[3,4-b]pyridin-6-yl)-benzo[4,5]thieno[3,2-d]pyrimidin-2-ylamine;
(S)-8-Chloro-4-(3-methylamino-pyrrolidin-1-yl)-benzo[4,5]thieno[3,2-d]pyrimidin-2-ylamine;
(R)-8-Chloro-4-(3-methylamino-pyrrolidin-1-yl)-benzo[4,5]thieno[3,2-d]pyrimidin-2-ylamine;
(S,S)-8-Chloro-4-(2,5-diaza-bicyclo[2.2.1]hept-2-yl)-benzo[4,5]thieno[3,2-d]pyrimidin-2-ylamine;
8-Chloro-4-(hexahydro-pyrrolo[1,2-a]pyrazin-2-yl)-benzo[4,5]furo[3,2-d]pyrimidin-2-ylamine;
8-Fluoro-4-(hexahydro-pyrrolo[3,4-b]pyrrol-5-yl)-benzo[4,5]furo[3,2-d]pyrimidin-2-ylamine;
(S)-8-Chloro-4-(3-ethylamino-piperidin-1-yl)-benzo[4,5]furo[3,2-d]pyrimidin-2-ylamine;
(R)-8-Chloro-4-(3-ethylamino-pyrrolidin-1-yl)-benzo[4,5]furo[3,2-d]pyrimidin-2-ylamine;
(S)-8-Chloro-4-(3-methylamino-piperidin-1-yl)-benzo[4,5]furo[3,2-d]pyrimidin-2-ylamine;
(S)-8-Chloro-4-(3-dimethylamino-piperidin-1-yl)-benzo[4,5]furo[3,2-d]pyrimidin-2-ylamine;
(R)-8-Fluoro-4-(3-methylamino-pyrrolidin-1-yl)-benzo[4,5]thieno[3,2-d]pyrimidin-2-ylamine;
(S,S)-7-Bromo-4-(2,5-diaza-bicyclo[2.2.1]hept-2-yl)-benzo[4,5]thieno[3,2-d]pyrimidin-2-ylamine;
4-(6-Amino-3-aza-bicyclo[3.1.0]hex-3-yl)-8-chloro-benzo[4,5]furo[3,2-d]pyrimidin-2-ylamine;
(R)-4-(2-Aminomethyl-pyrrolidin-1-yl)-8-chloro-benzo[4,5]furo[3,2-d]pyrimidin-2-ylamine;
8-Chloro-4-(hexahydro-pyrrolo[3,4-b]pyrrol-5-yl)-benzo[4,5]furo[3,2-d]pyrimidin-2-ylamine;
(R,R)-8-Chloro-4-(2,5-diaza-bicyclo[2.2.1]hept-2-yl)-benzo[4,5]furo[3,2-d]pyrimidin-2-ylamine;
(R,R)-8-Chloro-4-(octahydro-pyrrolo[3,4-b]pyridin-6-yl)-benzo[4,5]furo[3,2-d]pyrimidin-2-ylamine;
8-Chloro-4-(octahydro-pyrrolo[3,4-b]pyridin-6-yl)-benzo[4,5]furo[3,2-d]pyrimdin-2-ylamine;
(R)-4-(3-Methylamino-pyrrolidin-1-yl)-9-trifluoromethyl-benzo[4,5]furo[3,2-d]pyrimidin-2-ylamine;
(S,S)-4-(2,5-Diaza-bicyclo[2.2.1]hept-2-yl)-9-methoxy-benzo[4,5]furo[3,2-d]pyrimidin-2-ylamine;
(S)-4-(3-Amino-piperidin-1-yl)-9-methoxy-benzo[4,5]furo[3,2-d]pyrimidin-2-ylamine;
(S)-4-(3-Amino-piperidin-1-yl)-9-trifluoromethyl-benzo[4,5]furo[3,2-d]pyrimidin-2-ylamine;
(S)-4-(3-Amino-piperidin-1-yl)-8,9-dichloro-benzo[4,5]furo[3,2-d]pyrimidin-2-ylamine;
(S,S)-4-(2,5-Diaza-bicyclo[2.2.1]hept-2-yl)-9-trifluoromethyl-benzo[4,5]furo[3,2-d]pyrimidin-2-ylamine;
(cis)-8-Chloro-4-(hexahydro-pyrrolo[3,4-b]pyrrol-1-yl)-benzo[4,5]furo[3,2-d]pyrimidin-2-ylamine;
$N^4$-(2-Amino-ethyl)-8-chloro-$N^4$-methyl-benzo[4,5]furo[3,2-d]pyrimidine-2,4-diamine;
8-Chloro-4-(3,8-diaza-bicyclo[3.2.1]oct-3-yl)-benzo[4,5]furo[3,2-d]pyrimidin-2-ylamine;
(S,S)-8,9-Dichloro-4-(2,5-diaza-bicyclo[2.2.1]hept-2-yl)-benzo[4,5]furo[3,2-d]pyrimidin-2-ylamine;
(R)-8,9-Dichloro-4-(3-methylamino-pyrrolidin-1-yl)-benzo[4,5]furo[3,2-d]pyrimidin-2-ylamine;
(R)-9-Methoxy-4-(3-methylamino-pyrrolidin-1-yl)-benzo[4,5]furo[3,2-d]pyrimidin-2-ylamine;
(R)-8-Methoxy-4-(3-methylamino-pyrrolidin-1-yl)-benzo[4,5]furo[3,2-d]pyrimidin-2-ylamine;
4-(3-Aminomethyl-azetidin-1-yl)-8-chloro-benzo[4,5]furo[3,2-d]pyrimidin-2-ylamine;
(cis)-8-Methoxy-4-(octahydro-pyrrolo[3,4-b]pyridin-6-yl)-benzo[4,5]furo[3,2-d]pyrimidin-2-ylamine;

(S,S)-8-Chloro-4-(5-methyl-2,5-diaza-bicyclo[2.2.1]
hept-2-yl)-benzo[4,5]furo[3,2-d]pyrimidin-2-ylamine;
(S)-4-(3-Amino-piperidin-1-yl)-8-methoxy-benzo[4,5]
furo[3,2-d]pyrimidin-2-ylamine;
(R)-4-(3-Amino-pyrrolidin-1-yl)-benzo[4,5]furo[3,2-d]
pyrimidin-2-ylamine;
(R)-3-Chloro-8-(3-methylamino-pyrrolidin-1-yl)-9-oxa-
1,5,7-triaza-fluoren-6-ylamine;
N⁴-Azetidin-3-ylmethyl-8-chloro-benzo[4,5]furo[3,2-d]
pyrimidine-2,4-diamine;
N⁴-Azetidin-3-yl-8-chloro-benzo[4,5]furo[3,2-d]pyrimi-
dine-2,4-diamine;
N⁴-(2-Amino-ethyl)-8-chloro-benzo[4,5]furo[3,2-d]pyri-
midine-2,4-diamine;
(S,S)-4-(2,5-Diaza-bicyclo[2.2.1]hept-2-yl)-8-methoxy-
benzo[4,5]furo[3,2-d]pyrimidin-2-ylamine;
(cis)-4-(Hexahydro-pyrrolo[3,4-b]pyrrol-5-yl)-8-meth-
oxy-benzo[4,5]furo[3,2-d]pyrimidin-2-ylamine;
(cis)-2-[8-Chloro-4-(octahydro-pyrrolo[3,4-b]pyridin-6-
yl)-benzo[4,5]furo[3,2-d]pyrimidin-2-ylamino]-etha-
nol;
(S,S)-2-[8-Chloro-4-(2,5-diaza-bicyclo[2.2.1]hept-2-yl)-
benzo[4,5]furo[3,2-d]pyrimidin-2-ylamino]-ethanol;
2-[8-Chloro-4-(3-methylamino-pyrrolidin-1-yl)-benzo[4,
5]furo[3,2-d]pyrimidin-2-ylamino]-ethanol;
2-[8-Chloro-4-(4-methyl-[1,4]diazepan-1-yl)-benzo[4,5]
furo[3,2-d]pyrimidin-2-ylamino]-ethanol;
4-(3-Amino-azetidin-1-yl)-8-chloro-benzo[4,5]furo[3,2-
d]pyrimidin-2-ylamine;
(R)-9-Fluoro-4-(3-methylamino-pyrrolidin-1-yl)-benzo
[4,5]furo[3,2-d]pyrimidin-2-ylamine;
4-(3-Amino-azetidin-1-yl)-9-fluoro-benzo[4,5]furo[3,2-
d]pyrimidin-2-ylamine;
(R)-4-(3-Methylamino-pyrrolidin-1-yl)-8-trifluorom-
ethyl-benzo[4,5]furo[3,2-d]pyrimidin-2-ylamine;
(S)-4-(3-Amino-piperidin-1-yl)-8-trifluoromethyl-benzo
[4,5]furo[3,2-d]pyrimidin-2-ylamine;
(S,S)-4-(2,5-Diaza-bicyclo[2.2.1]hept-2-yl)-8-trifluorom-
ethyl-benzo[4,5]furo[3,2-d]pyrimidin-2-ylamine;
4-(3-Amino-azetidin-1-yl)-8-trifluoromethyl-benzo[4,5]
furo[3,2-d]pyrimidin-2-ylamine;
(S)-4-(3-Amino-piperidin-1-yl)-8,9-difluoro-benzo[4,5]
furo[3,2-d]pyrimidin-2-ylamine;
(R)-8,9-Difluoro-4-(3-methylamino-pyrrolidin-1-yl)-
benzo[4,5]furo[3,2-d]pyrimidin-2-ylamine;
(S,S)-4-(2,5-Diaza-bicyclo[2.2.1]hept-2-yl)-8,9-difluoro-
benzo[4,5]furo[3,2-d]pyrimidin-2-ylamine;
4-(3-Amino-azetidin-1-yl)-8,9-difluoro-benzo[4,5]furo
[3,2-d]pyrimidin-2-ylamine;
(R)-9-Chloro-4-(3-methylamino-pyrrolidin-1-yl)-benzo
[4,5]furo[3,2-d]pyrimidin-2-ylamine;
(S)-4-(3-Amino-piperidin-1-yl)-9-chloro-benzo[4,5]furo
[3,2-d]pyrimidin-2-ylamine;
(S,S)-9-Chloro-4-(2,5-diaza-bicyclo[2.2.1]hept-2-yl)-
benzo[4,5]furo[3,2-d]pyrimidin-2-ylamine;
4-(3-Amino-azetidin-1-yl)-9-chloro-benzo[4,5]furo[3,2-
d]pyrimidin-2-ylamine;
(R)-7-Methoxy-4-(3-methylamino-pyrrolidin-1-yl)-
benzo[4,5]thieno[3,2-d]pyrimidin-2-ylamine;
(S)-7-Methoxy-4-(3-methylamino-pyrrolidin-1-yl)-benzo
[4,5]thieno[3,2-d]pyrimidin-2-ylamine;
(S)-2-[4-(3-Amino-piperidin-1-yl)-8-chloro-benzo[4,5]
furo[3,2-d]pyrimidin-2-ylamino]-ethanol;
2-[4-(3-Amino-azetidin-1-yl)-8-chloro-benzo[4,5]furo[3,
2-d]pyrimidin-2-ylamino]-ethanol;
and pharmaceutically acceptable salts thereof.

24. A method of making a compound of Formula (I):

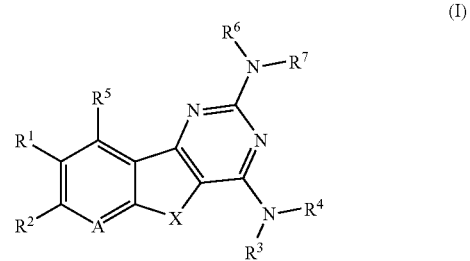

or a pharmaceutically acceptable salt thereof, comprising reacting a compound of formula (XII):

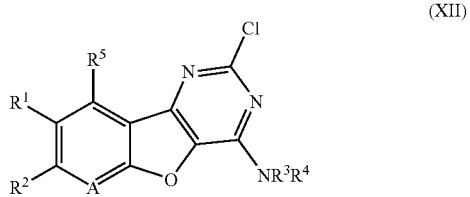

with an amine of formula $HN(R^6)R^7$ to form a compound of Formula (I), wherein
$R^1$ and $R^2$ are each independently H, Cl, F, methyl, ethyl, methoxy, $NO_2$, or $OF_3$;
$R^5$ is H, methoxy, Cl, F, or $OF_3$;
A is $CR^a$;
where $R^a$ is H or Cl;
with the proviso that at least two of $R^1$, $R^2$, $R^5$, and $R^a$ are H;
X is O;
—$N(R^3)R^4$ is one of the moieties:

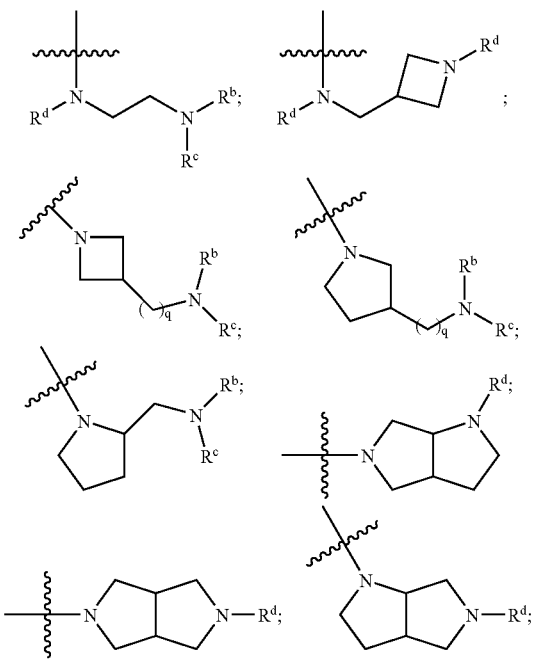

-continued

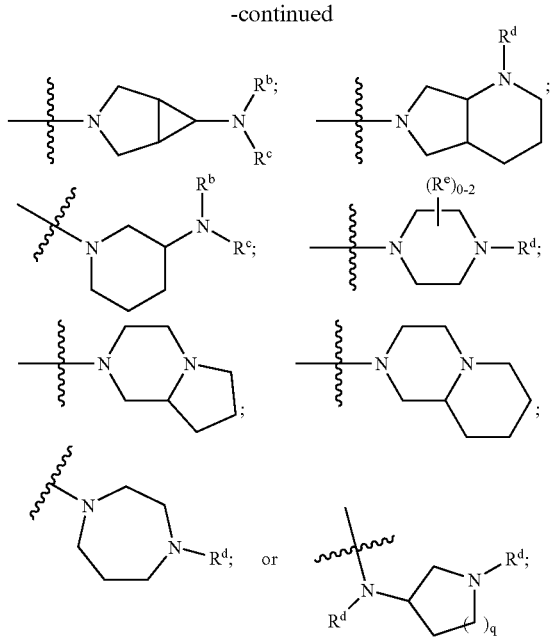

where q is 0 or 1;
R³ and R⁴ are taken together or separately as defined by the structure of each one of said moieties;
$R^b R^c$ and $R^d$ are each independently H or $C_{1-3}$alkyl; and each $R^e$ substitutent is methyl or two $R^e$ substituents taken together form a methylene or ethylene bridge;
$R^6$ is H or methyl;
$R^7$ is H; $C_{1-4}$alkyl unsubstituted or substituted with —OH, —$SCH_3$, or —$NH_2$; allyl; or cyclopropyl.

25. A method according to claim 24, further comprising reacting a compound of formula (XX):

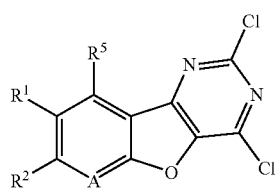

(XX)

with an amine of formula $HN(R^3)R^4$ to form a compound of formula (XII).

26. A method according to claim 25, wherein the compound of formula (XX) is 2,4,8-trichloro-benzo[4,5]furo[3,2-d]pyrimidine.

27. A method according to claim 24, further comprising reacting a compound of formula (XIX):

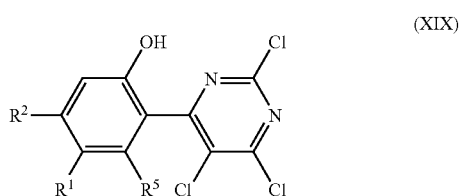

(XIX)

in the presence of a copper(I) catalyst to form a compound of formula (XX).

28. A method according to claim 27, wherein the compound of formula (XX) is 2,4,8-trichloro-benzo[4,5]furo[3,2-d]pyrimidine.

29. A method according to claim 24, further comprising reacting 2,4,5,6-tetrachloropyrimidine with a boronic acid of formula (XVIII), or a protected derivative thereof:

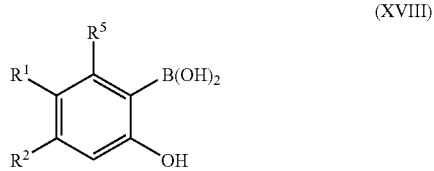

(XVIII)

in the presence of a palladium catalyst, to form a compound of formula (XIX).

30. A method according to claim 29, wherein the boronic acid of formula (XVIII), or a protected derivative thereof, is 5-chloro-2-methoxy-phenylboronic acid.

* * * * *

UNITED STATES PATENT AND TRADEMARK OFFICE
CERTIFICATE OF CORRECTION

| | |
|---|---|
| PATENT NO. | : 7,576,092 B2 |
| APPLICATION NO. | : 11/827354 |
| DATED | : August 18, 2009 |
| INVENTOR(S) | : Frank Chavez et al. |

It is certified that error appears in the above-identified patent and that said Letters Patent is hereby corrected as shown below:

Claim 1, column 87:
    line 30, there should be a "," between $R^b$ and $R^C$ and the superscript "C" should be lower case. Thus, the present recitation "$R^b R^C$" should be changed to read $R^b$, $R^c$--;

lines 31-32, the recitation "each $R^e$ substituent is methyl or two $R^e$ substituents taken together to form a methylene or ethylene bridge" should be deleted.

Claim 22, column 94:
    line 20, there should be a "," between $R^b$ and $R^C$ and the superscript "C" should be lower case. Thus, the present recitation "$R^b R^C$" should be changed to read --$R^b$, $R^c$--;

line 21, the recitation "each $R^e$ substituent is methyl or two $R^e$ substituents taken together to form a methylene or ethylene bridge" should be deleted.

Claim 24, column 99, line 31:
    There should be a "," between $R^b$ and $R^C$ and the superscript "C" should be lower case. Thus, the present recitation "$R^b R^C$" should be changed to read --$R^b$, $R^c$--.

Signed and Sealed this
Eighth Day of May, 2012

David J. Kappos
*Director of the United States Patent and Trademark Office*